United States Patent
Schlemper et al.

(10) Patent No.: US 12,181,553 B2
(45) Date of Patent: *Dec. 31, 2024

(54) DEEP LEARNING TECHNIQUES FOR MAGNETIC RESONANCE IMAGE RECONSTRUCTION

(71) Applicant: Hyperfine Operations, Inc., Guilford, CT (US)

(72) Inventors: Jo Schlemper, Long Island City, NY (US); Seyed Sadegh Mohseni Salehi, Bloomfield, NJ (US); Michal Sofka, Princeton, NJ (US); Prantik Kundu, Branford, CT (US); Ziyi Wang, Durham, NC (US); Carole Lazarus, Paris (FR); Hadrien A. Dyvorne, New York, NY (US); Laura Sacolick, Guilford, CT (US); Rafael O'Halloran, Guilford, CT (US); Jonathan M. Rothberg, Miami Beach, FL (US)

(73) Assignee: Hyperfine Operations, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/702,545

(22) Filed: Mar. 23, 2022

(65) Prior Publication Data
US 2022/0214417 A1 Jul. 7, 2022

Related U.S. Application Data

(63) Continuation of application No. 16/524,638, filed on Jul. 29, 2019, now Pat. No. 11,300,645.
(Continued)

(51) Int. Cl.
*G01R 33/56* (2006.01)
*G01R 33/561* (2006.01)
(Continued)

(52) U.S. Cl.
CPC ....... *G01R 33/5608* (2013.01); *G01R 33/561* (2013.01); *G06F 17/142* (2013.01);
(Continued)

(58) Field of Classification Search
CPC .............. G01R 33/4824; G01R 33/561; G01R 33/4818; G01R 33/5608; G06T 2207/10088
See application file for complete search history.

(56) References Cited

U.S. PATENT DOCUMENTS 7,019,524 B2  3/2006 Gurr et al.
7,042,219 B2  5/2006 Biglieri et al.
(Continued)

FOREIGN PATENT DOCUMENTS

CN  107110930 A  8/2017
CN  107507148 A  12/2017
(Continued)

OTHER PUBLICATIONS

Schlemper, Jo, et al. "A deep cascade of convolutional neural networks for MR image reconstruction." https://arxiv.org/abs/1703.00555, Mar. 1, 2017. (Year: 2017).*
(Continued)

*Primary Examiner* — Vincent Rudolph
*Assistant Examiner* — Raphael Schwartz
(74) *Attorney, Agent, or Firm* — Foley & Lardner LLP

(57) ABSTRACT

A magnetic resonance imaging (MRI) system, comprising: a magnetics system comprising: a $B_0$ magnet configured to provide a $B_0$ field for the MRI system; gradient coils configured to provide gradient fields for the MRI system; and at least one RF coil configured to detect magnetic resonance (MR) signals; and a controller configured to: control the magnetics system to acquire MR spatial frequency data using non-Cartesian sampling; and generate an
(Continued)

MR image from the acquired MR spatial frequency data using a neural network model comprising one or more neural network blocks including a first neural network block, wherein the first neural network block is configured to perform data consistency processing using a non-uniform Fourier transformation.

22 Claims, 34 Drawing Sheets

Related U.S. Application Data

(60) Provisional application No. 62/820,119, filed on Mar. 18, 2019, provisional application No. 62/744,529, filed on Oct. 11, 2018, provisional application No. 62/737,524, filed on Sep. 27, 2018, provisional application No. 62/711,895, filed on Jul. 30, 2018.

(51) Int. Cl.
| | | |
|---|---|---|
| G06F 17/14 | (2006.01) | |
| G06F 17/18 | (2006.01) | |
| G06N 3/045 | (2023.01) | |
| G06N 3/08 | (2023.01) | |
| G06T 11/00 | (2006.01) | |
| G06V 10/44 | (2022.01) | |
| G06V 10/70 | (2022.01) | |
| G06V 10/764 | (2022.01) | |

(52) U.S. Cl.
CPC ............. *G06F 17/18* (2013.01); *G06N 3/045* (2023.01); *G06N 3/08* (2013.01); *G06T 11/006* (2013.01); *G06V 10/454* (2022.01); *G06V 10/764* (2022.01); *G06V 10/768* (2022.01); *G06T 2210/41* (2013.01)

(56) References Cited

U.S. PATENT DOCUMENTS

| | | |
|---|---|---|
| 7,202,663 B2 | 4/2007 | Huang |
| 7,412,279 B2 | 8/2008 | Weisskoff et al. |
| 7,602,183 B2 | 10/2009 | Lustig et al. |
| 7,688,068 B2 | 3/2010 | Beatty |
| 7,881,511 B2 | 2/2011 | Ye et al. |
| 8,160,345 B2 | 4/2012 | Pavlovskaia et al. |
| 8,170,315 B2 | 5/2012 | Mistretta et al. |
| 8,354,844 B2 | 1/2013 | Zaitsev et al. |
| 8,384,383 B2 | 2/2013 | Frahm et al. |
| 8,442,285 B2 | 5/2013 | Madabhushi et al. |
| 8,473,028 B2 | 6/2013 | Mitsouras et al. |
| 8,494,905 B2 | 7/2013 | Pradeep et al. |
| 8,532,361 B2 | 9/2013 | Pavlovskaia et al. |
| 8,692,549 B2 | 4/2014 | Grady et al. |
| 8,781,197 B2 | 7/2014 | Wang et al. |
| 9,208,263 B2 | 12/2015 | Pavlovskaia et al. |
| 9,224,210 B2 | 12/2015 | Epstein et al. |
| 9,256,966 B2 | 2/2016 | Jacobs et al. |
| 9,269,127 B2 | 2/2016 | Ding et al. |
| 9,285,449 B2 | 3/2016 | Liu et al. |
| 9,396,562 B2 | 7/2016 | Lefebvre et al. |
| 9,541,616 B2 | 1/2017 | Rothberg et al. |
| 9,547,057 B2 | 1/2017 | Rearick et al. |
| 9,625,543 B2 | 4/2017 | Rearick et al. |
| 9,625,544 B2 | 4/2017 | Poole et al. |
| 9,638,773 B2 | 5/2017 | Poole et al. |
| 9,645,210 B2 | 5/2017 | McNulty et al. |
| 9,770,223 B2 | 9/2017 | Samsonov et al. |
| 9,797,971 B2 | 10/2017 | Rearick et al. |
| 9,817,093 B2 | 11/2017 | Rothberg et al. |
| 9,921,285 B2 | 3/2018 | Otazo et al. |
| 9,958,521 B2 | 5/2018 | Kaditz et al. |
| 9,964,615 B2 | 5/2018 | Fuderer et al. |
| 9,965,863 B2 | 5/2018 | Xu et al. |
| 10,022,562 B2 | 7/2018 | Sankey |
| 10,026,186 B2 | 7/2018 | Gerganov et al. |
| 10,073,160 B2 | 9/2018 | Boernert et al. |
| 10,139,464 B2 | 11/2018 | Rearick et al. |
| 10,145,913 B2 | 12/2018 | Hugon et al. |
| 10,145,922 B2 | 12/2018 | Rothberg et al. |
| 10,222,434 B2 | 3/2019 | Poole et al. |
| 10,222,435 B2 | 3/2019 | Mileski et al. |
| 10,241,177 B2 | 3/2019 | Poole et al. |
| 10,274,561 B2 | 4/2019 | Poole et al. |
| 10,274,563 B2 | 4/2019 | Choi |
| 10,281,540 B2 | 5/2019 | Mileski et al. |
| 10,281,541 B2 | 5/2019 | Poole et al. |
| 10,281,549 B2 | 5/2019 | Takeshima |
| 10,295,628 B2 | 5/2019 | Mileski et al. |
| 10,310,037 B2 | 6/2019 | McNulty et al. |
| 10,324,147 B2 | 6/2019 | McNulty et al. |
| 10,330,755 B2 | 6/2019 | Poole et al. |
| 10,353,030 B2 | 7/2019 | Poole et al. |
| 10,371,773 B2 | 8/2019 | Poole et al. |
| 10,379,186 B2 | 8/2019 | Rothberg et al. |
| 10,416,264 B2 | 9/2019 | Sofka et al. |
| 10,436,869 B2 | 10/2019 | Ham |
| 10,444,310 B2 | 10/2019 | Poole et al. |
| 10,466,327 B2 | 11/2019 | Rothberg et al. |
| 10,488,482 B2 | 11/2019 | Rearick et al. |
| 10,495,712 B2 | 12/2019 | Rothberg et al. |
| 10,520,566 B2 | 12/2019 | Poole et al. |
| 10,527,692 B2 | 1/2020 | McNulty et al. |
| 10,527,699 B1 | 1/2020 | Cheng et al. |
| 10,534,058 B2 | 1/2020 | Sofka et al. |
| 10,534,059 B2 | 1/2020 | Rich et al. |
| 10,539,637 B2 | 1/2020 | Poole et al. |
| 10,545,207 B2 | 1/2020 | Poole et al. |
| 10,551,452 B2 | 2/2020 | Rearick et al. |
| 10,551,458 B2 | 2/2020 | Tan et al. |
| 10,564,239 B2 | 2/2020 | Poole et al. |
| 10,588,587 B2 | 3/2020 | Samsonov et al. |
| 10,591,561 B2 | 3/2020 | Sacolick et al. |
| 10,591,567 B2 | 3/2020 | Saito et al. |
| 10,605,878 B2 | 3/2020 | Otazo et al. |
| 10,635,943 B1 | 4/2020 | Lebel et al. |
| 10,650,532 B2 | 5/2020 | Gerganov et al. |
| 10,663,551 B2 | 5/2020 | Arunachalam |
| 10,667,691 B2 | 6/2020 | Lee et al. |
| 10,705,170 B1 | 7/2020 | Wu et al. |
| 10,709,387 B2 | 7/2020 | Poole et al. |
| 10,712,416 B1 | 7/2020 | Sandino et al. |
| 10,748,309 B2 | 8/2020 | Seevinck |
| 10,775,469 B2 | 9/2020 | Tsuruyama et al. |
| 10,803,354 B2 | 10/2020 | Zhao et al. |
| 10,803,631 B2 | 10/2020 | Li et al. |
| 10,831,997 B2 | 11/2020 | Lin |
| 10,950,014 B2 | 3/2021 | Wheaton et al. |
| 11,137,462 B2 | 10/2021 | Shapiro et al. |
| 11,185,249 B2 | 11/2021 | Schlemper et al. |
| 11,250,543 B2 | 2/2022 | Huang |
| 11,300,645 B2 | 4/2022 | Schlemper et al. |
| 11,324,418 B2 | 5/2022 | Schlemper et al. |
| 11,344,219 B2 | 5/2022 | Schlemper et al. |
| 11,346,911 B2 | 5/2022 | Daval Frerot et al. |
| 11,417,423 B2 | 8/2022 | Chen et al. |
| 11,543,481 B2 | 1/2023 | Murphy et al. |
| 11,564,590 B2 | 1/2023 | Schlemper et al. |
| 11,681,000 B2 | 6/2023 | Schlemper et al. |
| 2003/0194124 A1 | 10/2003 | Suzuki et al. |
| 2007/0087756 A1 | 4/2007 | Hoffberg |
| 2007/0249928 A1 | 10/2007 | Blezek et al. |
| 2013/0322723 A1 | 12/2013 | Akhbardeh et al. |
| 2014/0103929 A1 | 4/2014 | Liu |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0093048 A1 | 3/2016 | Cheng et al. |
| 2016/0128592 A1 | 5/2016 | Rosen et al. |
| 2016/0131727 A1 | 5/2016 | Sacolick et al. |

(56) References Cited

U.S. PATENT DOCUMENTS

| | | |
|---|---|---|
| 2016/0169992 A1 | 6/2016 | Rothberg et al. |
| 2016/0169993 A1 | 6/2016 | Rearick et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0275678 A1 | 9/2016 | Onal et al. |
| 2016/0299203 A1 | 10/2016 | Mileski et al. |
| 2016/0334479 A1 | 11/2016 | Poole et al. |
| 2017/0072222 A1 | 3/2017 | Siversson |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2018/0012354 A1 | 1/2018 | Fisher |
| 2018/0018757 A1 | 1/2018 | Suzuki |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0189930 A1* | 7/2018 | Dannels .......... G01R 33/56545 |
| 2018/0197317 A1 | 7/2018 | Cheng et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2018/0240219 A1 | 8/2018 | Mentl et al. |
| 2018/0285695 A1 | 10/2018 | Guo et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0035116 A1 | 1/2019 | Xing et al. |
| 2019/0038233 A1 | 2/2019 | Poole et al. |
| 2019/0086497 A1 | 3/2019 | Rearick et al. |
| 2019/0101605 A1 | 4/2019 | Hyun et al. |
| 2019/0101607 A1 | 4/2019 | Rothberg et al. |
| 2019/0128989 A1 | 5/2019 | Braun et al. |
| 2019/0162806 A1 | 5/2019 | Poole et al. |
| 2019/0172230 A1 | 6/2019 | Mailhe et al. |
| 2019/0178962 A1 | 6/2019 | Poole et al. |
| 2019/0178963 A1 | 6/2019 | Poole et al. |
| 2019/0205766 A1 | 7/2019 | Krebs et al. |
| 2019/0227136 A1 | 7/2019 | Mileski et al. |
| 2019/0227137 A1 | 7/2019 | Mileski et al. |
| 2019/0236817 A1 | 8/2019 | Cheng et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0266761 A1 | 8/2019 | Malkiel et al. |
| 2019/0279361 A1 | 9/2019 | Meyer et al. |
| 2019/0282205 A1 | 9/2019 | Tung |
| 2019/0295294 A1 | 9/2019 | Fournie |
| 2019/0311267 A1 | 10/2019 | Qin et al. |
| 2019/0324098 A1 | 10/2019 | McNulty et al. |
| 2019/0340793 A1 | 11/2019 | Jin et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2019/0353741 A1 | 11/2019 | Bolster, Jr. et al. |
| 2019/0362522 A1 | 11/2019 | Han |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0041597 A1 | 2/2020 | Daval Frerot et al. |
| 2020/0045112 A1 | 2/2020 | Sacolick et al. |
| 2020/0058106 A1 | 2/2020 | Lazarus et al. |
| 2020/0090382 A1 | 3/2020 | Huang et al. |
| 2020/0103483 A1 | 4/2020 | Hardy et al. |
| 2020/0118306 A1 | 4/2020 | Ye et al. |
| 2020/0146635 A1 | 5/2020 | Wang et al. |
| 2020/0175675 A1 | 6/2020 | Ogino et al. |
| 2020/0200844 A1 | 6/2020 | Boskamp et al. |
| 2020/0209334 A1 | 7/2020 | O'Halloran et al. |
| 2020/0249300 A1 | 8/2020 | Sandino et al. |
| 2020/0273215 A1 | 8/2020 | Wang et al. |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0334871 A1 | 10/2020 | Su et al. |
| 2020/0337587 A1 | 10/2020 | Sacolick et al. |
| 2020/0337591 A1 | 10/2020 | Rotman et al. |
| 2020/0341094 A1 | 10/2020 | Polak et al. |
| 2020/0341100 A1 | 10/2020 | Heukensfeldt Jansen et al. |
| 2020/0341103 A1 | 10/2020 | Akcakaya et al. |
| 2020/0355765 A1 | 11/2020 | Chen et al. |
| 2020/0355774 A1 | 11/2020 | Wang et al. |
| 2021/0003651 A1 | 1/2021 | Kamiguchi |
| 2021/0027436 A1 | 1/2021 | Banerjee et al. |
| 2021/0077060 A1 | 3/2021 | Kim |
| 2021/0090306 A1 | 3/2021 | Akcakaya et al. |
| 2021/0106251 A1 | 4/2021 | Lips et al. |
| 2021/0145393 A1 | 5/2021 | Gao et al. |
| 2021/0177296 A1 | 6/2021 | Saalbach et al. |
| 2021/0181287 A1 | 6/2021 | Sommer et al. |
| 2021/0272240 A1 | 9/2021 | Litwiller et al. |
| 2022/0015662 A1 | 1/2022 | Schlemper et al. |
| 2022/0354378 A1 | 11/2022 | Nacev et al. |
| 2024/0168105 A1 | 5/2024 | Inglis et al. |

FOREIGN PATENT DOCUMENTS

| | | |
|---|---|---|
| CN | 108335339 A | 7/2018 |
| CN | 108376387 A | 8/2018 |
| EP | 2194392 A1 | 6/2010 |
| EP | 3467766 A1 | 4/2019 |
| JP | H07-178072 A | 7/1995 |
| WO | WO-2016/161120 A1 | 10/2016 |
| WO | WO-2017/083849 A1 | 5/2017 |
| WO | WO 2018/045274 A1 | 3/2018 |
| WO | WO-2018/094033 A1 | 5/2018 |
| WO | WO 2018/187005 A1 | 10/2018 |
| WO | WO-2019/099986 A1 | 5/2019 |

OTHER PUBLICATIONS

Lustig, Michael, and John M. Pauly. "SPIRiT: iterative self-consistent parallel imaging reconstruction from arbitrary k-space." Magnetic resonance in medicine 64.2 (2010): 457-471. (Year: 2010).*

Lin, Jyh-Miin. "Python Non-Uniform Fast Fourier Transform (PyNUFFT): multi-dimensional non-Cartesian image reconstruction package for heterogeneous platforms and applications to MRI." arXiv preprint arXiv:1710.03197 (2017). (Year: 2017).*

(56) References Cited

OTHER PUBLICATIONS

Jin, Kyong Hwan, et al. "Deep convolutional neural network for inverse problems in imaging." IEEE Transactions on Image Processing 26.9 (2017): 4509-4522. (Year: 2017).*

Moresi, Giorgio, and Richard Magin. "Miniature permanent magnet for table-top NMR." Concepts in Magnetic Resonance Part B: Magnetic Resonance Engineering: An Educational Journal 19.1 (2003): 35-43. (Year: 2003).*

International Search Report and Written Opinion for International Application No. PCT/US2019/046649 mailed Nov. 12, 2019.

Invitation to Pay Additional Fees for International Application No. PCT/US2019/043927 mailed Nov. 22, 2019.

International Search Report and Written Opinion for International Application No. PCT/US2019/043927 mailed Jan. 28, 2020.

Invitation to Pay Additional Fees for International Application No. PCT/US2020/022306 mailed Jul. 3, 2020.

International Search Report and Written Opinion for International Application No. PCT/US2020/022306 mailed Oct. 2, 2020.

International Preliminary Report on Patentability for International Application No. PCT/US2019/043927 dated Feb. 11, 2021.

International Preliminary Report on Patentability for International Application No. PCT/US2019/046649 mailed Feb. 25, 2021.

International Preliminary Report on Patentability for International Application No. PCT/US2020/022306 mailed Sep. 23, 2021.

Akcakaya et al., Utility of respiratory-navigator-rejected k-space lines for improved signal-to-noise ratio in three-dimensional cardiac MR. Magnetic resonance in medicine. Nov. 2013;70(5):1332-9.

Caballero et al., Application-driven MRI: Joint reconstruction and segmentation from undersampled MRI data. International Conference on Medical Image Computing and Computer-Assisted Intervention Sep. 14, 2014:106-113.

Caballero et al., Dictionary learning and time sparsity for dynamic MR data reconstruction. IEEE transactions on medical imaging. Jan. 17, 2014;33(4):979-94.

Campbell-Washburn et al., Using the robust principal component analysis algorithm to remove RF spike artifacts from MR images. Magnetic resonance in medicine. Jun. 2016;75(6):2517-25.

Cordero-Grande et al., Three-dimensional motion corrected sensitivity encoding reconstruction for multi-shot multi-slice MRI: application to neonatal brain imaging. Magnetic resonance in medicine. Mar. 2018;79(3):1365-76.

Delattre et al., Spiral demystified. Magnetic resonance imaging. Jul. 1, 2010;28(6):862-81.

Eo et al., KIKI-net: cross-domain convolutional neural networks for reconstructing undersampled magnetic resonance images. Magnetic resonance in medicine. Nov. 2018;80(5):2188-201.

Eo et al., Supporting Information—KIKI-net: cross-domain convolutional neural networks for reconstructing undersampled magnetic resonance images. Magnetic resonance in medicine. Nov. 2018: 14 pages.

Fessler et al., Nonuniform fast Fourier transforms using min-max interpolation. IEEE transactions on signal processing. Jan. 22, 2003;51(2):560-74.

Fessler, Model-based image reconstruction for MRI. IEEE Signal Processing Magazine. Jul. 1, 2010;27(4):81-9.

Fessler, On NUFFT-based gridding for non-Cartesian MRI. Journal of Magnetic Resonance. Oct. 1, 2007;188(2):191-5.

Forbes et al., Propeller MRI: clinical testing of a novel technique for quantification and compensation of head motion. Journal of Magnetic Resonance Imaging: An Official Journal of the International Society for Magnetic Resonance in Medicine. Sep. 2001;14(3):215-22.

Gal et al., Dropout as a bayesian approximation: Representing model uncertainty in deep learning. International conference on machine learning. Jun. 11, 2016:1050-1059.

Graham et al., A supervised learning approach for diffusion MRI quality control with minimal training data. NeuroImage. Sep. 1, 2018;178:668-76.

Greengard et al., Accelerating the nonuniform fast Fourier transform. SIAM review. 2004;46(3):443-54.

Griswold et al., Generalized autocalibrating partially parallel acquisitions (GRAPPA). Magnetic Resonance in Medicine: An Official Journal of the International Society for Magnetic Resonance in Medicine. Jun. 2002;47(6):1202-10.

Hammernik et al., Learning a variational network for reconstruction of accelerated MRI data. Magnetic resonance in medicine. Jun. 2018;79(6):3055-71.

Han et al., Deep learning with domain adaptation for accelerated projection-reconstruction MR. Magnetic resonance in medicine. Sep. 2018;80(3):1189-205.

Han et al., k-space deep learning for accelerated MRI. arXiv preprint arXiv:1805.03779. May 10, 2018;1;11 pages.

He et al., Deep residual learning for image recognition. InProceedings of the IEEE conference on computer vision and pattern recognition 2016:770-778.

Hu et al., Squeeze-and-excitation networks. Proceedings of the IEEE conference on computer vision and pattern recognition 2018:7132-7141.

Huang et al.,. Densely connected convolutional networks. Proceedings of the IEEE conference on computer vision and pattern recognition 2017:4700-4708.

Jaderberg et al., Spatial transformer networks. Advances in neural information processing systems. 2015:1-9.

Jin et al., A general framework for compressed sensing and parallel MRI using annihilating filter based low-rank Hankel matrix. arXiv preprint arXiv:1504.00532. Dec. 30, 2015;4:32 pages.

Jin et al., Deep convolutional neural network for inverse problems in imaging. IEEE Transactions on Image Processing. Jun. 15, 2017;26(9):4509-22.

Khalel, Edafa. GitHub. Nov. 26, 2018:3 pages. https://github.com/andrewekhalel/edafa/blob/master/README.md [last accessed Mar. 25, 2020].

Kingma et al., Adam: A method for stochastic optimization. arXiv preprint arXiv:1412.6980. Dec. 22, 2014;1:9 pages.

Knoll et al., Adapted random sampling patterns for accelerated MRI. Magnetic resonance materials in physics, biology and medicine. Feb. 1, 2011;24(1):43-50.

Knoll et al., Second order total generalized variation (TGV) for MRI. Magnetic resonance in medicine. Feb. 2011;65(2):480-91.

Lazarus et al., Sparkling: variable-density k-space filling curves for accelerated T2*-weighted MRI. Magnetic resonance in medicine. Jun. 2019;81(6):3643-61.

Lee et al., 18: An Overview of Deep Learning building blocks, Lecturer: Maruan A1-Shedivat Scribes. XP055641812. May 1, 2017:8 pages.

Lee et al., Acceleration of MR parameter mapping using annihilating filter-based low rank hankel matrix (ALOHA). Magnetic resonance in medicine. Dec. 2016;76(6):1848-64.

Lee et al., Deep residual learning for accelerated MRI using magnitude and phase networks. IEEE Transactions on Biomedical Engineering. Apr. 2, 2018;65(9):1985-95.

Lin, Python Non-Uniform Fast Fourier Transform (PyNUFFT): multi-dimensional non-Cartesian image reconstruction package for heterogeneous platforms and applications to MRI. Journal of Imaging. MDPI. Mar. 2018;4(51):22 pages.

Lundervold et al., An overview of deep learning in medical imaging focusing on MRI. Zeitschrift für Medizinische Physik. May 1, 2019;29(2):102-27.

Lustig et al., Compressed sensing MRI. IEEE signal processing magazine. Mar. 21, 2008;25(2):72-82.

Lustig et al., SPIRiT: iterative self-consistent parallel imaging reconstruction from arbitrary k-space. Magnetic resonance in medicine. Aug. 2010;64(2):457-71.

Ma et al., Learning traffic as images: a deep convolutional neural network for large-scale transportation network speed prediction. Sensors. 2017;17(4):818.

Mardani et al., Deep generative adversarial networks for compressed sensing automates MRI. arXiv preprint arXiv:1706.00051. May 31, 2017;1:12 pages.

Moresi et al., Miniature permanent magnet for table-top NMR. Concepts in Magnetic Resonance Part B: Magnetic Resonance Engineering: An Educational Journal. 2003;19(1):35-43.

(56) References Cited

OTHER PUBLICATIONS

Oksuz et al., Detection and correction of cardiac MRI motion artefacts during reconstruction from k-space. arXiv preprint arXiv:1906.05695. Jun. 12, 2019;1:1-8.
Pauly, Gridding & NUFFT for Non-Cartesian Image Reconstruction. Proceedings of the International Society for Magnetic Resonance in Medicine. 2013;21:3 pages.
Pawar et al., Moconet: Motion correction in 3D MPRAGE images using a convolutional neural network approach. arXiv preprint arXiv:1807.10831. Jul. 29, 2018: 20 pages.
Perone et al., Unsupervised domain adaptation for medical imaging segmentation with self-ensembling. NeuroImage. Jul. 1, 2019;194:1-11.
Pipe, Motion correction with Propeller MRI: application to head motion and free-breathing cardiac imaging. Magnetic Resonance in Medicine: An Official Journal of the International Society for Magnetic Resonance in Medicine. Nov. 1999;42(5):963-9.
Pluim et al., Mutual-information-based registration of medical images: a survey. IEEE transactions on medical imaging. Jul. 28, 2003;22(8):986-1004.
Pruessmann et al., SENSE: sensitivity encoding for fast MRI. Magnetic Resonance in Medicine: An Official Journal of the International Society for Magnetic Resonance in Medicine. Nov. 1999;42(5):952-62.
Qin et al., Convolutional recurrent neural networks for dynamic MR image reconstruction. arXiv preprint arXiv:1712.01751. Dec. 5, 2017;1:9 pages.
Salehi et al., Real-time deep registration with geodesic loss for Image-to-Template Rigid Registration. arXiv preprint arXiv:1803.05982. Aug. 18, 2018;4:12 pages.
Schlemper et al., A deep cascade of convolutional neural networks for dynamic MR image reconstruction. IEEE transactions on Medical Imaging. Feb. 2018;37(2):491-503.
Schlemper et al., Cardiac MR segmentation from undersampled k-space using deep latent representation learning. International Conference on Medical Image Computing and Computer-Assisted Intervention Sep. 16, 2018:259-267.
Schlemper et al., Nonuniform Variational Network: Deep Learning for Accelerated Nonuniform MR Image Reconstruction. InInternational Conference on Medical Image Computing and Computer-Assisted Intervention Oct. 13, 2019:57-64.
Sen et al., Compressive image super-resolution. IEEE 2009 Conference Record of the Forty-Third Asilomar Conference on Signals, Systems and Computers. Nov. 1, 2009:1235-1242.
Shi et al., Is the deconvolution layer the same as a convolutional layer? arXiv preprint arXiv:1609.07009. Sep. 22, 2016:8 pages.
Souza et al., A hybrid frequency-domain/image-domain deep network for magnetic resonance image reconstruction. arXiv preprint arXiv:1810.12473. Oct. 30, 2018:1-8.
Tajbakhsh et al., Convolutional neural networks for medical image analysis: Full training or fine tuning? An accepted version of N. arXiv preprint arXiv:1706.0712. Jun. 2, 2017:1-17.
Tamada et al., Method for motion artifact reduction using a convolutional neural network for dynamic contrast enhanced MRI of the liver. arXiv preprint arXiv:1807.06956. Jul. 18, 2018:1-12.
Usman et al., Motion corrected compressed sensing for free-breathing dynamic cardiac MRI. Magnetic resonance in medicine. Aug. 2013;70(2):504-16.
Walsh et al., Adaptive reconstruction of phased array MR imagery. Magnetic Resonance in Medicine: An Official Journal of the International Society for Magnetic Resonance in Medicine. May 2000;43(5):682-90.
Wang et al., Dimension: Dynamic mr imaging with both k-space and spatial prior knowledge obtained via multi-supervised network training. MMR in Biomedicine. arXiv preprint arXiv:1810.00302. Nov. 6, 2018;4:1-13.
Wang et al., Image quality assessment: from error visibility to structural similarity. IEEE transactions on image processing. Apr. 13, 2004;13(4):600-12.
Yang et al., DAGAN: Deep de-aliasing generative adversarial networks for fast compressed sensing MRI reconstruction. IEEE transactions on medical imaging. Jun. 2018;37(6):1310-21.
Zhang et al., Coil compression for accelerated imaging with Cartesian sampling. Magnetic resonance in medicine. Feb. 2013;69(2):571-82.
Zhu et al., HENet: A Highly Efficient Convolutional Neural Networks Optimized for Accuracy, Speed and Storage. arXiv preprint arXiv:1803.02742. Mar. 7, 2018:12 pages.
Zhu et al., Image reconstruction by domain-transform manifold learning. Nature. Mar. 2018;555(7697):487.
Communication pursuant to Rule 164(2) and Article 94(3) EPC for EP App. No. 19753529.7 dated Dec. 4, 2023 (10 pages).
Tezcan Kerem C. et al: "MR Image Reconstruction Using Deep Density Priors", IEEE Transactions on Medical Imaging, vol. 38, No. 7, Dec. 19, 2018 (Dec. 19, 2018), pp. 1633-1642, XP093104502, USA ISSN: 0278-0062, DOI: 10.1109/TMI.2018.2887072 Retrieved from the Internet: URL:https://arxiv.org/pdf/1711.11386.pdf.
First Office Action and Search Report for CN App. No. 201980064279.0 dated Jan. 2, 2024 (with English translation, 25 pages).
First Office Action and Search Report for CN App. No. 201980067978.0 dated Jan. 23, 2024 (with English translation, 42 pages).
Taohui, et al., "Fast magnetic resonance imaging with deep learning and design of undersampling trajectory," Chinese Journal of Image and Graphics, 23(2), Feb. 16, 2018 (Only English Abstract Available).

* cited by examiner

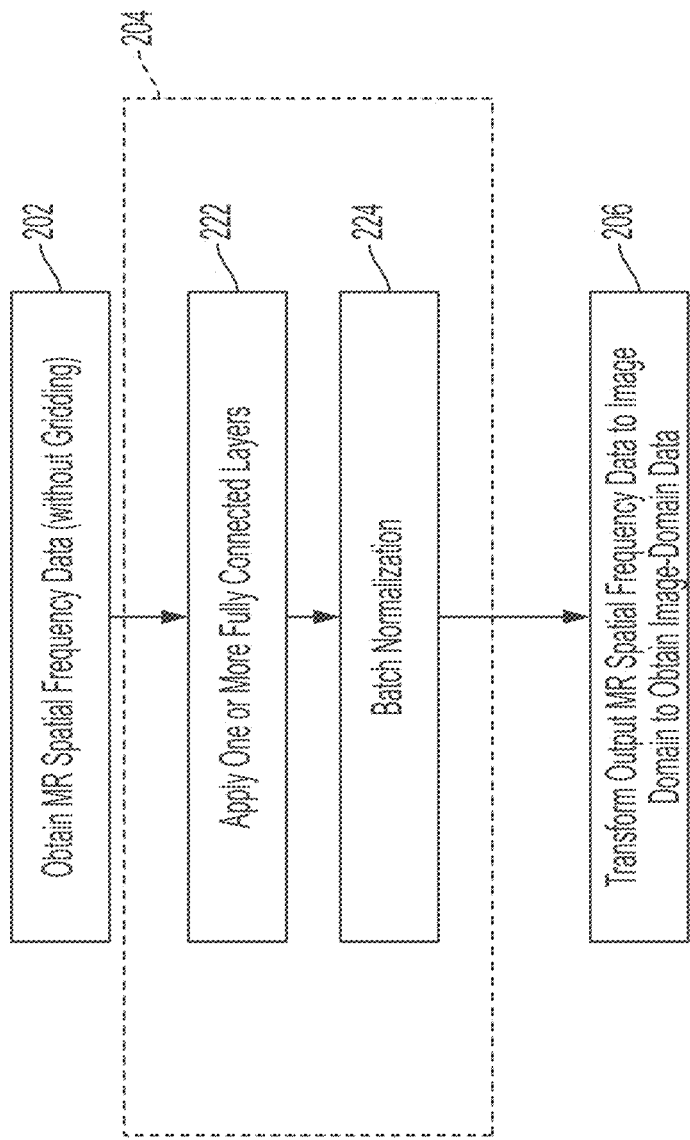

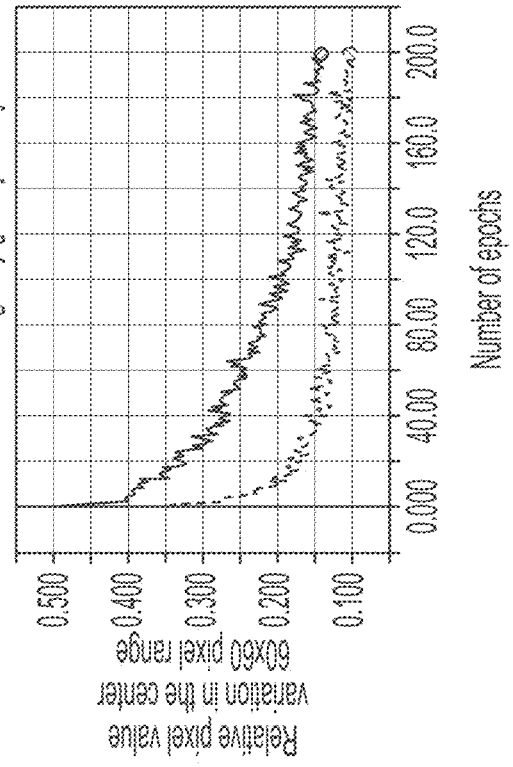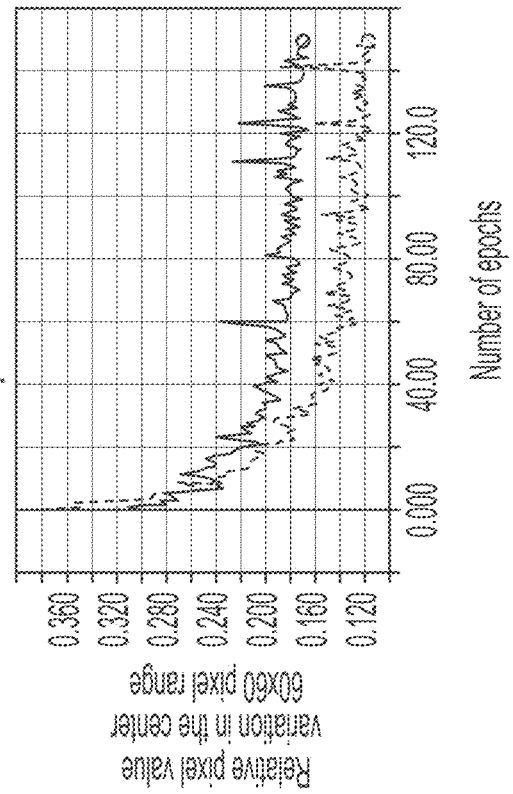
FIG. 4

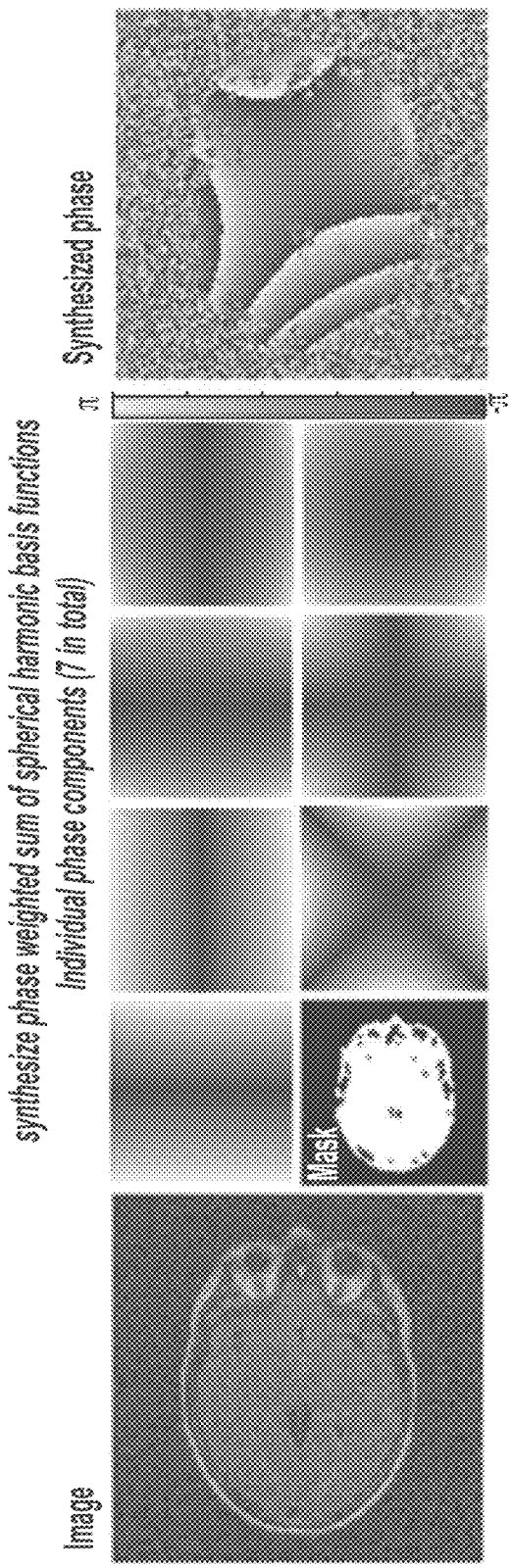
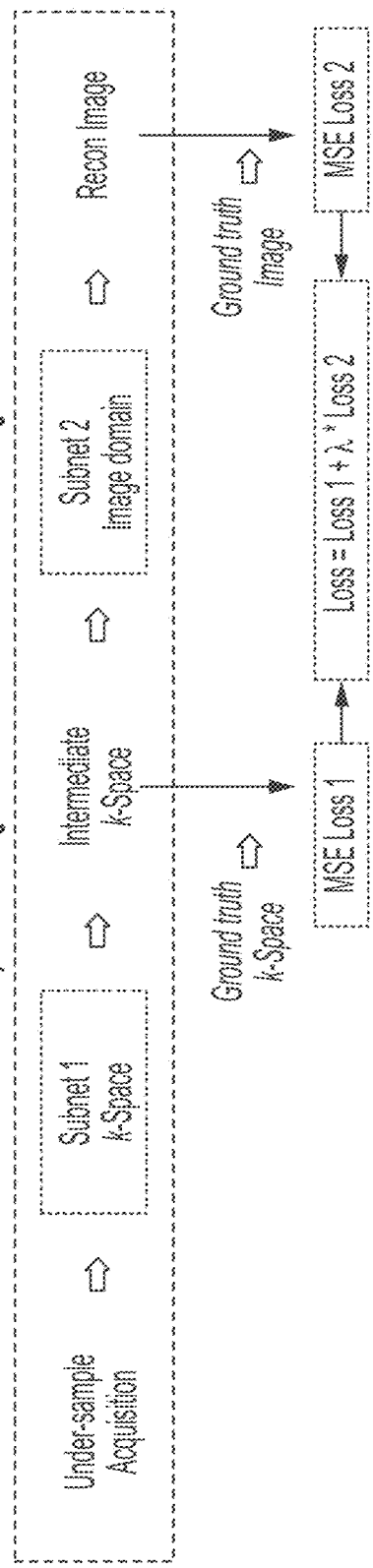
FIG. 9A
FIG. 9B

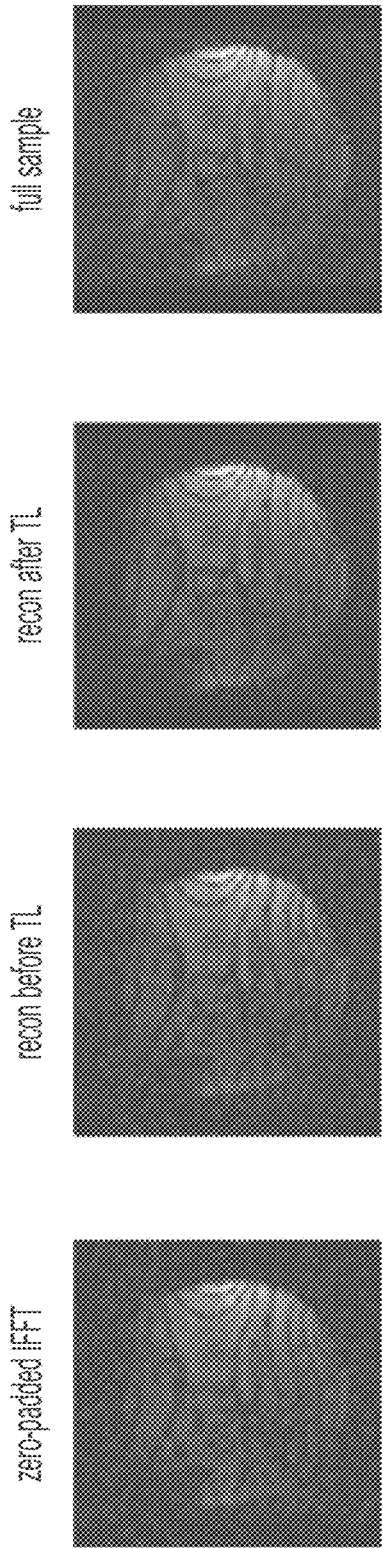
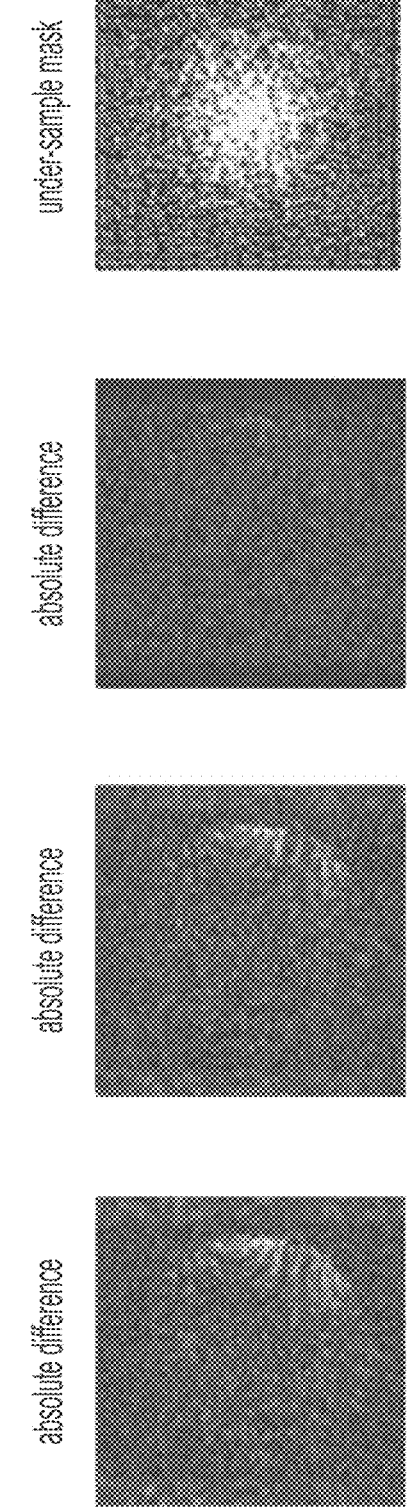

DEEP LEARNING TECHNIQUES FOR MAGNETIC RESONANCE IMAGE RECONSTRUCTION

CROSS-REFERENCE TO RELATED APPLICATIONS

This application claims priority under 35 U.S.C. § 120 and is a continuation of U.S. patent application Ser. No. 16/524,638, filed Jul. 29, 2019, and titled "DEEP LEARNING TECHNIQUES FOR MAGNETIC RESONANCE IMAGE RECONSTRUCTION", which claims priority under 35 U.S.C. § 119 (e) to U.S. Provisional Application Ser. No. 62/711,895, filed Jul. 30, 2018, and titled "DEEP LEARNING TECHNIQUES FOR MAGNETIC RESONANCE IMAGE RECONSTRUCTION", U.S. Provisional Application Ser. No. 62/737,524, filed Sep. 27, 2018, and titled "DEEP LEARNING TECHNIQUES FOR MAGNETIC RESONANCE IMAGE RECONSTRUCTION", U.S. Provisional Application Ser. No. 62/744,529, filed Oct. 11, 2018, and titled "DEEP LEARNING TECHNIQUES FOR MAGNETIC RESONANCE IMAGE RECONSTRUCTION", and U.S. Provisional Application Ser. No. 62/820,119, filed Mar. 18, 2019, and titled "END-TO-END LEARNABLE MR IMAGE RECONSTRUCTION", each of which is incorporated by reference in its entirety.

BACKGROUND

Magnet resonance imaging (MRI) provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to its ability to produce non-invasive images having relatively high resolution and contrast without the safety concerns of other modalities (e.g., without needing to expose the subject to ionizing radiation, such as x-rays, or introducing radioactive material into the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to conventional MRI techniques that, for a given imaging application, may include the relatively high cost of the equipment, limited availability (e.g., difficulty and expense in gaining access to clinical MRI scanners), and the length of the image acquisition process.

To increase imaging quality, the trend in clinical and research MRI has been to increase the field strength of MRI scanners to improve one or more specifications of scan time, image resolution, and image contrast, which in turn drives up costs of MRI imaging. The vast majority of installed MRI scanners operate using at least at 1.5 or 3 tesla (T), which refers to the field strength of the main magnetic field B0 of the scanner. A rough cost estimate for a clinical MRI scanner is on the order of one million dollars per tesla, which does not even factor in the substantial operation, service, and maintenance costs involved in operating such MRI scanners. Additionally, conventional high-field MRI systems typically require large superconducting magnets and associated electronics to generate a strong uniform static magnetic field (B0) in which a subject (e.g., a patient) is imaged. Superconducting magnets further require cryogenic equipment to keep the conductors in a superconducting state. The size of such systems is considerable with a typical MRI installment including multiple rooms for the magnetic components, electronics, thermal management system, and control console areas, including a specially shielded room to isolate the magnetic components of the MRI system. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but is impractical or impossible due to the above-described limitations and as described in further detail below.

SUMMARY

Some embodiments are directed to a method comprising: generating a magnetic resonance (MR) image from input MR spatial frequency data using a neural network model that comprises: a first neural network sub-model configured to process spatial frequency domain data; and a second neural network sub-model configured to process image domain data.

Some embodiments are directly to a system, comprising at least one computer hardware processor; and at least one non-transitory computer-readable storage medium storing processor-executable instructions that, when executed by the at least one computer hardware processor, cause the at least one computer hardware processor to perform: generating a magnetic resonance (MR) image from MR spatial frequency data using a neural network model. The neural network includes that comprises: a first neural network portion configured to process data in a spatial frequency domain; and a second neural network portion configured to process data in an image domain.

Some embodiments are directed to at least one non-transitory computer-readable storage medium storing processor-executable instructions that, when executed by at least one computer hardware processor, cause the at least one computer hardware processor to perform: generating a magnetic resonance (MR) image from MR spatial frequency data using a neural network model. The neural network model comprises a first neural network portion configured to process data in a spatial frequency domain; and a second neural network portion configured to process data in an image domain.

Some embodiments are directed to a method, comprising: generating a magnetic resonance (MR) image from input MR spatial frequency data using a neural network model that comprises a neural network sub-model configured to process spatial frequency domain data and having a locally connected neural network layer.

Some embodiments are directed to a system comprising: at least one processor; at least one non-transitory computer-readable storage medium storing processor-executable instructions that, when executed, cause the at least one processor to perform: generating a magnetic resonance (MR) image from input MR spatial frequency data using a neural network model that comprises a neural network sub-model configured to process spatial frequency domain data and having a locally connected neural network layer.

At least one non-transitory computer-readable storage medium storing processor-executable instructions that, when executed, cause the at least one processor to perform: generating a magnetic resonance (MR) image from input MR spatial frequency data using a neural network model that comprises a neural network sub-model configured to process spatial frequency domain data and having a locally connected neural network layer.

Some embodiments provide for at least one non-transitory computer-readable storage medium storing processor-executable instructions that, when executed by at least one computer hardware processor, cause the at least one computer hardware processor to perform a method comprising: generating a magnetic resonance (MR) image from input MR spatial frequency data using a neural network model comprising one or more neural network blocks including a first neural network block, wherein the first neural network block is configured to perform data consistency processing using a non-uniform Fourier transformation for transforming image domain data to spatial frequency domain data.

Some embodiments provide for a magnetic resonance imaging (MRI) system, comprising: a magnetics system comprising: a $B_0$ magnet configured to provide a $B_0$ field for the MRI system; gradient coils configured to provide gradient fields for the MRI system; and at least one RF coil configured to detect magnetic resonance (MR) signals; a controller configured to: control the magnetics system to acquire MR spatial frequency data; generate an MR image from MR spatial frequency data using a neural network model that comprises: a first neural network portion configured to process data in a spatial frequency domain; and a second neural network portion configured to process data in an image domain.

Some embodiments a magnetic resonance imaging (MRI) system, comprising: a magnetics system comprising: a $B_0$ magnet configured to provide a $B_0$ field for the MRI system; gradient coils configured to provide gradient fields for the MRI system; and at least one RF coil configured to detect magnetic resonance (MR) signals; a controller configured to: control the magnetics system to acquire MR spatial frequency data; generate an MR image from input MR spatial frequency data using a neural network model that comprises a neural network sub-model configured to process spatial frequency domain data and having a locally connected neural network layer.

Some embodiments provide for a method, comprising: generating a magnetic resonance (MR) image from input MR spatial frequency data using a neural network model comprising one or more neural network blocks including a first neural network block, wherein the first neural network block is configured to perform data consistency processing using a non-uniform Fourier transformation for transforming image domain data to spatial frequency domain data.

Some embodiments provide for a system, comprising: at least one computer hardware processor; and at least one non-transitory computer-readable storage medium storing processor-executable instructions that, when executed by the at least one computer hardware processor, cause the at least one computer hardware processor to perform a method comprising: generating a magnetic resonance (MR) image from input MR spatial frequency data using a neural network model comprising one or more neural network blocks including a first neural network block, wherein the first neural network block is configured to perform data consistency processing using a non-uniform Fourier transformation for transforming image domain data to spatial frequency domain data.

Some embodiments provide for a magnetic resonance imaging (MRI) system, comprising: a magnetics system comprising: a $B_0$ magnet configured to provide a $B_0$ field for the MRI system; gradient coils configured to provide gradient fields for the MRI system; and at least one RF coil configured to detect magnetic resonance (MR) signals; a controller configured to: control the magnetics system to acquire MR spatial frequency data using a non-Cartesian sampling trajectory; and generate an MR image from the acquired MR spatial frequency data using a neural network model comprising one or more neural network blocks including a first neural network block, wherein the first neural network block is configured to perform data consistency processing using a non-uniform Fourier transformation.

The foregoing is a non-limiting summary of the invention, which is defined by the attached claims.

BRIEF DESCRIPTION OF THE DRAWINGS

Various aspects and embodiments of the disclosed technology will be described with reference to the following figures. It should be appreciated that the figures are not necessarily drawn to scale.

FIG. 2C is a flowchart of an illustrative process for processing spatial frequency domain data, which may be part of the illustrative process 200, to generate an MR image, in accordance with some embodiments of the technology described herein.

FIG. 4 illustrates the performance of the techniques described herein for generating an MR image from input MR spatial frequency data using different embodiments of the neural network model described herein.

FIG. 9A illustrates aspects of generating synthetic complex-valued images for training a neural network model for generating MR images from under-sampled spatial frequency domain data, in accordance with some embodiments of the technology described herein.

FIG. 9B illustrates a loss function, having spatial frequency and image domain components, which may be used for training a neural network model for generating MR images from under-sampled spatial frequency domain data, in accordance with some embodiments of the technology described herein.

FIGS. 10A-10H illustrate reconstructed MR images using a zero-padded inverse discrete Fourier transform (DFT) and using neural network models, trained with and without transfer learning, in accordance with some embodiments of the technology described herein.

DETAILED DESCRIPTION

Figure 1A:
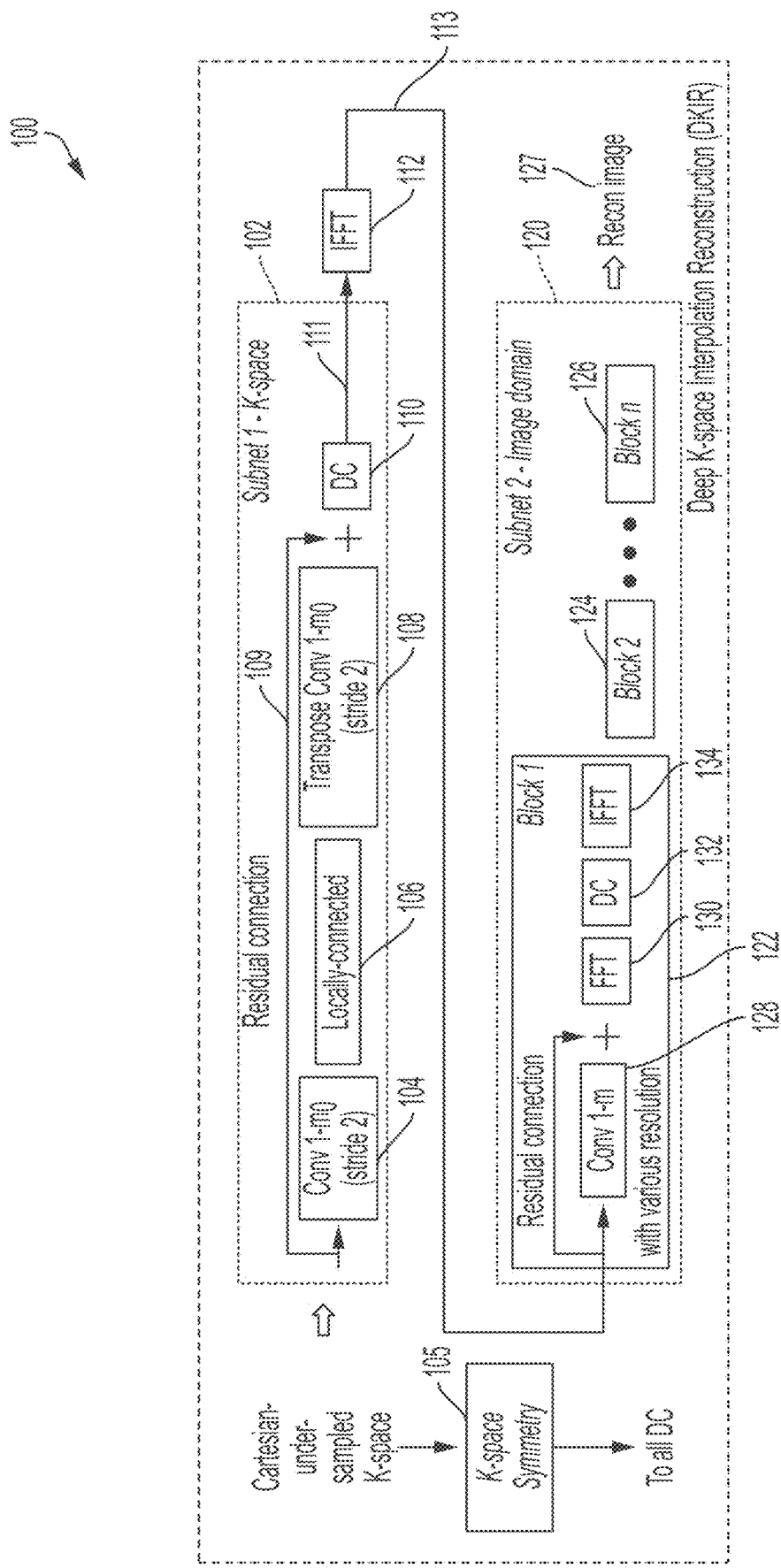
FIG. 1A illustrates the architecture of an example neural network model for generating a magnetic resonance (MR) image from input MR spatial frequency data, in accordance with some embodiments of the technology described herein.

Conventional magnetic resonance imaging techniques require a time-consuming MRI scan for a patient in a tight chamber in order to obtain high-resolution cross-sectional images of the patient's anatomy. Long scan duration limits the number of patients that can be scanned with MR scanners, causes patient discomfort, and increases the cost of scanning. The inventors have developed techniques for generating medically-relevant, clinically-accepted MRI images from shorter-duration MRI scans, thereby improving conventional MRI technology.

The duration of an MRI scan is proportional to the number of data points acquired in the spatial frequency domain (sometimes termed "k-space"). Accordingly, one way of reducing the duration of the scan is to acquire fewer data points. For example, fewer samples may be acquired in the frequency encoding direction, the phase encoding direction, or both the frequency and phase encoding directions. However, when fewer data points are obtained than what is required by the spatial Nyquist criteria (this is often termed "under-sampling" k-space), the MR image generated from the collected data points by an inverse Fourier transform contains artifacts due to aliasing. As a result, although scanning time is reduced by under-sampling in the spatial frequency domain, the resulting MRI images have poor quality and may be unusable, as the introduced artifacts may severely degrade image quality, fidelity, and interpretability.

Conventional techniques for reconstructing MR images from under-sampled k-space data also suffer from drawbacks. For example, compressed sensing techniques have been applied to the problem of generating an MR image from under-sampled spatial frequency data by using a randomized k-space under-sampling trajectory that creates incoherent aliasing, which in turn is eliminated using an iterative image reconstruction process. However, the iterative reconstruction techniques require a large amount of computational resources, do not work well without extensive empirical parameter tuning, and often result in a lower-resolution MR image with lost details.

Deep learning techniques have also been used for reconstructing MR images from under-sampled k-space data. The neural network parameters underlying such techniques may be estimated using fully-sampled data (data collected by sampling spatial frequency space so that the Nyquist criterion is not violated) and, although training such models may be time-consuming, the trained models may be applied in real-time during acquisition because the neural network-based approach to image reconstruction is significantly more computationally efficient than the iterative reconstruction techniques utilized in the compressive sensing context.

The inventors have recognized that conventional deep learning MR image reconstruction techniques may be improved upon. For example, conventional deep learning MR image reconstruction techniques operate either purely in the image domain or in the spatial frequency domain and, as such, fail to take into account correlation structure both in the spatial frequency domain and in the image domain. As another example, none of the conventional deep learning MR image reconstruction techniques (nor the compressed sensing techniques described above) work with non-Cartesian (e.g., radial, spiral, rosette, variable density, Lissajou, etc.) sampling trajectories, which are commonly used to accelerate MRI acquisition and are also robust to motion by the subject. By contrast, the inventors have developed novel deep learning techniques for generating high-quality MR images from under-sampled spatial frequency data that: (1) operate both in the spatial frequency domain and in the image domain; and (2) enable reconstruction of MR images from non-Cartesian sampling trajectories. As described herein, the deep learning techniques developed by the inventors improve upon conventional MR image reconstruction techniques (including both compressed sensing and deep learning techniques) and improve MR scanning technology by reducing the duration of scans while generating high quality MR images.

Some embodiments described herein address all of the above-described issues that the inventors have recognized with conventional techniques for generating MR images from under-sampled spatial frequency domain data. However, not every embodiment described below addresses every one of these issues, and some embodiments may not address any of them. As such, it should be appreciated that embodiments of the technology provided herein are not limited to addressing all or any of the above-described issues of conventional techniques for generating MR images from under-sampled spatial frequency domain data.

Accordingly, some embodiments provide for a method of generating an MR image from under-sampled spatial frequency domain data, the method comprising generating a magnetic resonance (MR) image from input MR spatial frequency data using a neural network model that comprises: (1) a first neural network sub-model configured to process spatial frequency domain data; and (2) a second neural network sub-model configured to process image domain data. In this way, the techniques described herein operate both in the spatial-frequency and image domains.

In some embodiments, the first neural network sub-model is applied prior to the second neural network sub-model. In this way, a neural network is applied to spatial-frequency domain data, prior to transforming the spatial-frequency domain data to the image domain, to take advantage of the correlation structure in the spatial frequency domain data. Accordingly, in some embodiments, generating the MR image may include: (1) processing the input. MR spatial frequency data using the first neural network sub-model to obtain output MR spatial frequency data; (2) transforming the output MR spatial frequency data to the image domain to obtain input image-domain data; and (3) processing the input image-domain data using the second neural network sub-model to obtain the MR image.

In some embodiments, the first neural network sub-model may include one or more convolutional layers. In some embodiments, one or more (e.g., all) of the convolutional layers may have a stride greater than one, which may provide for down-sampling of the spatial-frequency data. In some embodiments, the first neural network sub-model may include one or more transposed convolutional layers, which may provide for up-sampling of the spatial frequency data. Additionally or alternatively, the first neural network sub-model may include at least one locally-connected layer, at least one data consistency layer, and/or at least one complex-conjugate symmetry layer. In some embodiments, the locally-connected layer may include a respective set of parameter values for each data point in the MR spatial frequency data.

In some embodiments, the first neural network sub-model includes at least one convolutional layer, a locally-connected layer, and at least one transposed convolutional layer, and processing the input MR spatial frequency data using the first neural network sub-model may include: (1) applying the at least one convolutional layer to the input MR spatial frequency data; (2) applying the locally-connected layer to data obtained using output of the at least one convolutional layer; and (3) applying the at least one transposed convolutional layer to data obtained using output of the locally-connected layer. In such embodiments, the first neural network sub-model may be thought of as having a "U" structure consisting of a down-sampling path (the left arm of the "U"—implemented using a series of convolutional layers one or more of which have a stride greater than one), a locally-connected layer (the bottom of the "U"), and an up-sampling path (the right arm of the "U"—implemented using a series of transposed convolutional layers).

In some embodiments, using a transposed convolutional layer (which is sometimes termed a fractionally sliding convolutional layer or a deconvolutional layer) may lead to checkerboard artifacts in the upsampled output. To address this issue, in some embodiments, upsampling may be performed by a convolutional layer in which the kernel size is divisible by the stride length, which may be thought of a "sub-pixel" convolutional layer. Alternatively, in other embodiments, upsampling to a higher resolution may be performed without relying purely on a convolutional layer to do so. For example, the upsampling may be performed by resizing the input image (e.g., using interpolation such as bilinear interpolation or nearest-neighbor interpolation) and following this operation by a convolutional layer. It should be appreciated that such an approach may be used in any of the embodiments described herein instead of and/or in conjunction with a transposed convolutional layer.

In some embodiments, the first neural network sub-model further takes into account the complex-conjugate symmetry of the spatial frequency data by including a complex-conjugate symmetry layer. In some such embodiments, the complex-conjugate symmetry layer may be applied at the output of the transposed convolutional layers so that processing the input MR spatial frequency data using the first neural network sub-model includes applying the complex-conjugate symmetry layer to data obtained using output of the at least one transposed convolutional layer.

In some embodiments, the first neural network sub-model further includes a data consistency layer to ensure that the application of first neural network sub-model to the spatial frequency data does not alter the values of the spatial frequency data obtained by the MR scanner. In this way, the data consistency layer forces the first neural network sub-model to interpolate missing data from the under-sampled spatial frequency data without perturbing the under-sampled spatial frequency data itself. In some embodiments, the data consistency layer may be applied to the output of the complex-conjugate symmetry layer.

In some embodiments, the first neural network sub-model includes a residual connection. In some embodiments, the first neural network sub-model includes one or more non-linear activation layers. In some embodiments, the first neural network sub-model includes a rectified linear unit activation layer. In some embodiments, the first neural network sub-model includes a leaky rectified linear unit activation layer.

The inventors have also recognized that improved MR image reconstruction may be achieved by generating MR images directly from spatial frequency data samples, without gridding the spatial frequency data, as is often done in conventional MR image reconstruction techniques. In gridding, the obtained spatial frequency data points are mapped to a two-dimensional (2D) Cartesian grid (e.g., the value at each grid point is interpolated from data points within a threshold distance) and a 2D discrete Fourier transform (DFT) is used to reconstruct the image front the grid values. However, such local interpolation introduces reconstruction errors.

The inventors have developed multiple deep-learning techniques for reconstructing MR images from data obtained using non-Cartesian sampling trajectories. Some of the techniques involve using a non-uniform Fourier transformation (e.g., a non-uniform fast Fourier transformation—NuFFT) at each of multiple blocks part of a neural network model in order to promote data consistency with the (ungridded) spatial frequency data obtained by an MRI system. Such data consistency processing may be performed in a number of different ways, though each may make use of the non-uniform Fourier transformation (e.g., as represented by the forward operator A described herein), and the input MR spatial frequency data y. For example, in some embodiments, a non-uniform Fourier transformation may be used in a neural network model block to transform image domain data, which represents the MR reconstruction in the block, to spatial frequency data so that the MR reconstruction in the block may be compared with the spatial frequency data obtained by the MRI system. A neural network model implementing this approach may be termed the non-uniform variational network (NVN) and is described herein including with reference to FIGS. 13A-13D.

As another example, in some embodiments, the non-uniform Fourier transformation may be applied to the spatial frequency data, and the result may be provided as input to each of one or more neural network blocks of a neural network model for reconstructing MR images from spatial frequency data. These innovations provide for a state-of-the art deep learning technique for reconstructing MR images from spatial frequency data obtained using a non-Cartesian sampling trajectory. A neural network model implementing this approach may be termed the generalized non-uniform variational network (GNVN) and is described herein including with reference to FIGS. 13A, 13D, and 13E.

Accordingly, some embodiments provide a method for generating a magnetic resonance (MR) image from input MR spatial frequency data using a neural network model comprising one or more neural network blocks including a first neural network block, wherein the first neural network block is configured to perform data consistency processing using a non-uniform Fourier transformation (e.g., a non-uniform fast Fourier transform—NuFFT) for transforming image domain data to spatial frequency domain data. The MR spatial frequency data may have been obtained using a non-Cartesian sampling trajectory, examples of which are provided herein. In some embodiments, the neural network model may include multiple blocks each of which is configured to perform data consistency processing using the non-uniform Fourier transformation.

In some embodiments, the method for generating the MR image from input MR spatial frequency data includes: obtaining the input MR spatial frequency data; generating an initial image from the input MR spatial frequency data using the non-uniform Fourier transformation; and applying the neural network model to the initial image at least in part by using the first neural network block to perform data consistency processing using the non-uniform Fourier transformation.

In some embodiments, the data consistency processing may involve applying a data consistency block to the data, which may apply a non-uniform Fourier transformation to the data to transform it from the image domain to the spatial frequency domain where it may be compared against the input MR spatial frequency data. In other embodiments, the data consistency processing may involve applying an adjoint non-uniform Fourier transformation to the input MR spatial frequency data and providing the result as the input to each of one or more neural network blocks (e.g., as input to each of one or more convolutional neural network blocks part of the overall neural network model).

In some embodiments, the first neural network block is configured to perform data consistency processing using the non-uniform Fourier transformation at least in part by performing the non-uniform Fourier transformation on data by applying a gridding interpolation transformation, a fast Fourier transformation, and a de-apodization transformation to the data. In this way, the non-uniform Fourier transformation A is represented as a composition of three transformations—a gridding interpolation transformation G, a fast Fourier transformation $F_s$, and a de-apodization transformation D such that $A = G\, F_s\, D$, and applying A to the data may be performed by applying the transformation D, $F_s$, and G, to the data in that order (e.g., as shown in FIG. 13C). The gridding interpolation transformation may be determined based on the non-Cartesian sampling trajectory used to obtain the initial MR input data. In some embodiments, applying the gridding interpolation transformation to the data may be performed using sparse graphical processing unit (GPU) matrix multiplication. Example realizations of these constituent transformations are described herein.

In some embodiments, the neural network model to reconstruct MR images from spatial frequency data may include multiple neural network blocks each of which includes: (1) a data consistency block configured to perform the data consistency processing; and (2) a convolutional neural network block comprising one or more convolutional layers (e.g., having one or more convolutional and/or transpose convolutional layers, having a U-net structure, etc.). Such a neural network model may be termed herein as a non-uniform variational network (NVN).

In some embodiments, the data consistency block is configured to apply the non-uniform Fourier transformation to a first image, provided as input to the data consistency block, to obtain first MR spatial frequency data; and apply an adjoint non-uniform Fourier transformation to a difference between the first MR spatial frequency data and the input MR spatial frequency data. In some embodiments, applying the non-uniform Fourier transformation to the first image domain data comprises: applying, to the first image domain data, a de-apodization transformation followed by a Fourier transformation, and followed by a gridding interpolation transformation.

In some embodiments, applying the first neural network block to image domain data, the applying comprising: applying the data consistency block to image domain data to obtain first output; applying the plurality of convolutional layers to the image domain data to obtain second output; and determining a linear combination of the first and second output.

In some embodiments, the neural network model to reconstruct MR images from spatial frequency data may include multiple neural network blocks each of which includes a plurality of convolutional layers configured to receive as input: (1) image domain data (e.g., representing the networks current reconstruction of the MR data); and (2) output obtained by applying an adjoint non-uniform Fourier transformation to the input MR spatial frequency data. Such a neural network model may be termed herein as a non-uniform variational network (GNVN). In some embodiments, the plurality of convolutional layers is further configured to receive as input: output obtained by applying the non-uniform Fourier transformation and the adjoint non-uniform Fourier transformation to the image domain data.

Another approach developed by the inventors for reconstructing an MR image from input MR spatial frequency data, but without the use of gridding, is to use at least one fully connected layer in the spatial frequency domain. Accordingly, in some embodiments, the first neural network sub-model may include at least one fully connected layer that is to be applied directly to the spatial frequency data points obtained by the scanner. The data points are not mapped to a grid (through gridding and/or any other type of local interpolation) prior to the application of the at least one fully connected layer. In some embodiments, the data points may be irregularly spaced prior to application of the at least one fully connected layer.

In some of the embodiments in which the first neural network sub-model includes a fully-connected layer, the fully connected layer is applied to the real part of the spatial frequency domain data, and the same fully-connected layer is applied to the imaginary part of the spatial frequency domain data. In other words, the data is channelized and the same fully connected layer is applied to both the real and imaginary data channels.

Alternatively, in some of the embodiments in which the first neural network sub-model includes a fully connected layer, the first neural network sub-model includes a first fully-connected layer for applying to the real part of the spatial frequency domain data and a second fully-connected layer for applying to the imaginary part of the spatial frequency domain data. In some embodiments, the first and second fully-connected layers share at least some parameter values (e.g., weights). In some embodiments, the output of the first and second fully-connected layers is transformed using a Fourier transformation (e.g., a two-dimensional inverse discrete Fourier transformation) to obtain image-domain data. In turn, the image-domain data may be provided as input to the second neural network sub-model.

The mention of a 2D Fourier transformation in the preceding paragraph should not, be taken to imply that the techniques described herein are limited to operating on two-dimensional data (e.g., on spatial frequency domain and/or image domain data corresponding to a 2D MR image of a brain "slice"). In some embodiments, the techniques described herein may be applied to 3D data (e.g., spatial frequency domain and/or image domain data corresponding to a stack of 2D MR images of different respective brain slices).

In some embodiments, batch normalization may be applied to the output of fully-connected layer(s) prior to using the Fourier transformation to obtain image-domain data.

In some embodiments, the second neural network sub-model comprises at least one convolutional layer and at least one transposed convolutional layer. In some embodiments, the second neural network sub-model comprises a series of blocks comprising respective sets of neural network layers, each of the plurality of blocks comprising at least one convolutional layer and at least one transposed convolutional layer. In some embodiments, each of the plurality of blocks further comprises: a Fourier transformation layer, a data consistency layer, and an inverse Fourier transformation layer.

In some embodiments, the neural network model used for generating MR images from under-sampled spatial frequency data may be trained using a loss function comprising a spatial frequency domain loss function and an image domain loss function. In some embodiments, the loss function is a weighted sum of the spatial frequency domain loss function and the image domain loss function. In some embodiments, the spatial frequency domain loss function includes mean-squared error.

In some embodiments, the techniques described herein may be used for generating MR images from under-sampled spatial frequency data may be adapted for application to spatial frequency data collected using a low-field MRI system, including, by way of example and not limitation, any of the low-field MR systems described herein and in U.S. Patent Application Publication No. "2018/0164390", titled "ELECTROMAGNETIC SHIELDING FOR MAGNETIC RESONANCE IMAGING METHODS AND APPARATUS," which is incorporated by reference herein in its entirety.

As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

In order to train the neural network models described herein to generate images from (e.g., under-sampled) spatial frequency data obtained by a low-field MRI system, training data obtained using the low-field MRI system is needed. However, there are few low-field MRI scanners on the market and little low-field MRI data available for training such neural network models. To address this limitation, the inventors have developed a novel two-stage training technique for training a neural network model for generating MR images from spatial frequency data obtained by a low-field MRI system. In the first stage, the neural network model (e.g., any of the neural network models described herein having a first and a second neural network sub-model) is trained using a set of images obtained using a "high-field" or a "mid-field" MR system and, subsequently, be adapted by using a set of images obtained using a low-field MRI system.

Following below are more detailed descriptions of various concepts related and embodiments of, methods and apparatus for generating MR images from spatial frequency domain data. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1A illustrates the architecture of an example neural network model for generating a magnetic resonance (MR) image from input MR spatial frequency data, in accordance with some embodiments of the technology described herein. As shown in FIG. 1A, the neural network model 100 comprises first neural network sub-model 102 configured to process spatial frequency domain data, inverse fast Fourier transform (IFFT) layer 112 configured to transform spatial frequency domain data to image domain data, and second neural network sub-model 120 configured to process image domain data. After initial spatial frequency MR data is obtained using an MR scanner (e.g., using any of the low-field MR scanners described herein or any other suitable type of MR scanner), the initial spatial frequency MR data may be processed using the first neural network sub-model 102 to obtain output MR spatial frequency data 111. The MR spatial frequency data 111 is then transformed by LEFT layer 112 to obtain input image-domain data 113, which is processed by second neural network sub-model 120 to obtain an MR image 127.

As shown in FIG. 1A, the first neural network sub-model 102 includes one or more convolutional layers 104, a locally-connected layer 106, one or more transposed convolutional layers 108, a residual connection 109, complex-conjugate symmetry layer 105 and a data consistency layer 110.

When the first neural network sub-model 102 is applied to initial MR spatial frequency data, the initial MR spatial frequency data is first processed by one or more convolutional layers 104, then by locally-connected layer 106, then by transposed convolutional layers 108. In some embodiments the convolutional layer(s) 104 may be used to down-sample the data and the transposed convolutional layers may be used to upsample the data. In such embodiments, these three processing steps may be considered as providing a "U" shaped neural network architecture, with the convolutional layer(s) 104 providing a down-sampling path (left arm of the "U"), the locally-connected layer 106 being at the bottom of the "U", and the transposed convolutional layers 108 providing an up-sampling path (right arm of the "U").

In the illustrated embodiment of FIG. 1A, the convolutional layer(s) 104 include $m_0$ convolutional layers. In some embodiments, m0 may be 1, 2, 3, 4, 5, or any number of layers between 1 and 20 layers. In some embodiments, one or more of the m0 convolutional layers may have a stride greater than or equal to one. In some embodiments, one or more of the m0 convolutional layers has a stride greater than one, which provides for down-sampling or pooling the data through processing by such layers.

In the illustrated embodiment of FIG. 1A, the transposed convolutional layer(s) 108 include $m_0$ transposed convolutional layers. In the illustrated embodiment of FIG. IA, the number of convolutional layer(s) 104 and the number of transposed convolutional layer(s) 108 is the same, but the number of convolutional and transposed convolutional layers may be different in other embodiments.

In some embodiments, the locally-connected layer 106 is provided to exploit local correlation with K-space. In some embodiments, the locally-connected layer 106 is not a convolutional layer (where the same set of weights is applied across different portions of the data), but instead has a respective set of weights for each data point in the spatial frequency domain data. In the illustrated embodiment of FIG. 1A, the locally-connected is placed between the down-sampling and up-samplings paths at the bottom of the "U" structure so that it would have fewer parameters (since the resolution of the data is the lowest at this point), which reduces the number of parameters that have to be learned during training.

In some embodiments, the locally-connected layer may account for energy density variations in the spatial frequency domain (e.g., the center region in the spatial frequency domain has a higher energy density than the peripheral region). In the illustrative embodiment of FIG. 1A, the locally-connected layer 106 operates in the spatial frequency domain and works to interpolate the missing data (due to under-sampling) directly in the spatial frequency domain. In practice, the locally-connected layer, which has far fewer parameters than a fully-connected layer, but more parameters than convolutional layer, provides a good balance between training time and capability to interpolate the missing data points using the local contextual correlation of the spatial frequency domain data.

It should be appreciated that using a locally-connected layer to account for energy density variations in the spatial frequency domain is a novel approach developed by the inventors. Previous approaches split the spatial-frequency domain into three square regions, and the data in each of the three regions was input into a separate model consisting of a stack of convolutional layers (so three separate models for three different square regions). By contrast, using a locally-connected layer does not involve partitioning k space into three square regions, and instead involves assigning independent weights for each sign pixel, which accounts for the various energy density in a more general and flexible manner than previous approaches, resulting in a performance improvement.

Figure 3:
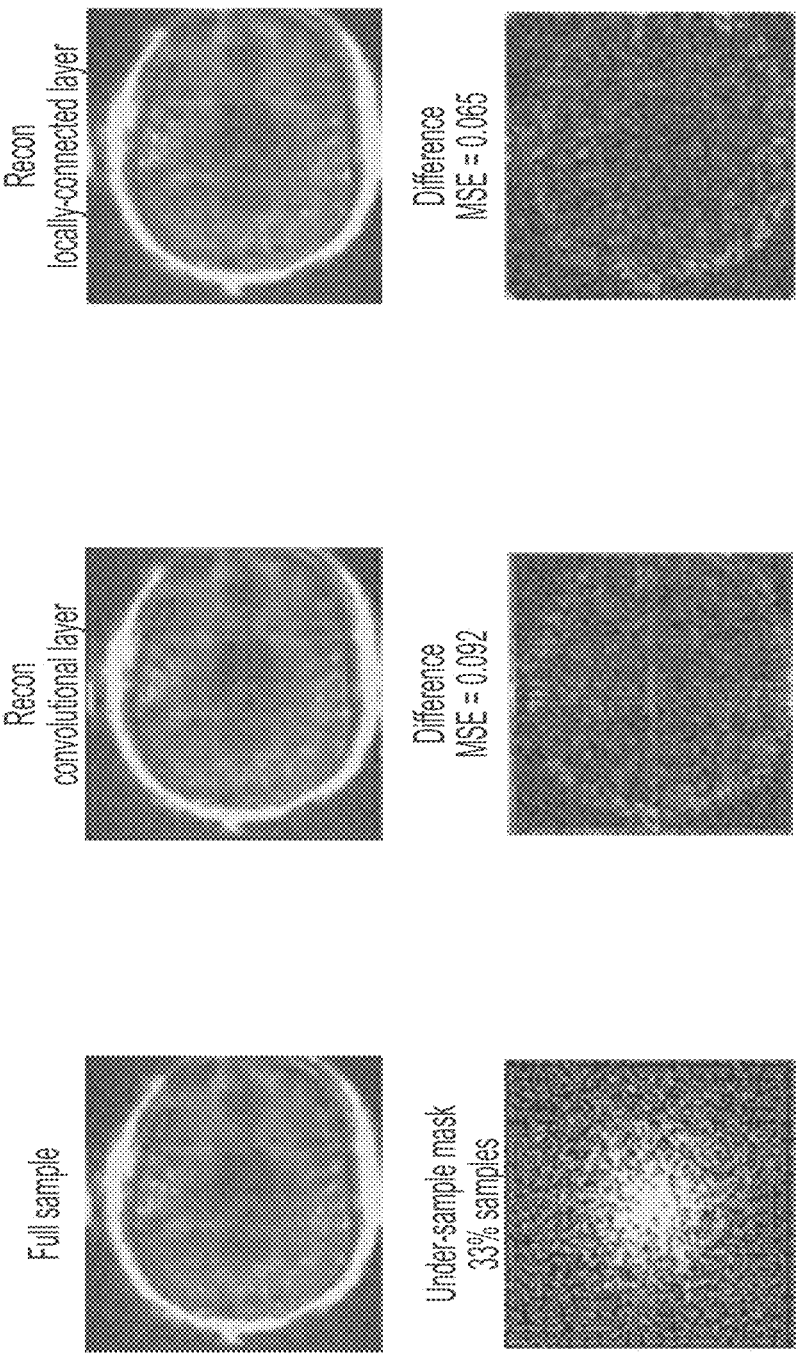
FIG. 3 illustrates the performance of the techniques described herein for generating an MR image from input MR spatial frequency data using a neural network model having a locally-connected layer for operating on data in the spatial frequency domain, in accordance with some embodiments of the technology described herein.

FIG. 3 illustrates the performance improvement obtained by generating an MR image from input MR spatial frequency data using a neural network model having a locally-connected layer. As can be seen in middle column of FIG. 3, the MR image generated from a convolutional layer model without a locally-connected layer generates artifacts (artificial streaks) that deteriorate the image quality. By contrast, as shown in the right column of FIG. 3, using a neural network model having a sub-model with a locally-connected layer (e.g., locally connected layer 106) eliminates such artifacts and produces an image closer to the original image (left column of FIG. 3) in terms of mean-squared error.

Returning back to FIG. 1A, after data is processed by the layers 104, 106, and 108, the data is provided to a complex-conjugate symmetry layer 105, also termed the k-space symmetry layer, whose output is provided as input to data consistency layer 110. The output of the data consistency layer 110, which is also the output of the first neural network sub-model, is then provided as input to IFFT layer 112.

In some embodiments, the complex-conjugate symmetry layer 105 performs interpolation based on the complex-conjugate symmetry in the spatial frequency domain (whereby S(x, y)=S'(−x, −y) with (x,y) being coordinates of a data point and S' representing the complex conjugation of S). In some embodiments, applying the complex-conjugate symmetry layer 105 to spatial frequency domain data involves symmetrically mapping any missing points from existing samples. For example, if a value were obtained for point (x,y), but no corresponding value were obtained for point (−x, −y), the complex-conjugate symmetry layer may be used to provide the value for point (−x, −y) as the complex-conjugate of the obtained value for the point (x,y). Using the complex-conjugate symmetry layer 105 accelerates the convergence of training the neural network model and improves the quality of images produces by the neural network model, as illustrated in the right panel of FIG. 4. Indeed, as shown in the right panel of FIG. 4, using the complex-conjugate symmetry layer allows fewer training epochs to be used when training the neural network model while obtaining improved model performance, which is measured in this illustrative example by relative pixel intensity variation in the center region of the images between the model reconstructed image and the fully-sampled image.

In some embodiments, the data consistency layer 110 may be used to ensure that the application of first neural network sub-model to the spatial frequency data does not alter the values of the spatial frequency data obtained by the MR scanner. To the extent any such value was modified by other layers in the first neural network sub-model (e.g., by convolutional layer(s) 104, locally connected layer 106, and transposed convolutional layer(s) 108), the modified values are replaced by the original values. In this way, the data consistency layer forces the first neural network sub-model to interpolate missing data from the under-sampled spatial frequency data without perturbing the under-sampled spatial frequency data itself.

In some embodiments, any of the neural network layers may include an activation function, which may be non-linear. In some embodiments, the activation function may be a rectified linear unit (ReLU) activation function, a leaky ReLU activation function, a hyperbolic tangent, a sigmoid, or any other suitable activation function, as aspects of the technology described herein are not limited in this respect. For example, one or more of the convolutional layer(s) 104 may include an activation function.

After the spatial frequency data is processed by the data consistency layer 110, the data is provided as input to the IFFT layer 112, which transforms the spatial frequency data to the image domain—the output is initial image domain data 113. The transformation may be performed using a discrete Fourier transform, which may be implemented using a fast Fourier transformation, in some embodiments. The initial image domain data 113, output by the IFFT layer 112, is provided as input to the second neural sub-model 120.

As shown in FIG. 1A the second neural network sub-model 120 includes multiple convolutional blocks 122, 124, and 126. Convolutional block 122 may include one or more convolutional layers 128, an PET layer 130, a complex-conjugate symmetry layer 105, a data consistency layer, an LEFT layer 134 and a residual connection. Each of the blocks 122, 124, and 126 may have the same neural network architecture (e.g., these blocks may have the same types of layers arranged in the same sequence), though the various parameter values for the layers may vary (e.g., the weights of the convolutional layers in block 122 may be different from that of block 124). Although in the illustrative embodiment of FIG. 1A, the second neural network sub-model 120 includes three convolutional blocks, this is by way of example, as in other embodiments the second neural network sub-model 120 may include any suitable number of convolutional blocks (e.g., 1, 2, 4, 5, 6, 7, 8, 9, 10, 11, 12, 13, 14, or 15), as aspects of the technology described herein are not limited in this respect.

When the second neural network sub-model 120 is applied to initial image domain data 113 obtained at the output of the IFFT block 112, the convolutional blocks 122, 124, and 126 are applied to initial image domain data 113 in that order. The application of convolutional block 122 is described next, and it should be appreciated that the convolutional blocks 124 and 126 may be applied in a similar way to the image domain data provided as input to them.

As shown in FIG. 1A, convolutional block 122 includes at least one convolutional layer 128, followed by an FFT layer 130, a complex-conjugate symmetry layer 105, data consistency layer 132, and IFFT layer 134.

In some embodiments, convolutional block 128 includes one or more convolutional layers with stride greater than 1 (e.g., 2 or greater) to downsample the image, followed by one or more transposed convolutional layers with stride greater than 1 (e.g., 2 or greater), which upsample the image to its original size. This structure of down-sampling followed by up-sampling allows operations to be performed at different resolutions, which helps the neural network model to capture both local and global features. In turn, this helps to eliminate image artifacts that may result from under-sampling in the spatial frequency domain. In this illustrative embodiment, the convolutional layers do not include skip connections, which may consume a substantial amount of memory. For example, in some embodiments, convolutional block 128 has five layers with the number of filters being 16, 32, 64, 32, and 2, respectively. In some embodiments, each of the filters may be a 3×3 filter with a Leaky ReLU activation, though in other embodiments different size filters and/or different activation functions may be used.

The impact of variable resolution layers is shown in FIG. 4, left panel. Indeed, as shown in the left panel of FIG. 4, using the variable resolution layers allows fewer training epochs to be used when training the neural network model while obtaining improved model performance, which is measured in this illustrative example by relative pixel intensity variation in the center region of the images between the model reconstructed image and the fully-sampled image.

As shown in the illustrative embodiment of FIG. 1A, after the convolutional layers of convolutional block 122 are applied, the data may be transformed into the spatial frequency domain so that the complex-conjugate symmetry and the data consistency blocks may be applied, after which the data is transformed back into the image domain, and one or more other convolutional blocks may be applied.

In the embodiment illustrated in FIG. 1A, each of the convolutional blocks 122, 124, and 126 includes complex-conjugate symmetry and data consistency blocks. However, in other embodiments, one or more (or all) of the convolutional blocks part of second neural network sub-model 120 may not have either one or both of these blocks, as aspects of the technology described herein are not limited in this respect.

Figure 1B:
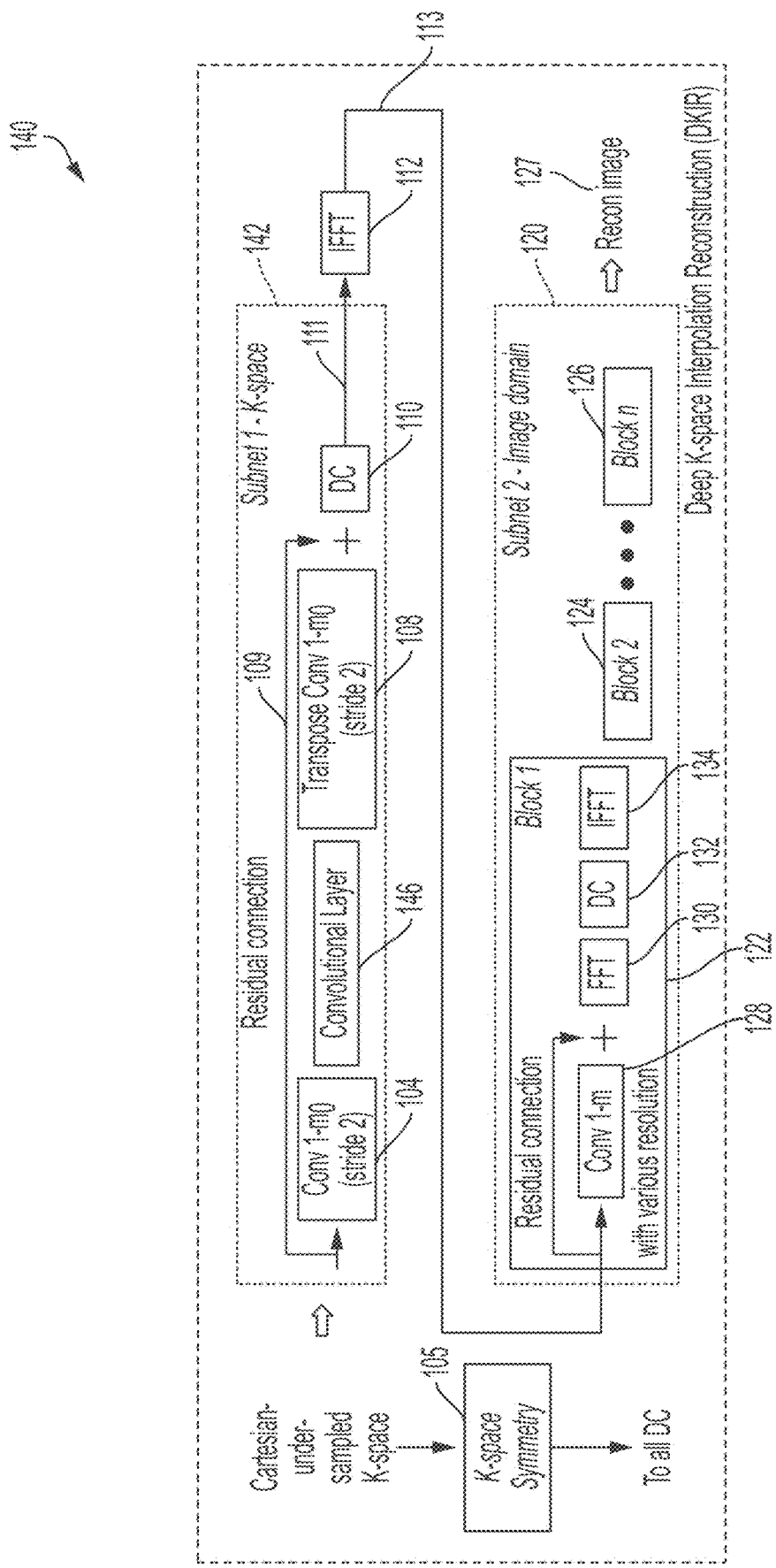
FIG. 1B illustrates the architecture of another example neural network model for generating an MR image from input MR spatial frequency data, in accordance with some embodiments of the technology described herein.

FIG. 1B illustrates the architecture of another example neural network model 140 for generating MR images from input MR spatial frequency data, in accordance with some embodiments of the technology described herein. Neural network model 140 has a first neural network sub-model 142 with a convolutional layer 146 instead of a locally-connected layer (e.g., in contrast with first neural network sub-model 102 of model 100 that has a locally connected layer 106). Such an embodiment may be advantageous as the convolutional layer 142 has fewer parameters to learn during training than the locally-connected layer 106. In other respects, neural network models 140 and 100 are the same.

Figure 1C:
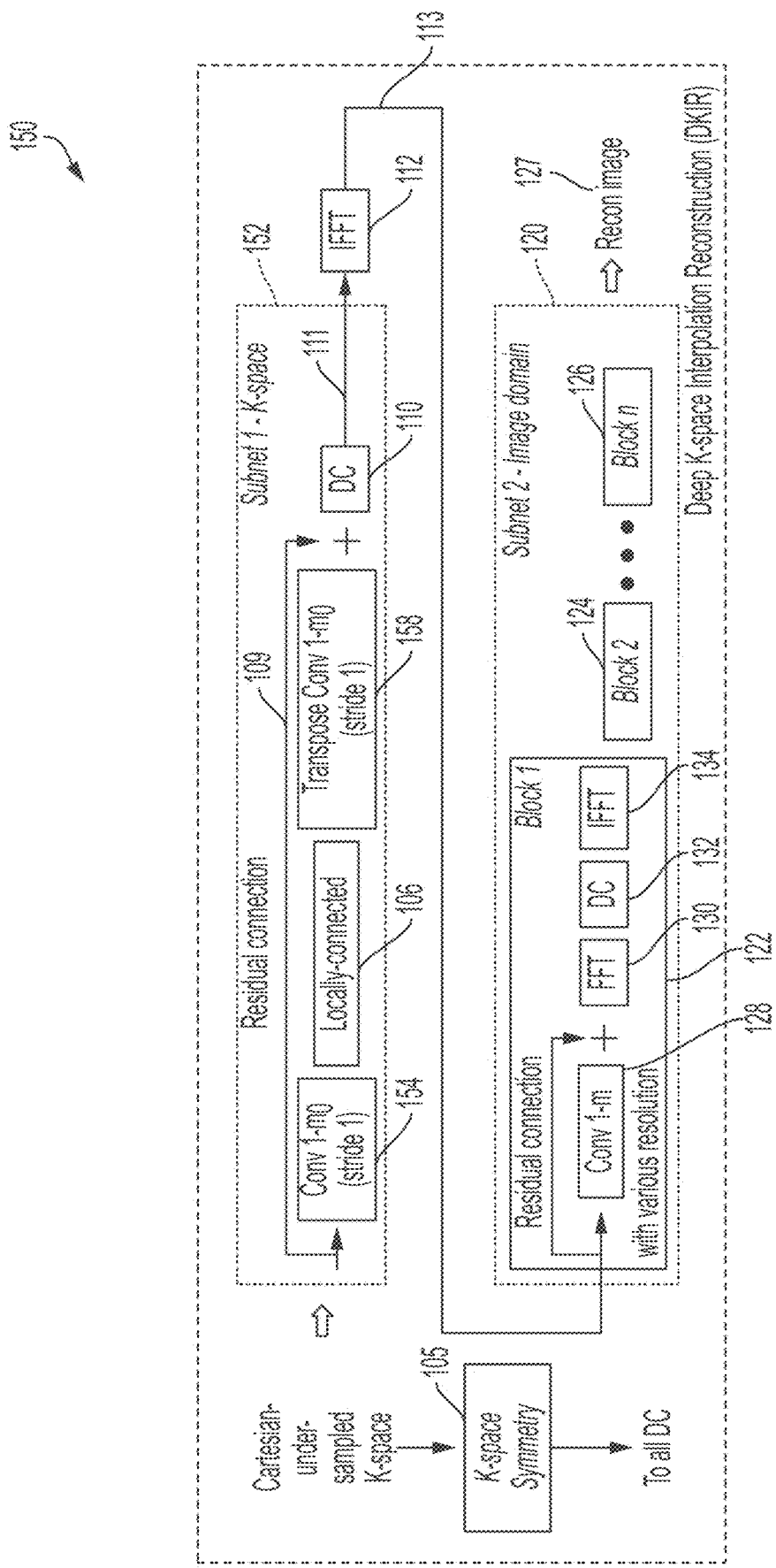
FIG. 1C illustrates the architecture of yet another example neural network model for generating an MR image from input MR spatial frequency data, in accordance with some embodiments of the technology described herein.

FIG. 1C illustrates the architecture of yet another example neural network model 150 for generating MR images from input MR spatial frequency data, in accordance with some embodiments of the technology described herein. Neural network model 150 has a first neural network sub-model 152, with convolutional block 154 and transposed convolutional block 158. However, unlike corresponding convolutional block 104 and transposed convolutional block 108 of neural network model 100, the convolutional blocks 154 and 158 contain convolutional (and transposed convolutional) layers using a stride of 1. As a result, the first neural network sub-model 152 does not perform up-sampling or down-sampling. Such an architecture may be advantageous when there is a large volume of training data available.

Figure 2A:
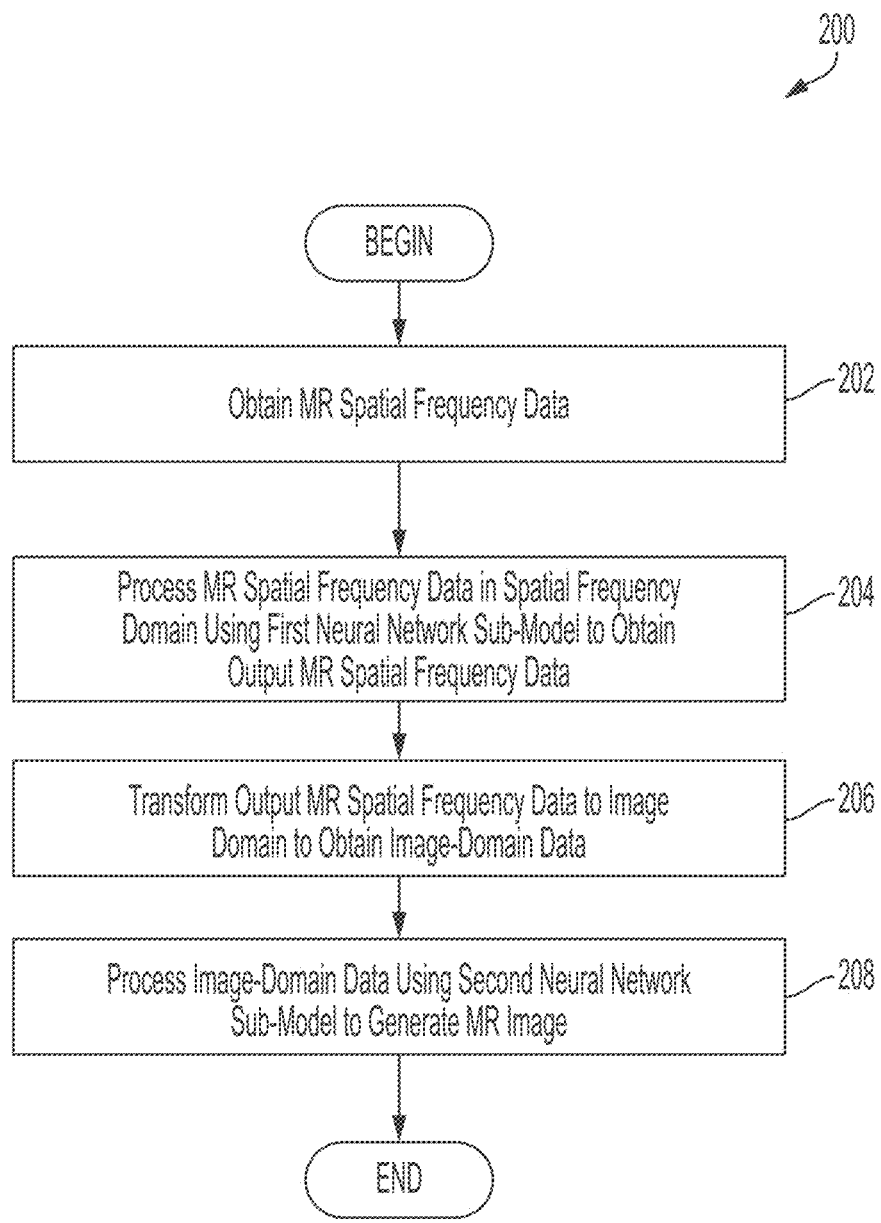
FIG. 2A is a flowchart of an illustrative process 200 for generating an MR image from input MR spatial frequency data using a neural network model, in accordance with some embodiments of the technology described herein.

FIG. 2A is a flowchart of an illustrative process 200 for generating an MR image from input MR spatial frequency data using a neural network model, in accordance with some embodiments of the technology described herein. Process 200 may be implemented using any suitable neural network architecture described herein including any of the neural network architectures described with reference to FIGS. 1A-1C and 5A-5C. Process 200 may be executed using any suitable computing device(s), as aspects of the technology described herein are not limited in this respect. For example, in some embodiments, process 200 may be executed by a computing device communicatively coupled to or part of an MR imaging system.

Process 200 begins at act 202, where spatial frequency domain data is obtained. In some embodiments, the spatial frequency domain data may be obtained by using an MR scanner including any of the MR scanners described herein. In some embodiments, the spatial frequency domain data may have been obtained by an MR scanner prior to the execution of process 200, stored, and the stored data may be accessed during act 202.

In some embodiments, the spatial frequency domain data may be under-sampled relative to the Nyquist sampling criterion. For example, in some embodiments, the spatial frequency domain data may include less than 90% (or less than 80%, or less than 75%, or less than 70%, or less than 65%, or less than 60%, or less than 55%, or less than 50%, or less than 40%, or less than 35%, or any percentage between 25 and 100) of the number of data samples required by the Nyquist criterion.

The spatial frequency domain data obtained at act 202 may be (or may have been) obtained by an MR scanner using any suitable pulse sequence and sampling scheme. For example, in some embodiments, the spatial frequency domain data may be gathered using a Cartesian sampling scheme. In other embodiments, the spatial frequency domain data may be gathered using a non-Cartesian sampling scheme (e.g., radial, spiral, rosette, Lissajou, etc.).

Next, process 200 proceeds to act 204, where the MR spatial frequency data obtained at act 202 is processed using a first neural network sub-model (e.g., sub-model 102 described with reference to FIG. 1A, sub-model 142 described with reference to FIG. 1B, sub-model 152 described with reference to FIG. 1C, sub-model 502 described with reference to FIG. 5A, sub-model 522 described with reference to FIG. 5B, and sub-model 532 described with reference to FIG. 5C). Illustrative examples of how act 204 may be implemented are described with reference to FIGS. 2B and 2C.

Next, process 200 proceeds to act 206, where the spatial frequency domain data obtained at the completion of act 204 is transformed to obtain initial image domain data (e.g., using a Fourier transformation).

Next, process 200 proceeds to act 208, where initial the image domain data obtained at the completion of act 206 is processed a second neural network sub-model (e.g., sub-model 120 described with reference to FIG. 1A, sub-model 510 described with reference to FIG. 5A) to generate an MR image. An illustrative example of how act 208 may be implemented is described with reference to FIG. 2D.

Figure 2B:
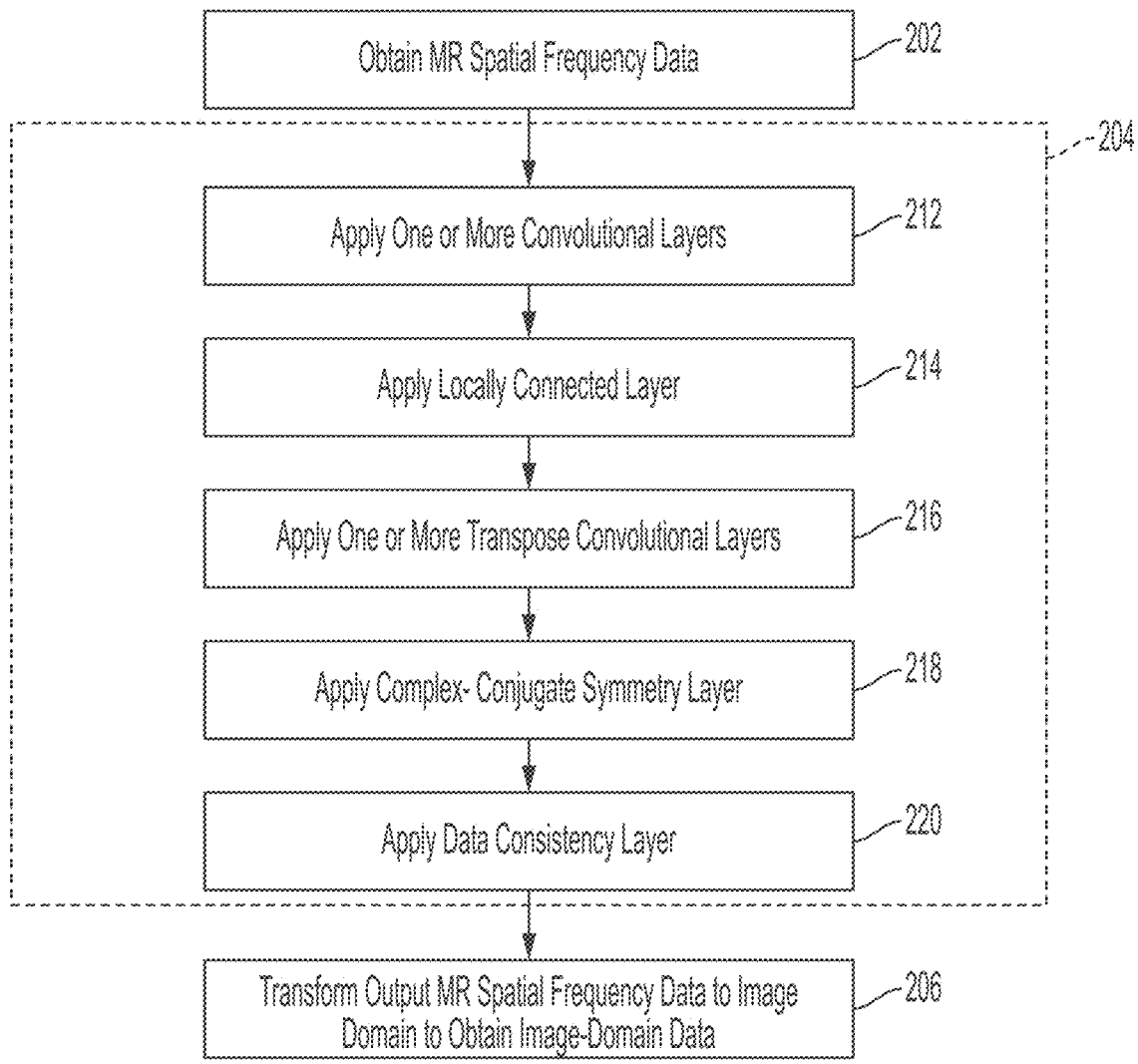
FIG. 2B is a flowchart of an illustrative process for processing MR spatial frequency data in the spatial frequency domain, which may be part of the illustrative process 200, to obtain output spatial frequency data, in accordance with some embodiments of the technology described herein.

FIG. 2B is a flowchart of an illustrative process for processing MR spatial frequency data in the spatial frequency domain, which may be part of the illustrative process 200, to obtain output spatial frequency data, in accordance with some embodiments of the technology described herein. In particular, FIG. 2B shows an illustrative embodiment for implementing act 204 of process 200.

As shown in FIG. 2B, act 204 may be implemented using acts 212-218. At act 212, one or more convolutional layers may be applied to the spatial frequency domain data obtained at act 202. In some embodiments, the convolutional layer(s) applied at act 212 may be part of block 104 described with reference to FIG. 1A or block 154 described with reference to FIG. 1C. In some embodiments, the convolutional layer(s) may include any suitable number of layers including any number of layers in the range of 1-20 layers. In some embodiments, the convolutional layer(s) may be implemented using a stride greater than one (e.g., 2) to downsample the data. In other embodiments, the convolutional layer(s) may be implemented using a stride of 1.

Next, at act 214, a locally connected layer is applied to spatial frequency domain data obtained at the completion of act 212. In some embodiments, the local convolutional layer may be the local convolutional layer 106 described with reference to FIG. 1A. In some embodiments, the locally-connected layer has a respective set of weights for each data point in the spatial frequency domain data.

Next, at act 216, one or more transposed convolutional layers are applied to spatial frequency domain data obtained at the completion of act 214. In some embodiments, the transposed convolutional layer(s) may be the transposed convolutional layer(s) part of block 108 described with reference to FIG. 1A or block 158 described with reference to FIG. 1C. In some embodiments, the transposed convolutional layer(s) may upsample the data.

Next, at act 218, a complex conjugate symmetry layer is applied to the spatial frequency domain data output at the completion of act 216. In some embodiments, the complex conjugate symmetry layer may be the complex conjugate symmetry layer 105 described with reference to FIG. 1A. As described herein, applying the complex-conjugate symmetry layer 105 to spatial frequency domain data may involve symmetrically mapping any missing points from existing samples. For example, if a value were obtained for point (x,y), but no corresponding value were obtained for point (−x, −y), the complex-conjugate symmetry layer may be used to provide the value for point (−x, −y) as the complex-conjugate of the obtained value for the point (x,y).

Next, at act 220, a data consistency layer is applied to the spatial frequency domain data output at the completion of act 218. In some embodiments, the data consistency layer may be the data consistency layer 110 described with reference to FIG. 1A. As described herein, the data consistency layer may be used to ensure that the application of first neural network sub-model to the spatial frequency data does not alter the values of the spatial frequency data obtained by the MR scanner.

FIG. 2C is a flowchart of an illustrative process for processing spatial frequency data, which may be part of the illustrative process 200, to generate an MR image, in accordance with some embodiments of the technology described herein. In particular, FIG. 2C shows another illustrative embodiment for implementing act 204 of process 200.

As shown in FIG. 2C, act 204 may be implemented using acts 222 and 224. At act 222, one or more fully connected layers are applied to the spatial frequency data obtained at act 202. In some embodiments, the fully connected layer(s) applied at act 222 may be fully connected layer 502 described with reference to FIG. 5A. As described herein, the fully connected layer represents a learned mapping from non-Cartesian to Cartesian coordinates from data, which allows MR images to be reconstructed from non-Cartesian samples without relying on conventional gridding or other interpolation schemes, which are not data dependent.

In some embodiments, at act 222, the spatial frequency data obtained at act 202 is split into real and imaginary portions and the same fully connected layer is applied to each of the two portions. Equivalently, one may consider these data as being provided to a fully connected layer with shared weights for the real and imaginary channels. Such a weight sharing scheme ensures that the same interpolation operation is applied to both the real and imaginary channels, which preserves the underlying spatial frequency domain symmetry throughout the process. In addition, sharing the weights between the real and imaginary portions reduces the number of trainable parameters in the model by a factor of two. However, in other embodiments, the spatial frequency data may be fed to a fully connected layer with partial or no weight sharing between the real and imaginary channels.

Next, at act 224, batch normalization is applied so that the subsequent layer receives input having a substantially 0 mean and a substantially unit (or any other suitable constant) variance.

It should be appreciated that the process of FIG. 2C is illustrative and that there are variations. For example, in some embodiments, the batch normalization may be omitted.

Figure 2D:
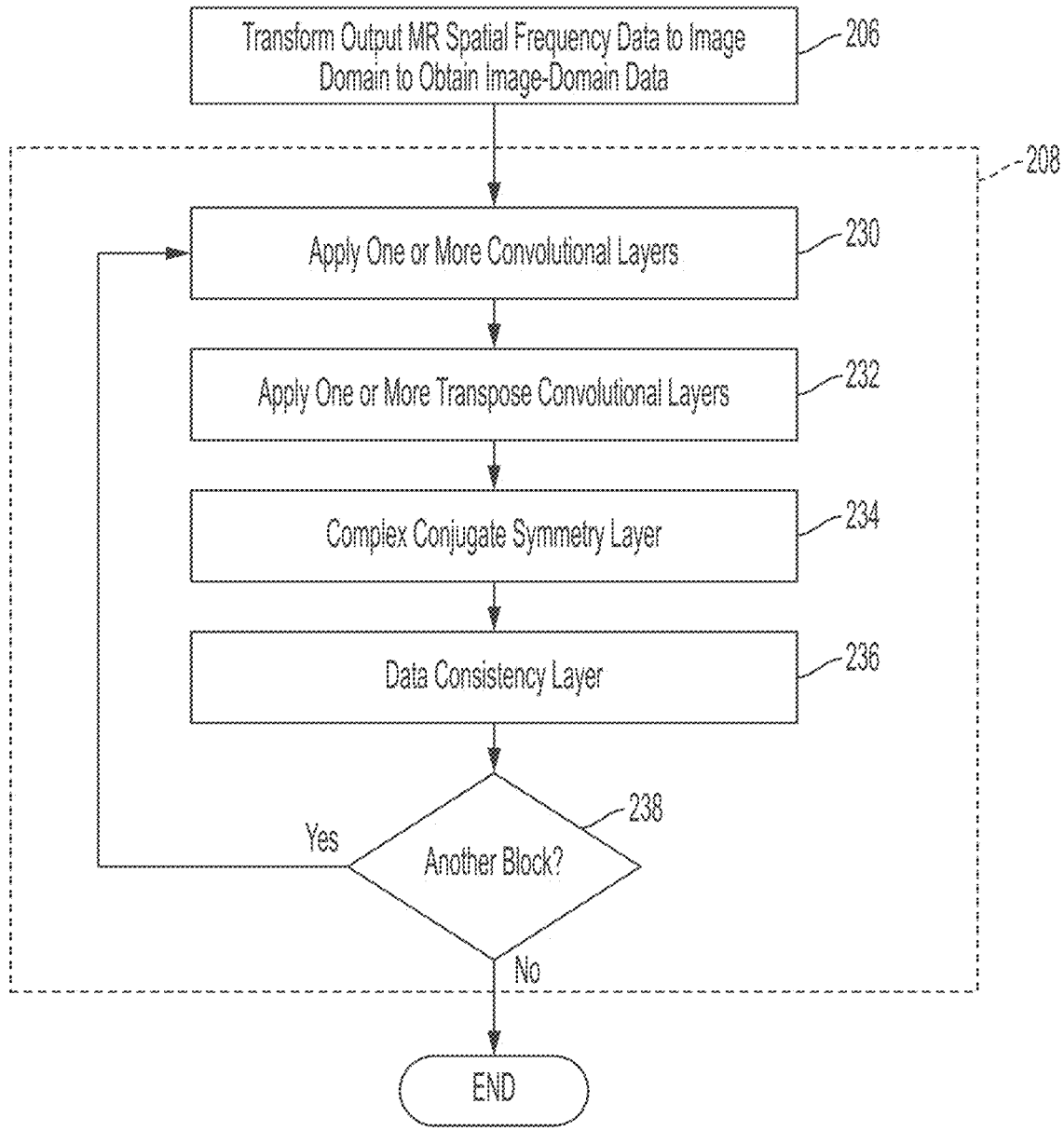
FIG. 2D is a flowchart of another illustrative process for processing image domain data, which may be part of the illustrative process 200, to generate an MR image, in accordance with some embodiments of the technology described herein.

FIG. 2D is a flowchart of another illustrative process for processing image-domain data, which may be part of the illustrative process 200, to generate an MR image, in accordance with some embodiments of the technology described herein. In particular, FIG. 2D shows an illustrative embodiment for implementing act 208 of process 200.

As shown in FIG. 2D, act 208 may be implemented using acts 230-236 and decision block 238. In particular, at act 230, one or more convolutional layers are applied to image domain data obtained at act 206 by transforming spatial frequency domain data to the image domain. In some embodiments, the convolutional layer(s) applied at act 230 may be part of block 128 shown in FIG. 1A or block 512 shown in FIG. 5A. In some embodiments, the convolutional layer(s) may include any suitable number of layers including any number of layers in the range of 1-20 layers. In some embodiments, the convolutional layer(s) may be implemented using a stride greater than one (e.g., 2) to downsample the data. In other embodiments, the convolutional layer(s) may be implemented using a stride of 1.

Next, at act 232, one or more transposed convolutional layers may be applied to the image-domain data output at the completion of act 230. In some embodiments, the transposed convolutional layer(s) applied at act 232 may be part of transpose block 128 shown in FIG. 1A or block 512 shown in FIG. 5A. In some embodiments, the convolutional layer(s) may include any suitable number of layers including any number of layers in the range of 1-20 layers. In some embodiments, the transposed convolutional layer(s) may be implemented to upsample the data (e.g., using a fractional stride).

Next, at act 234, a complex-conjugate symmetry layer may be applied to the data. As the complex-conjugate symmetry layer is applied in the spatial frequency domain, the image domain data output at the completion of act 232 is transformed to the spatial frequency domain prior to the application of the complex-conjugate symmetry layer. In some embodiments, the complex conjugate symmetry layer may be the complex-conjugate symmetry layer 105 described with reference to FIG. 1A.

Next, at act 236, a data consistency layer may be applied to the data. In some embodiments, the data consistency layer may be applied to spatial frequency domain data output at completion of act 234. In other embodiments, if act 234 were omitted, the image domain data output at the completion of act 232 may be transformed to the spatial frequency domain and the data consistency layer may be applied thereto. In some embodiments, the data consistency layer may be the data consistency layer 110 described with reference to FIG. 1A.

Next, at decision block 238, a determination is made as to whether one or more additional image-domain processing blocks are to be applied. When it is determined that no further blocks are to be applied, the process completes. Otherwise, the process returns to act 230, via the "YES" branch, and acts 230-236 and decision block 238 are repeated. For example, as shown in FIG. 1A, after block 122 is applied to the image domain data, it may be determined that block 124 is to be applied to the data.

It should be appreciated that the process of FIG. 2D is illustrative and that there are variations. For example, in some embodiments, the image-domain data may be processed purely in the image domain without application of the complex-conjugate symmetry layer and the data consistency layer.

Figure 5A:
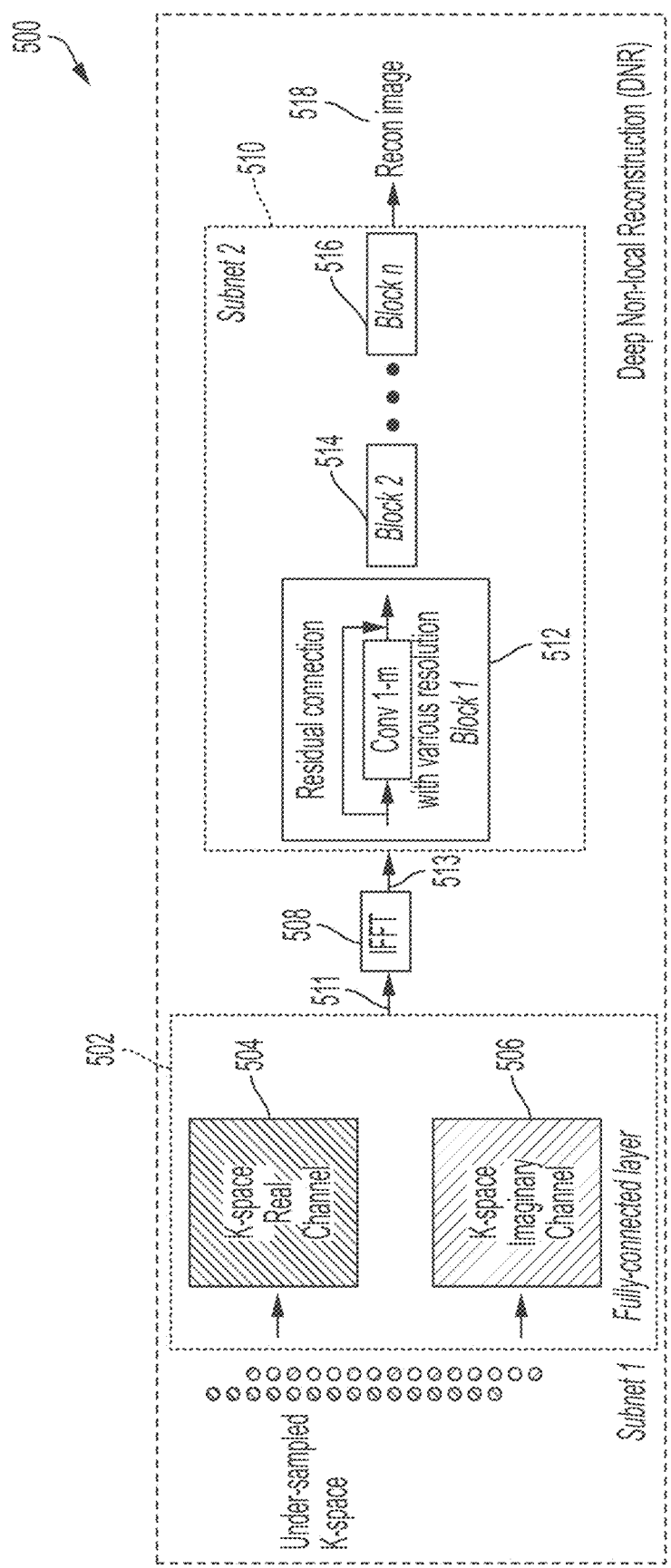
FIG. 5A illustrates the architecture of another example neural network model for generating a magnetic resonance (MR) image from input MR spatial frequency data, in accordance with some embodiments of the technology described herein.

FIG. 5A illustrates the architecture of another example neural network model 500 for generating a magnetic resonance (MR) image from input MR spatial frequency data, in accordance with some embodiments of the technology described herein.

As shown in FIG. 5A, the neural network model 500 comprises first neural network sub-model 502 configured to process spatial frequency domain data, inverse fast Fourier transform (IFFT) layer 508 configured to transform spatial frequency domain data to image domain data, and second neural network sub-model 510 configured to process image domain data. After initial spatial frequency MR data is obtained using an MR scanner (e.g., using any of the low-field MR scanners described herein or any other suitable type of MR scanner), the initial spatial frequency MR data may be processed using the first neural network sub-model 502 to obtain output MR spatial frequency data 511. The MR spatial frequency data 511 is then transformed by IFFT layer 508 to obtain initial image-domain data 513, which is processed by second neural network sub-model 510 to obtain an MR image 518.

As shown in FIG. 5A, the initial spatial frequency domain MR data is split into a real portion 504 (e.g., magnitudes of the complex-valued data) and imaginary portion 506 (e.g., phases of the complex-valued data). The first neural network sub-model 502 includes a fully connected layer that operates on the real portion 504 and imaginary portion 506. In the embodiment shown in FIG. 5A, the fully connected layer shares weights between the real and imaginary channels. As such, the fully connected layer applies the same operations to both the real and imaginary channels, which preserves the underlying spatial frequency domain symmetry throughout the process. In addition, sharing the weights between the real and imaginary portions reduces the number of trainable parameters in the model by a factor of two. However, in other embodiments (e.g., the embodiment of FIG. 5C), the spatial frequency data may be fed to a fully connected layer with partial or no weight sharing between the real and imaginary channels.

In some embodiments, when the neural network model including the fully-connected layer is trained using input MR images generated using the same sample trajectory, the fully-connected layer learns a data-dependent mapping from non-Cartesian to Cartesian coordinates, which can be used to perform a data-dependent gridding of non-Cartesian spatial-frequency data that may be generated by an MR scanner operating in accordance with a non-Cartesian sequence. This is illustrated further in FIGS. 6A-6C.

Figure 6A:
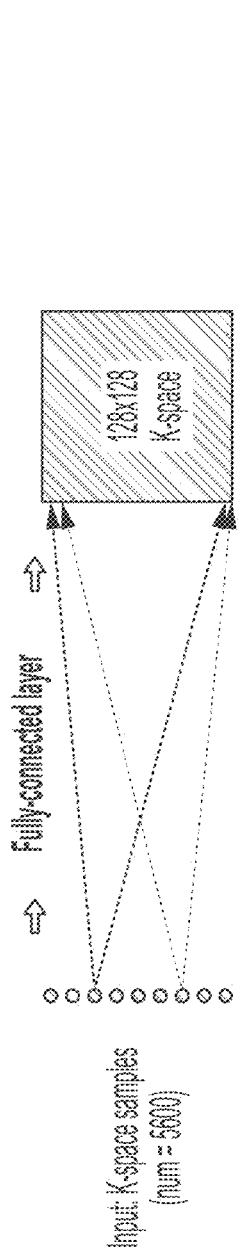
FIGS. 6A-6C illustrate the distribution of weights of a fully-connected network layer in a neural network sub-model configured to process spatial frequency domain data, in accordance with some embodiments of the technology described herein.
Figure 6B:
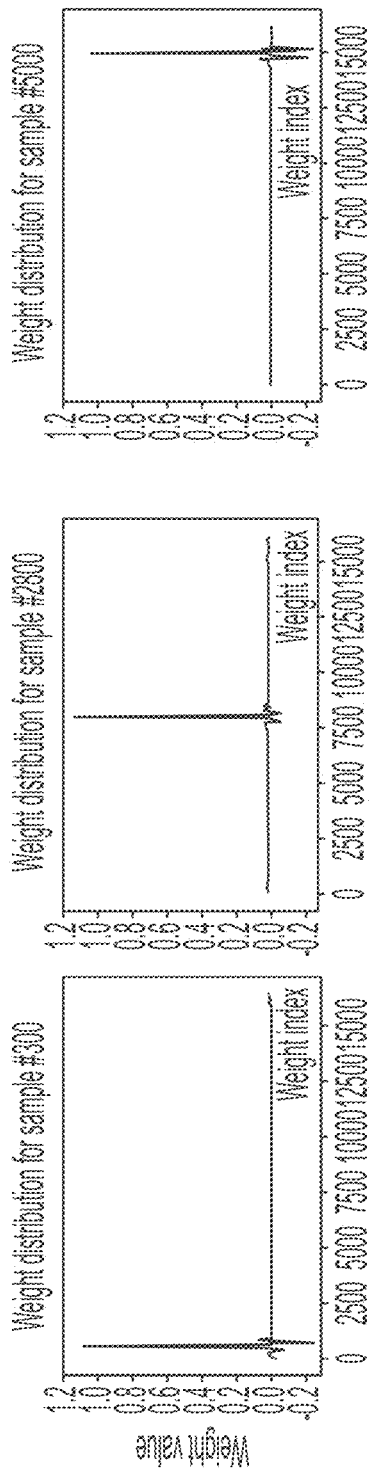

FIG. 6A shows an illustrative embodiment in which each data point in the spatial frequency domain has a corresponding 128×128 weight matrix having a weight for each location in a 128×128 output k-space, creating a non-local interpolation. The distribution of weights for three spatial frequency domain data points (#300, #2800, and #5000) is shown in FIG. 6B. The 2D distributions of these same three data points are shown in FIG. 6C, with zoomed-in views to show the details of the weight distribution.

Figure 6C:
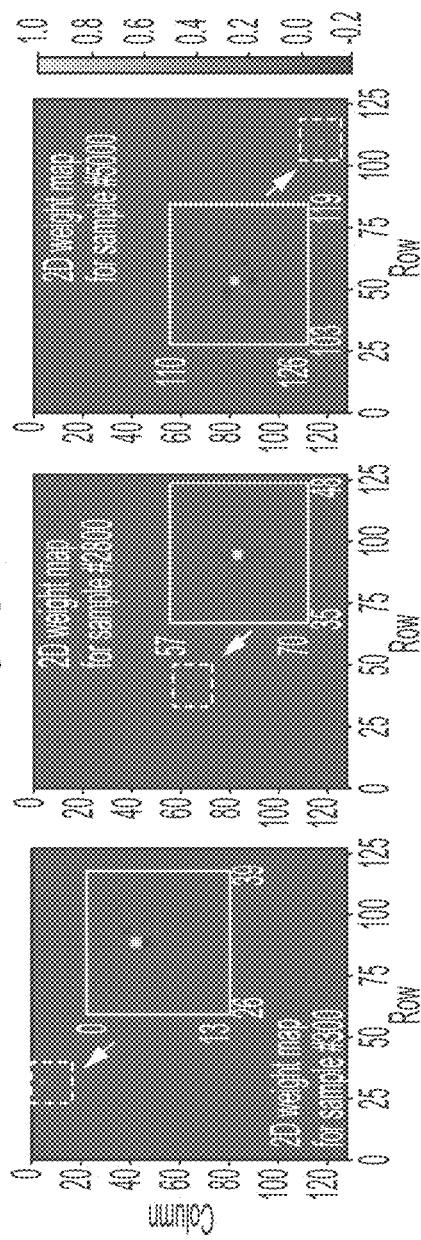

As shown in the 1D and 2D weight distributions of FIGS. 6B-6C, when plotting a two-dimensional weight map of a particular spatial frequency domain data point, it is predominantly the weights in a local neighborhood of the data point that have non-negligible values, with other weights having values close to zero. The weight distribution indicates that the mapping performed by the fully-connected layer performs a local interpolation. It should be noted that the first neural network sub-model 502 does not include a data consistency layer, which allows the first neural network sub-model 502 to process non-Cartesian samples.

Returning to FIG. 5A, after the spatial frequency data is processed by the first neural network model 502, the data is provided as input to the IFFT layer 508, which transforms the spatial frequency data to the image domain—the output is initial image domain data 513. The transformation may be performed using a discrete Fourier transform, which may be implemented using a fast Fourier transformation, in some embodiments. The initial image domain data 513, output by the IFFT layer 508, is provided as input to the second neural sub-model 510.

As shown in FIG. 5A the second neural network sub-model 510 includes multiple convolutional blocks 512, 514, and 516. Convolutional block 512 may include one or more convolutional layers and a residual connection. Each of the convolutional blocks 512, 514, and 516 may have the same neural network architecture (e.g., these blocks may have the same types of layers arranged in the same sequence), though the various parameter values for the layers may vary (e.g., the weights of the convolutional layers in block 512 may be different from that of block 514). Although in the illustrative embodiment of FIG. 5A the second neural network sub-model 510 includes three convolutional blocks, this is by way of example, as in other embodiments the second neural network sub-model 510 may include any suitable number of convolutional blocks (e.g., 1, 2, 4, 5, 6, 7, 8, 9, 10, 11, 12, 13, 14, or 15), as aspects of the technology described herein are not limited in this respect.

When the second neural network sub-model 510 is applied to initial image domain data 513 obtained at the output of the IFFT block 508, the convolutional blocks 512, 514, and 516 are applied to initial image domain data 513 in that order. The application of convolutional block 512 is described next, and it should be appreciated that the convolutional blocks 514 and 516 may be applied in a similar way to the image domain data provided as input to them (after being output from the preceding block).

In some embodiments, convolutional block 512 includes one or more convolutional layers with stride greater than 1 (e.g., 2 or greater) to downsample the image, followed by one or more transposed convolutional layers with stride greater than 1 (e.g., 2 or greater), which upsample the image to its original size. This structure of down-sampling followed by up-sampling allows operations to be performed at different resolutions, which helps the neural network model to capture both local and global features. In turn, this helps to eliminate image artifacts that may result from under-sampling in the spatial frequency domain.

For example, in some embodiments, convolutional block 512 may include two sequential convolutional layers (having 32 3×3 and 64 3×3 filters in the two respective layers, with stride 2), followed by two transposed convolutional layers (128 3×3 and 64 3×3 filters in the two respective layers, with stride 2), followed by a final convolutional layer (2 3×3 filters with stride 1). A non-linear activation (e.g., a ReLU or a Leaky ReLU activation) may be applied in each of the first four layers, except for the final convolutional layer. Though, it should be appreciated that in other embodiments, different size filters and/or different activation functions may be used, as aspects of the technology described herein are not limited in this respect.

Figure 5B:
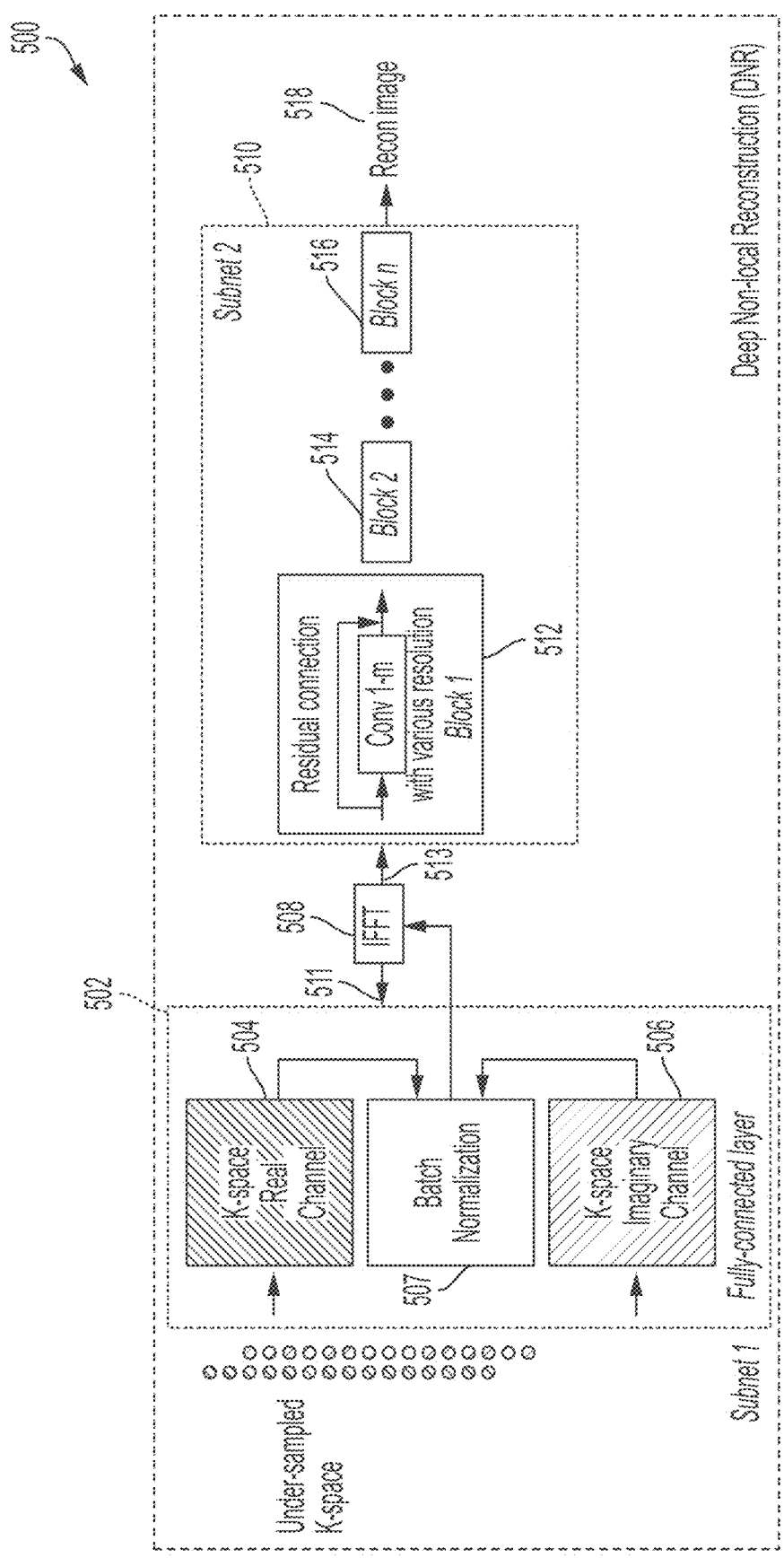
FIG. 5B illustrates the architecture of another example neural network model for generating a magnetic resonance (MR) image from input MR spatial frequency data, in accordance with some embodiments of the technology described herein.

FIG. 5B illustrates the architecture of another example neural network model 520 for generating a magnetic resonance (MR) image from input MR spatial frequency data, in accordance with some embodiments of the technology described herein. Neural network 520 has a first neural network sub-model 522 with a batch normalization layer 507 following application of the fully connected layer and prior to the output of data from the first neural network sub-model 522 to the IFFT layer 508. Introducing a batch normalization layer at this juncture improves the performance of the neural network and may reduce the time required for training. In other respects, neural network models 520 and 500 are the same.

Figure 5C:
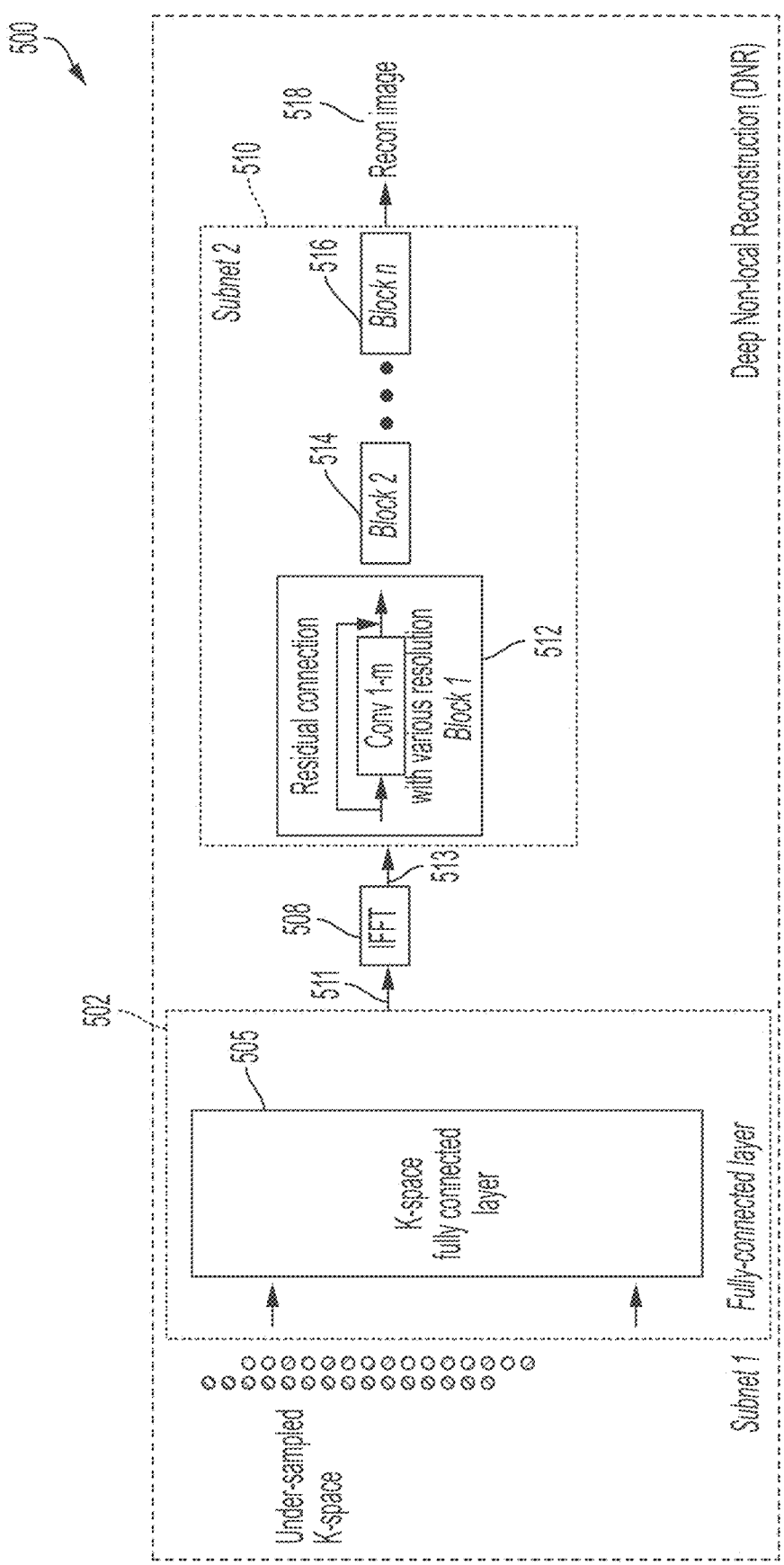
FIG. 5C illustrates the architecture of another example neural network model for generating a magnetic resonance (MR) image from input MR spatial frequency data, in accordance with some embodiments of the technology described herein.

FIG. 5C illustrates the architecture of another example neural network model 530 for generating a magnetic resonance (MR) image from input MR spatial frequency data, in accordance with some embodiments of the technology described herein. Neural network 530 has a first neural network sub-model 532 which includes a fully connected layer that does not use weight sharing between the real and imaginary portions of the obtained MR data. In other respects, neural network models 530 and 500 are the same.

Figure 7:
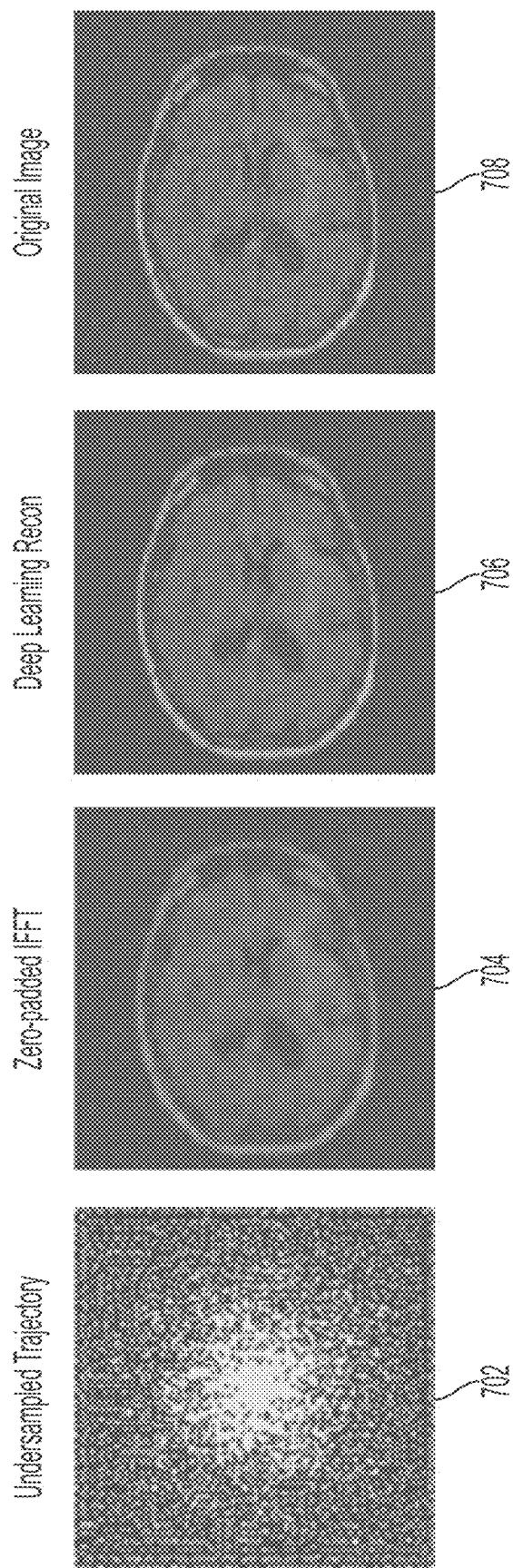
FIG. 7 illustrates results of generating MR images, from under-sampled spatial frequency domain data sampled using a non-Cartesian sampling trajectory, using the techniques described herein and a zero-padded inverse Fourier transform, in accordance with some embodiments of the technology described herein.

The inventors have developed a novel non-Cartesian sampling trajectory to accelerate acquisition of spatial domain data, while retaining as much information as possible. The sampling trajectory consists of unstructured triangular and tetrahedral meshes to evenly under-sample the entire spatial frequency domain, and a fully sampling grid in the k-space center generated by a Gaussian kernel, as full coverage of the k-space center is important for reconstructions of images with low signal-to-noise ratio (SNR). This sampling trajectory samples 33% of the spatial frequency domain samples need to satisfy the Nyquist criterion (though as described above a sampling trajectory may be used with any other percentage described herein, including for example any percentage in the range of 25-100, such as 35%, 40%, 45%, 50%, 55%, 60%, 65%, 70%, 75%, 80%, etc.), K-space. FIG. 7 illustrates the novel non-Cartesian sampling trajectory (panel 702), the image reconstructed from samples obtained using the trajectory of panel 702 and a zero-padded inverse fast Fourier transform (panel 704), the image reconstructed from samples obtained using the trajectory of panel 702 and the neural network model described with reference to FIG. 5B (panel 706), and the original MR image. As can be seen from panels 704 and 706, the MR image obtained using a zero-padded IFFT is blurred and has artifacts, while the MR image obtained using the neural network model of FIG. 5B does not suffer from these drawbacks.

The inventors have developed specialized techniques for training the neural network models described herein. The training procedure involves generating complex image data, under-sampling the complex image data, and using pairs of under-sampled and fully sampled complex image data to train the neural network model using any suitable training techniques (e.g., stochastic gradient descent and back-propagation). In order to generate complex image data, magnitude images were used to synthesize the phase information, as described below.

Figure 8:
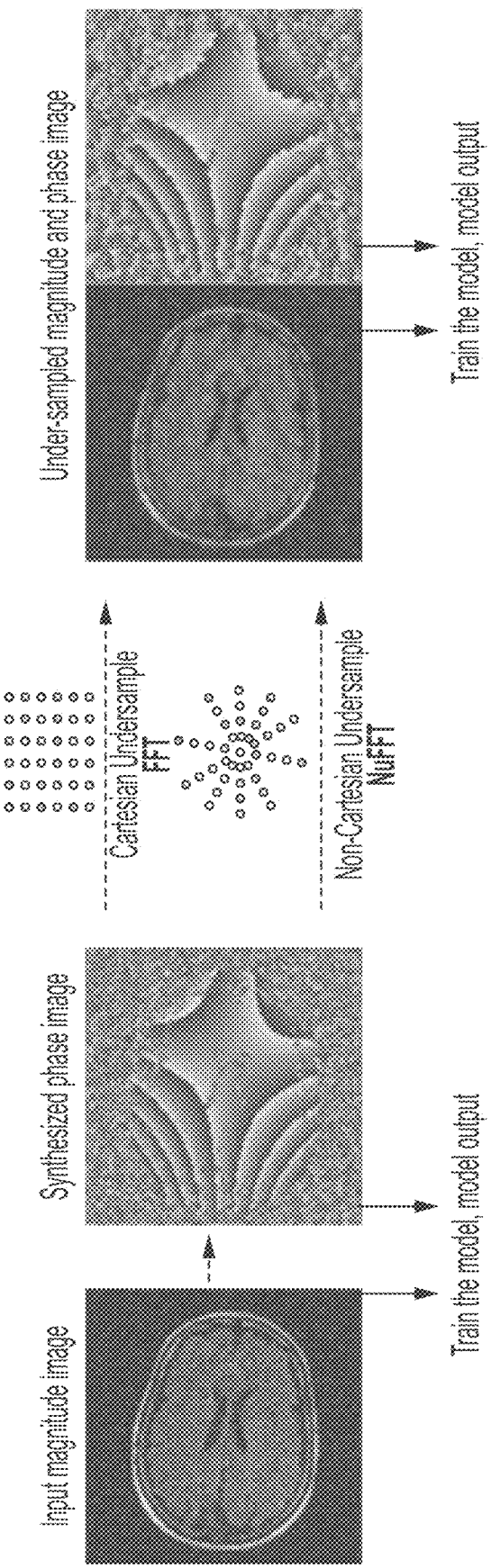
FIG. 8 illustrates aspects of training a neural network model for generating MR images from under-sampled spatial frequency domain data, in accordance with some embodiments of the technology described herein.

FIG. 8 illustrates aspects of training a neural network model for generating MR images from under-sampled spatial frequency domain data, in accordance with some embodiments of the technology described herein. As shown in FIG. 8, the training process involves using input magnitude images to synthesize the phase information. The magnitude and phase information that constitute the complex image data which can be retrospectively under-sampled in the spatial frequency domain using Cartesian or a non-Cartesian (e.g., radial, etc.) sampling trajectory. The under-sampled data will be used as the input to the neural network model being trained, while the full-sampled image will be the output of the model.

Although there are many publicly available MR image datasets available, they typically only include magnitude images. To simulate complex data as acquired by an MR scanner, the inventors have developed a technique for generating phase information to append to the magnitude images. Accordingly, in some embodiments, phase information is generated using a weighted sum of spherical harmonic basis functions. The combination of these functions can characterize magnetic field variation derived from inhomogeneity of the $B_0$, magnetic field drifting with temperature, gradient eddy currents, spatially-varying RF coil sensitivity fields, inaccuracies in gradient fields in sequences and/or other effects that may contribute to phase variation. The process of generating phase information using spherical harmonics is illustrated in FIG. 9A.

In some embodiments, to simulate non-Cartesian under-sampling, a non-uniform FFT (NuFFT) was used to transform MR images to the spatial-frequency domain where a non-Cartesian under-sampling mask was applied. In turn, the under-sampled spatial frequency data can be converted to the image domain using an inverse (also called backward) NuFFT, which can be provided as input to the image-domain sub-models. In this way, the use of NuFFT, enables performing non-uniform K-space sampling, which highly resembles the non-Cartesian sampling in practice.

In some embodiments, the available training data was augmented by applying affine transformations to individual slices to create images with different orientation and size, adding noise to create images with different SNR, introducing motion artifacts, incorporating phase and/or signal modulation for more complex sequences like echo trains, and/or modeling the dephasing of the signal to adapt the model to a sequence like diffusion weighted imaging.

As the neural network models described herein operate both in the spatial frequency domain and in the image domain, the inventors have developed a new loss function to facilitate training such a mixed-domain neural network model. The new loss function accelerated the process of training the neural network models described herein (e.g., by reducing the number of training epochs needed to achieve a given level of performance).

In some embodiments, the loss function includes a first loss function to capture error in the spatial frequency domain and a second loss function to capture error in the image domain. For example, as shown in FIG. 9B, the output of the first neural network sub-model (labeled as "Subnet 1 k-Space") may be compared to ground truth in the spatial frequency domain to obtain a first measure of error (e.g., mean squared error, labeled "MSE Loss 1") in the spatial frequency domain, and the output of the second neural network sub-model (labeled as "Subnet 2 Image domain") may be compared to ground truth in the image domain to obtain a second measure of error (e.g., mean squared error, labeled "MSF Loss 2") in the image domain. The first and second measures of error may be combined (e.g., via a weighted combination) to produce an overall measure of error, which is to be minimized during the training process. For example, in the illustrative example of FIG. 9, the two loss functions were combined using a weight of $\lambda$, $<1$ such that the overall loss function was given by Loss1+$\lambda$*Loss2.

As described herein, in order to train the neural network models developed by the inventors to generate MR images from under-sampled spatial frequency data obtained by a low-field MRI system, training data obtained using the low-field MRI system is needed. However, there may not be a sufficient volume of such data to learn all the parameters of the models described herein.

Accordingly, in some embodiments, a neural network model is first trained using images obtained using one or more "high-field" and/or a "mid-field" MR systems and then transfer learning is used to adapt the trained neural network model to the "low-field" context by using one or more MR images obtained using a low-field MRI system.

FIGS. 10A-10H illustrates MR images generated using a zero-padded inverse DFT and using neural network models, trained with and without transfer learning, in accordance with some embodiments of the technology described herein. The results show that using transfer learning (100 epochs in this illustrative example) improves performance of the model on low-field MR images. In particular, FIG. 10A-10D show reconstructed MR images obtained, respectively, using a zero-padded inverse FFT, the neural network model of FIG. 5B trained without transfer learning, the neural network of FIG. 5B trained with transfer learning, as well as the fully sampled data. The FIGS. 10E-10G show the absolute difference between the reconstructed MR images and the fully sampled MR images, while FIG. 10H shows the under-sampling mask.

Figure 11:
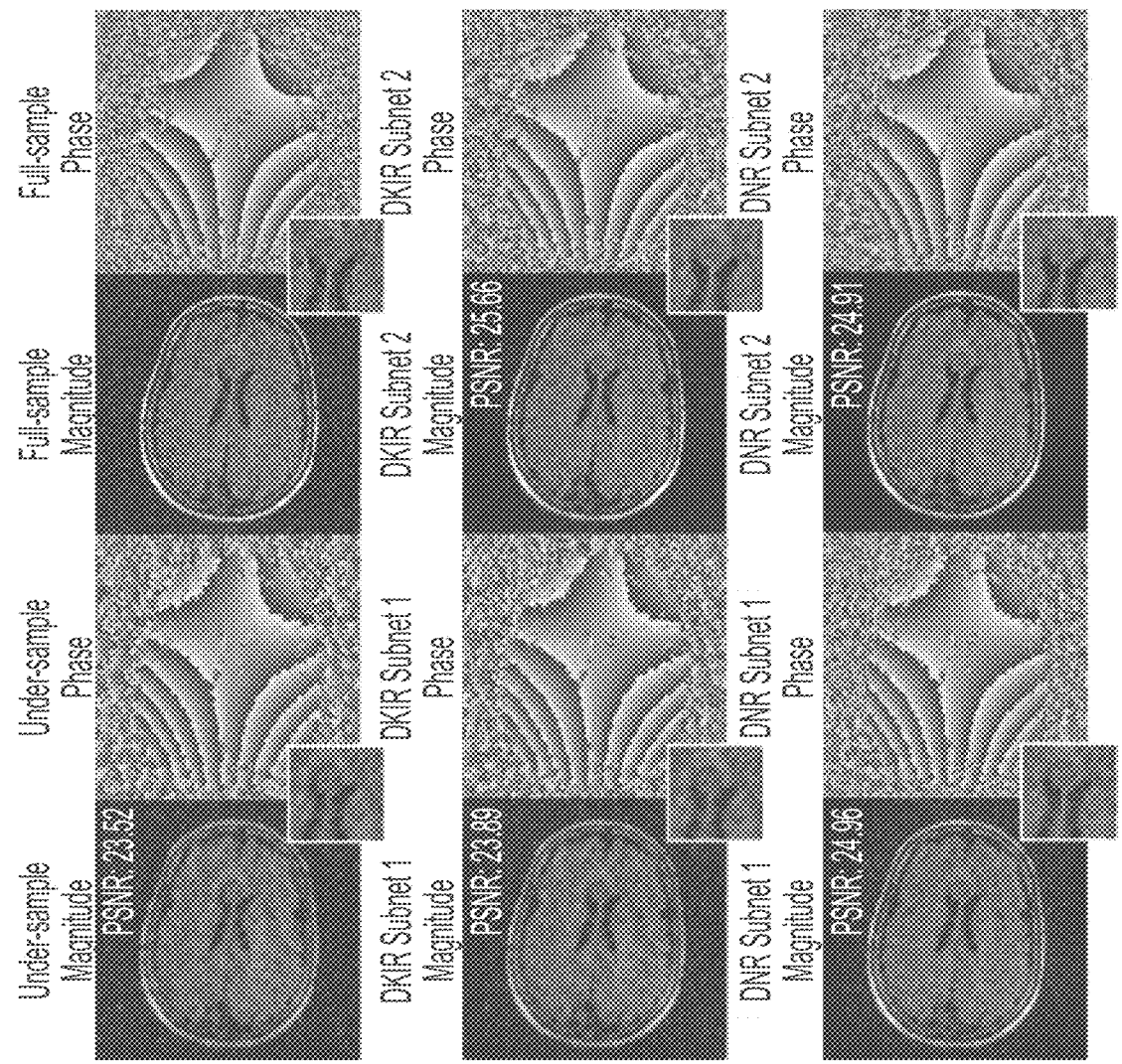
FIG. 11 illustrates performance of some of the neural network models for generating MR images from under-sampled spatial frequency domain data, in accordance with some embodiments of the technology described herein.

FIG. 11 illustrates performance of some of the neural network models for generating MR images from under-sampled spatial frequency domain data, in accordance with some embodiments of the technology described herein. In particular, the second row of FIG. 11 shows the performance of the neural network model 100 described with reference to FIG. 1A, and the third row of FIG. 11 shows the performance of the neural network model 520 described with reference to FIG. 5B. For both models, FIG. 11 shows the performance of the respective first and second sub-models (sub-models 102 and 120, and sub-models 522 and 510). The first row of FIG. 11 shows the under-sampled and fully-sampled images (both magnitude and phase). As may be seen from FIG. 11, the output of the first sub-model of the neural network model 100 (first two columns in the middle row) has improved quality with fewer artifacts, which is also indicated by the increased peak SNR (PSNR). The output of the second sub-model of the neural network model 100 (last two columns in the middle row) shows that the second sub-model further improves the reconstruction by increasing the contrast of the magnitude image and generating a smoother phase map, which is closer to that of the fully sampled image. For the neural network model 520, the second sub-model contributes less to the improvement as reflected by PSNR than the first sub-model. The situation is reversed for the first neural network sub-model.

Figure 12:
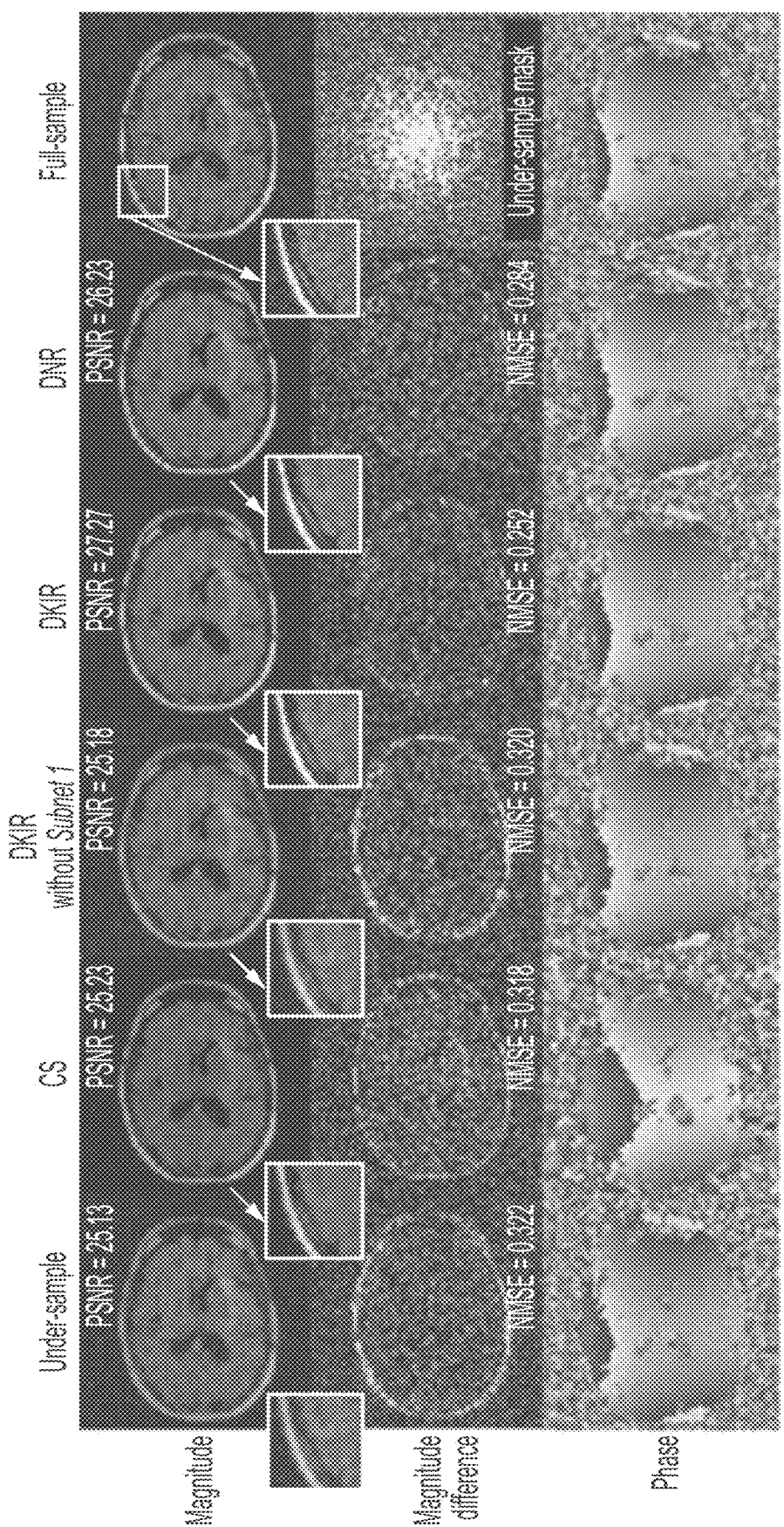
FIG. 12 further illustrates performance of some of the neural network models for generating MR images from under-sampled spatial frequency domain data, in accordance with some embodiments of the technology described herein.

FIG. 12 further illustrates performance of some of the neural network models for generating MR images from under-sampled spatial frequency domain data, in accordance with some embodiments of the technology described herein. In particular, FIG. 12 illustrates the performance of some of the neural networks developed herein relative to other techniques on images under-sampled down to 33% of the number of samples required by the Nyquist sampling rate. The performance of the neural network models 100 and 520 (shown in fourth and fifth columns of FIG. 12) was compared to that of compressed sensing (implemented using the ADMM regularizer, with regularization parameter=5e-3, and shown in the second column of FIG. 12) and neural network model 100 without the first sub-model (shown in the third column of FIG. 12). Normalized mean squared error and peak-SNR were measured to quantify the difference of output images. As shown in the FIG. 12, under-sampling introduces blurring and inhomogeneous artifacts. The compressed sensing approach removes the artifacts, but over-smooths the image, and alters the phase image. The model 100 without its first sub-model failed to recover the image. By contrast, the neural network models 100 and 520, output MR images that are much closer in both magnitude and phase to the fully sampled image, as reflected by higher PSNR and lower normalized MSF than competing methods.

As discussed herein, the inventors have developed neural network models for reconstructing MR images from spatial frequency data obtained using non-Cartesian sampling trajectories.

Figure 13A:
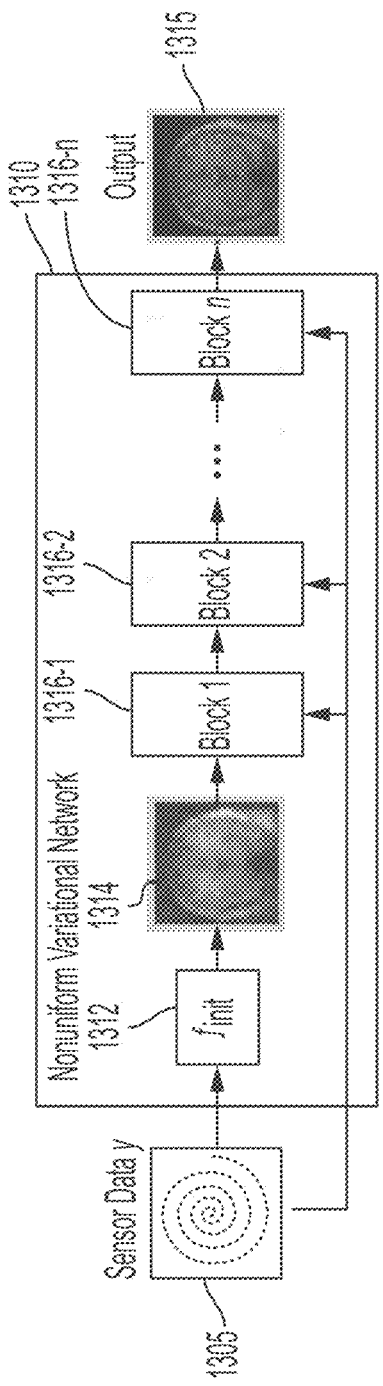
FIG. 13A is a diagram of an illustrative architecture of an example neural network model for generating MR images from input MR spatial frequency data, in accordance with some embodiments of the technology described herein.

FIG. 13A is a diagram of an illustrative architecture of an example neural network model 1310 for generating MR images from input MR spatial frequency data, in accordance with some embodiments of the technology described herein. As shown in FIG. 13A, neural network model 1310 reconstructs output MR image 1315 from input MR spatial frequency data 1305 by processing the input MR spatial frequency data in stages. First, the input MR spatial frequency data 1305 is processed using initial processing block 1312 to produce an initial image 1314, and then the initial image 1314 is processed by a series of neural network blocks 1316-1, 1316-2, . . . , 1316-n.

In some embodiments, one or more of the blocks 1316-1, 1316-2, . . . , 1316-n may operator in the image domain. In some embodiments, one or more of the blocks 1316-1, 1316-2, . . . , 1316-n may transform the input data to a different domain, including but not limited to the spatial frequency domain, perform processing (e.g., reconstruction processing) in the different domain, and subsequently transform back to the image domain.

In some embodiments, the initializer block transforms the input MR spatial frequency data to the image domain to generate an initial image for subsequent processing by the neural network model 1310. The initializer block may be implemented in any suitable way. For example, in some embodiments, the initializer block may apply the adjoint non-uniform Fourier transformation to the input MR spatial frequency data to obtain the initial image. As another example, in some embodiments, the initializer block may apply the gridding reconstruction to the input MR spatial frequency data to obtain the initial image.

Figure 13B:
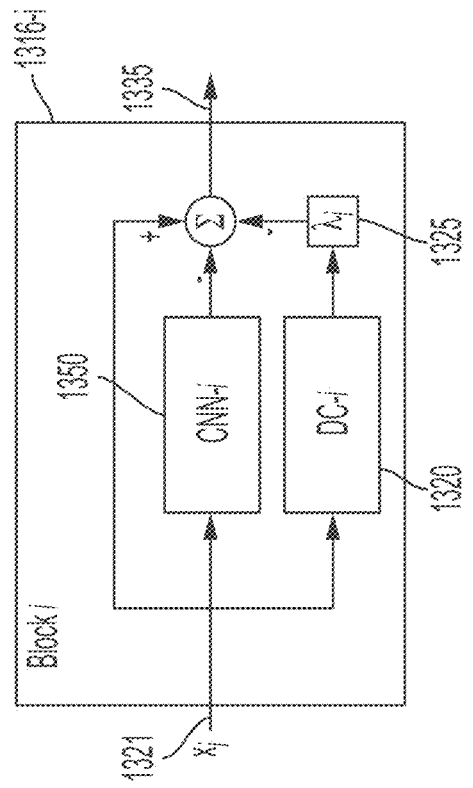
FIG. 13B is a diagram of one type of architecture of a block of the neural network model of FIG. 13A, in accordance with some embodiments of the technology described herein.
Figure 13C:
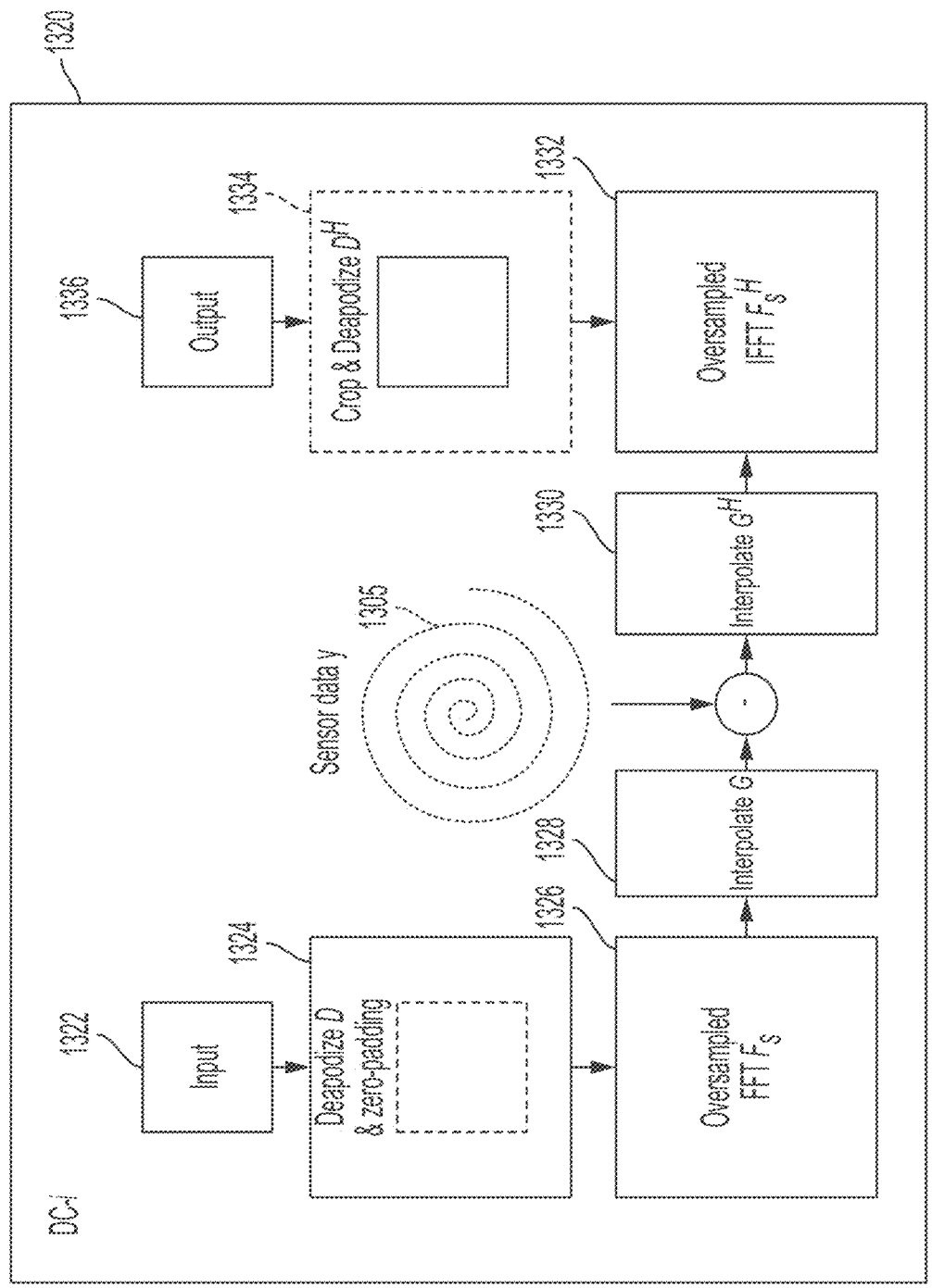
FIG. 13C is a diagram of an illustrative architecture of a data consistency block, which may be part of the block shown in FIG. 13B, in accordance with some embodiments of the technology described herein.
Figure 13D:
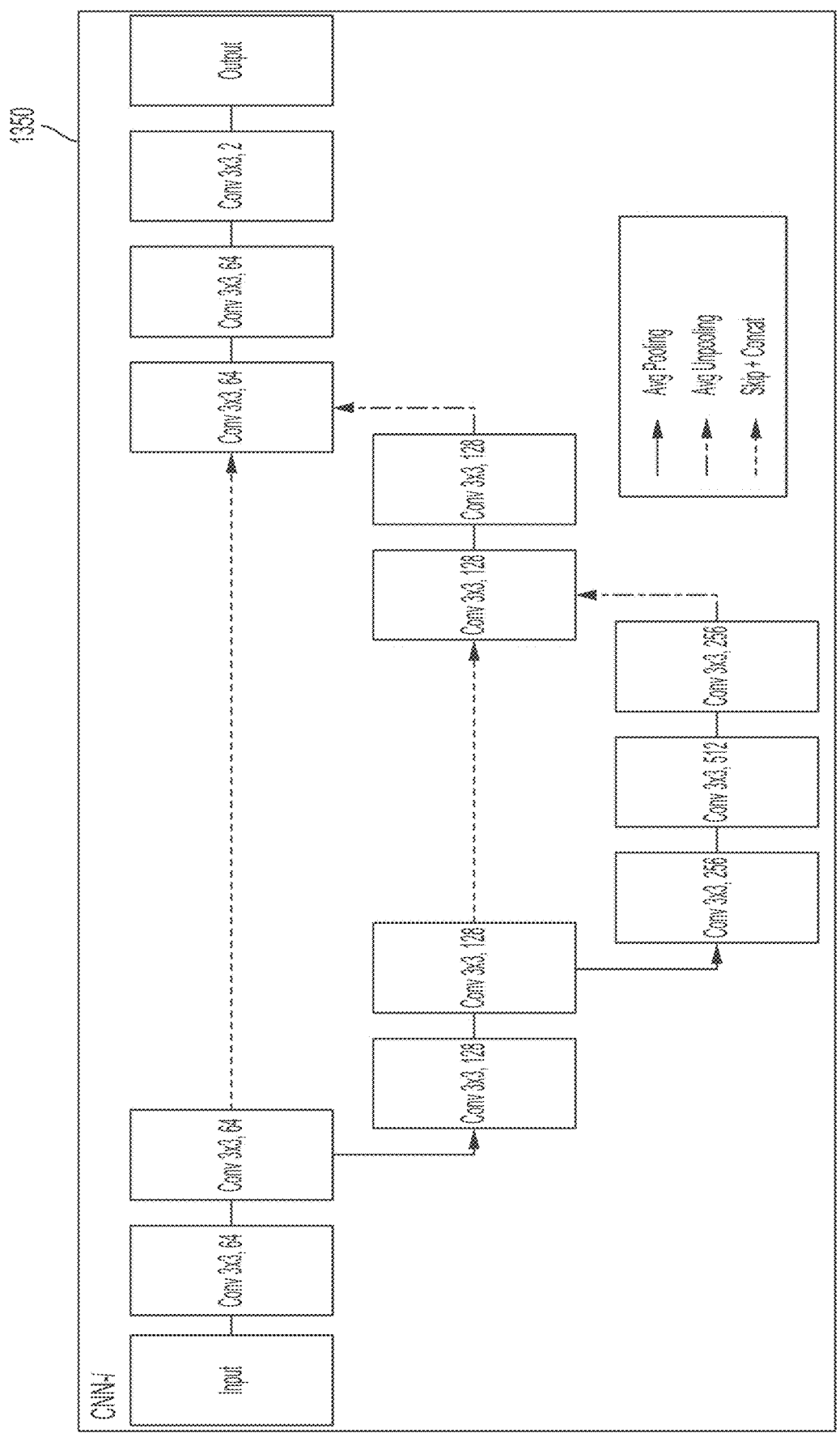
FIG. 13D is a diagram of an illustrative architecture of a convolutional neural network block, which may be part of the block shown in FIG. 13B, in accordance with some embodiments of the technology described herein.
Figure 13E:
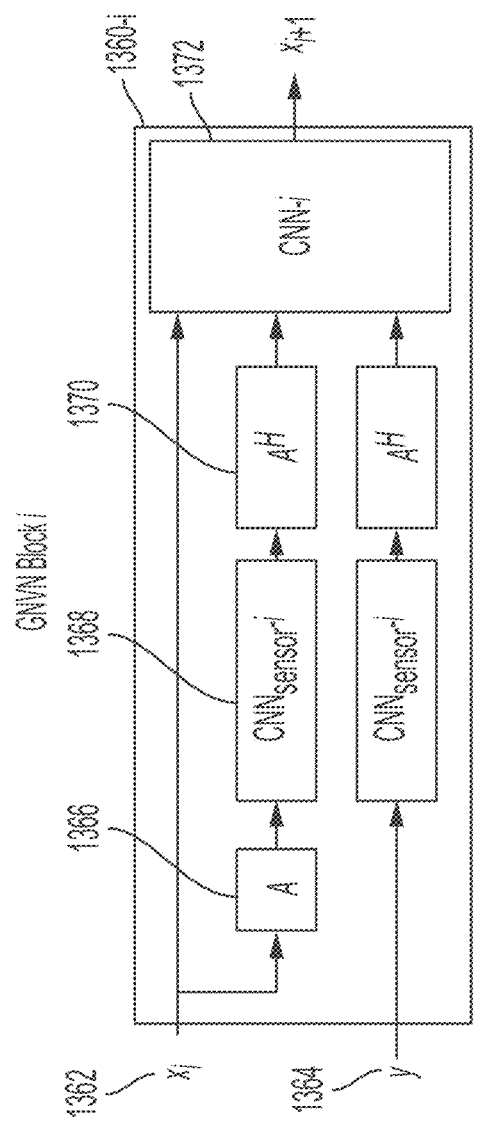
FIG. 13E is a diagram of another type of architecture of a block of the neural network model of FIG. 13A, in accordance with some embodiments of the technology described herein.

Illustrative architectures of neural network blocks 1316 are shown in FIG. 13B (corresponding to a non-uniform variational network) and FIG. 13E (corresponding to a generalized non-uniform variational network). Accordingly, in some embodiments, at least one, at least some, or all of the blocks 1316-1, 1316-2, . . . , 1316-n may have an architecture as shown for illustrative block 1316-$i$ in FIG. 13B. As shown in FIG. 13-B, neural network block 1316-$i$ includes a data consistency block 1320, and a convolutional neural network block 1350, both of which are applied to the input $x_i$, labeled as 1321. The input $x_i$ may represent the MR image reconstruction generated by neural network 1310 at the completion of the $(i-1)^{st}$ neural network block. In this example, the output 1335 of the block 1316-$i$ is obtained by applying the data consistency block 1320 to the input $x_i$ to obtain a first result, applying the convolutional neural network block 1350 to $x_i$, to obtain a second result, and subtracting from $x_i$ a linear combination of the first result and the second result, where the linear combination is calculated using the block-specific weight $\lambda_i$.

The data consistency block 1320 may be implemented in any of numerous ways. In some embodiments, the data consistency block 1320 may perform data consistency processing by transforming the input image represented by $x_i$ to the spatial frequency domain using a non-uniform Fourier transformation, comparing the result with the initial MR spatial frequency data 1305, and transforming the difference between the two hack to the image domain using an adjoint of the non-uniform Fourier transformation.

An illustrative implementation of data consistency block 1320 is shown in FIG. 13C. In the illustrative implementation of FIG. 13C, the image domain input 1322 (which may be the intermediate reconstruction $x_i$ 1321), is transformed to the spatial frequency domain through a series of three transformations 1324, 1326, and 1328, whose composition is used to implement a non-uniform fast Fourier transformation from the image domain to the spatial frequency domain. In particular, the transformation 1324 is a de-apodization and zero-padding transformation D, the transformation 1326 is an oversampled FFT transformation $F_s$, and the transformation 1328 is the gridding interpolation transformation G. As described herein, the non-uniform fast Fourier transformation A is represented by the composition of these transformations according to: $A = D\ F_s\ G$. Example realizations of these constituent transformations are described herein.

After the image domain input 1322 is transformed to the spatial frequency domain, it is compared with the initial MR spatial frequency data 1305, and the difference between the two is transformed back to the image domain using the transformations 1330, 1332, and 1334, in that order. The transformation 1330 is the adjoint of the gridding interpolation transformation 1328. The transformation 1332 is the adjoint of the oversampled FFT transformation 1326. The transformation 1334 is the adjoint of the deapodization transformation 1324. In this way, the composition of the transformations 1330, 1332, 1334, which may be written as $G^H F_s^H D^H = A^H$, represents the adjoint $A^H$ of the non-uniform Fourier transformation A.

The convolutional neural network block 1350 may be implemented in any of numerous ways. In some embodiments, the block 1350 may have multiple convolutional layers, including one or more convolutional layers and one or more transpose convolutional layers. In some embodiments, the block 1350 may have a U-net structure, whereby multiple convolutional layers downsample the data and subsequent transpose convolutional layers upsample the data, for example, as shown in the illustrative U-net architecture of FIG. 13D for the block 1350.

As shown in FIG. 13D, input to the convolutional network block 1350 is processing by a downsampling path followed an upsampling path. In the downsampling path, the input is processed by repeated application of two convolutions with 3×3 kernels, each followed by application of a non-linearity (e.g., a rectified linear unit or ReLU), an average 2×2 pooling operation with stride 2 for downsampling. At each downsampling step the number of feature channels is doubled from 64 to 128 to 256. In the upsampling path, the data is processed be repeated upsampling of the feature map using an average unpooling step that halves the number of feature channels, a concatenation with the corresponding feature map from the downsampling path, and two 3×3 convolutions, each followed by application of a non-linearity (e.g., a ReLU).

FIG. 13E is a diagram of another type of architecture of a block of the neural network model of FIG. 13A, in accordance with some embodiments of the technology described herein. A neural network model with blocks having the architecture like the one shown in FIG. 13E may be termed a "generalized non-uniform variational network" or "GNVN". It is "generalized" in the sense that, while data consistency blocks are not used directly, feature similar to the image features generated by such blocks may be useful to incorporate into a neural network model.

As shown in FIG. 13E, the GNVN block 1360-$i$ takes as input: (1) the image domain data $x_i$, labeled as 1362; and (2) the initial MR spatial frequency data 1364. The input $x_i$ may represent the MR image reconstruction generated by neural network 1310 at the completion of the $(i-1)$ GNVN block (1360-$(i-1)$). These inputs to the block 1360-$i$ are then used to generate inputs to the convolutional neural network block 1372 part of block 1360-$i$. In turn, from these inputs, the CNN block 1372 generates the next MR image reconstruction denoted by $x_{i+1}$.

In the embodiment of FIG. 13E, the inputs 1362 and 1364 are used to generate three inputs to the CNN block 1372: (1) the reconstruction $x_i$ itself is provided as input to the CNN block; (2) the result of applying, to the reconstruction $x_i$, the non-uniform Fourier transformation 1366 followed by a spatial frequency domain convolutional neural network 1368, followed by the adjoint non-uniform Fourier transformation 1370; and (3) the result of applying, to the initial MR spatial frequency data 1364, the spatial frequency domain convolutional neural network 1368 followed by an adjoint non-uniform Fourier transform 1370.

In some embodiments, the non-uniform Fourier transformation 1366 may be the transformation A expressed as a composition of three transformations: the de-apodization transformation D, an oversampled Fourier transformation $F_s$, and a local gridding interpolation transformation G such that $A = D\ F_s\ G$. Example realizations of these constituent transformations are described herein.

The spatial frequency domain CNN 1368 may be any suitable type of convolutional neural network. For example, the CNN 1368 may be a five layer convolutional neural network with residual connection. However, in other embodiments, the spatial frequency domain network 1368 may be any other type of neural network (e.g., a fully convolutional neural network, a recurrent neural network, and/or any other suitable type of neural network), as aspects of the technology described herein are not limited in this respect.

A discussion of further aspects and details of neural network models for MR image reconstruction from non-Cartesian data, such as the neural network models illustrated in FIGS. 13A-13E, follows next. First, some notation is introduced. Let $x \in \mathbb{C}^N$ denote a complex-valued MR image to be reconstructed, represented as a vector with $N = N_x N_y$, where $N_x$ and $N_y$ are width and height of the image. Let $y \in \mathbb{C}^M$ ($M \ll N$) represent the undersampled k-space measurements from which the complex-valued MR image x is to be reconstructed. Reconstruct x from y may be formulated as an unconstrained optimization problem according to:

$$\underset{x}{\operatorname{argmin}}\ \frac{\lambda}{2}\|Ax - y\|_2^2 + \mathcal{R}(x), \quad \text{(Eq. 1)}$$

where the operator A is a non-uniform Fourier sampling operator, $\mathcal{R}$ expresses regularisation terms on x, and $\lambda$ is a hyper-parameter associated to the noise level. In the case when the k-space measurements y are obtained using a Cartesian sampling trajectory, the operator A may expressed according to: $A = MF$ where M is a sampling mask, and F is discrete Fourier transform. In the case of a non-Cartesian sampling trajectory, the measurements no longer fall on a uniform k-space grid and the sampling operator A is now given by a non-uniform discrete Fourier transform of type I:

$$y((k_x, k_y)) = \sum_{l=0}^{N_x} \sum_{m=0}^{N_y} x_{lm} e^{2\pi i \left(\frac{l}{N_x} k_x + \frac{m}{N_y} k_y\right)} \quad \text{(Eq. 2)}$$

where $(k_x, k_y) \in \mathbb{R}^2$ (rather than $(k_x, k_y) \in \mathbb{Z}^2$). An efficient implementation of the above forward model may be implemented using the so-called non-uniform Fast Fourier Transform (NUFFT). The idea is to approximate Eq. 2 by the following decomposition: $A = GF_s D$, where G is a gridding interpolation kernel, $F_s$ is fast Fourier transform (FFT) with an oversampling factor of s, and D is a de-apodization weights. This decomposition is described in further detail below.

In contrast, the inversion of A is considerably more involved. For the (approximately) fully-sampled case, one can consider direct inversion ($\mathcal{O}(N^3)$) or a more computationally efficient gridding reconstruction, which has the form $x_{gridding} = A^H W y$, where W is a diagonal matrix used for the density compensation of non-uniformly spaced measurements. For the undersampled case, the inversion is ill-posed, and Eq. 1 should be solved by iterative algorithms.

The inventors have developed a new deep learning algorithm to approximate the solution to the optimization problem of Eq. 1. The approach begins by considering a gradient descent algorithm, which provides a locally optimal solution to Eq. 1, specified by the following equations for initialization and subsequent iterations:

$$x_0 = f_{init}(A, y); \quad \text{(Eq. 3)}$$

$$x_{i+1} = x_i - \alpha_i \nabla_x f(x)_{x=x_i}, \quad \text{(Eq. 4)}$$

where $f_{init}$ is an initializer, $\alpha$ is a step size and $\nabla f$ is the gradient of the objective functional, which is given by:

$$\nabla_x f(x) = \lambda A^H (Ax - y) + \nabla_x \mathcal{R}(x). \quad \text{(Eq. 5)}$$

In some embodiments, the initializer may be selected as the adjoint $f_{init}(A, y) = A^H y$ reconstruction or the gridding reconstruction $f_{init}(A, y) = A^H W y$. The deep learning approach to solving Eq. 1 involves unrolling the sequential updates of Eq. 4 into a feed-forward model, and approximating the gradient term $\nabla \mathcal{R}$ by a series of trainable convolutional (or other types of neural network) layers and non-linearities. This approach results in an end-to-end trainable network with $N_{it}$ blocks given by:

$$x_0 = f_{init-cnn}(A, y \mid \theta_0) \quad \text{(Eq. 6)}$$

$$x_{i+1} = x_i - \lambda_i \underbrace{A^H (Ax_i - y)}_{DC-i} - \underbrace{f_{cnn}(x_i \mid \theta_i)}_{CNN-i} \quad \text{(Eq. 7)}$$

where the learnable parameters are $\{\theta_0, \ldots, \theta_{N_{it}}, \lambda_1, \ldots, \lambda_{N_{it}}\}$. Note that the step size $\alpha_i$ is absorbed in the learnable parameters. In this way, a general non-convex regularization functional is used (e.g., instead of a Fields-of-Experts model), and regularization functional can be approximated by convolutional neural networks. Indeed, the neural network model illustrated in FIGS. 13A-13D is implemented in accordance with Equations 6 and 7. For example, an implementation of the data consistency term DC-i is shown in FIG. 13C and an implementation of the CNN-i term is shown in FIG. 13D.

The inventors have recognized that the computational complexity of such an approach is a function of how the forward operator $A \in \mathbb{C}^{M \times N}$ is implemented because A is large complex-valued matrix that can occupy a lot of memory to store. As described herein, in contrast to the Cartesian case, A is expressed as $GF_s D$. For 2D cases, this can be a large matrix, which consumes a large portion of GPU memory (e.g., for $N = 192^2$ and $M = 10,000$ (i.e., $\approx 3\times$ acceleration), storing the complex-valued matrix alone already takes 3 GB of memory). To overcome this challenge, the inventors have implemented the gridding interpolation transformation G i as a sparse GPU matrix multiplication. $F_s$ is an FFT, where an efficient GPU implementation is available. Finally, D is a diagonal matrix, which can be implemented as a Hadamard product of matrices. The adjoint can similarly be implemented as $A^H = D^H F_s^H G^H$, where $\cdot^H$ is a complex-conjugate transpose.

Further details of the decomposition of the forward operator $A = GF_s D$ are described next. First, some preliminaries. The spatial frequency domain (sometimes referred to as k-space) may be indexed using two-dimensional or three-dimensional coordinates (e.g. $(k_x, k_y)$ or $(k_x, k_y, k_z)$). In this way, each entry of the vector y representing input MR spatial frequency data represents a value associated to a specific coordinate in k-space. A regular grid in k-space refers to a regularly-spaced grid of points k-space such that there is a fixed distance $\Delta$ between each k-space coordinate that can be indexed. Generally, the input MR spatial frequency data y may include k-space samples spaced on a regular-grid or irregularly spaced. Regularly spaced points are sometimes termed Cartesian data points. Irregularly spaced points are sometimes termed non-Cartesian (data) points.

The interpolation transformation G operates to interpolate non-Cartesian sensor data y onto a regular k-space grid. When the transformation is represented as a matrix G, each row in the matrix corresponds to a specific regular grid point in k-space, and the entry j in the row i (i.e., the entry $G_{ij}$) expresses how much weight is associated between ith regular grid and jth k-space sample.

In some embodiments, the interpolation matrix entries may be computed any one of the following four functions:

$$\text{Two term cosine: } \alpha + (1 - \alpha) \cos\left(\frac{2\pi}{W} u\right)$$

$$\text{Three-term cosine: } \alpha + \beta \cos\left(\frac{2\pi}{W} u\right) + (1 - \alpha - \beta) \cos\left(\frac{4\pi}{W} u\right)$$

$$\text{Gaussian: } \exp\left[-\frac{1}{2}\left(\frac{u}{\sigma}\right)^2\right]$$

$$\text{Kaiser-Bessel: } \frac{1}{W} I_0\left[\beta \sqrt{1 - (2u/W)^2}\right]$$

where $\mu$ is a distance between ith regular grid point and jth non-Cartesian data coordinate. The parameters $\alpha$, $\beta$, W, $\sigma$ are free design parameters to be specified by user, and $I_0$ is the zeroth-order modified Bessel function of the first kind. However, it should be appreciated than any other function may be used for computing the interpolation matrix entries instead of or in addition to the example four functions listed above.

In some embodiments, the entries of the interpolation weight matrix may be computing using an optimization approach. For example, the entries may be computed by solving a min-max optimization problem, as shown in Equations 16 and 21 of Fessler, J. A., Sutton B. P.: Non-uniform fast Fourier transforms using min-max interpolation. IEEE Transactions of Signal Processing 51 (2), 560-574 (2003), which is incorporated by reference herein in its entirety. In some embodiments, the Fourier transformation F may be represented by an oversampled Fourier matrix $F_s$, which is a dense matrix in which each entry is a complex exponential of the form $e^{i\gamma}$ for $\gamma$ which depends on the index. The role of this matrix is to perform Fourier transform. In some embodiments, $F_s$ may be implemented using the fast Fourier transform with oversampling factor s. For example, if the image to be reconstructed x is N×N pixels, then oversampling FFT is performed for image size sN×sN.

In some embodiments, the de-apodization transformation may be represented by a matrix D that will weigh each pixel in the image by a corresponding weight to reduce the interpolation error of approximating A with the given decomposition. In some embodiments, this may be implemented via a pixel-wise weighting of the intermediate reconstruction in the image domain. For example, the pixel-wise weighting may be implemented using a spatially-varying low-order smooth polynomial. In some embodiments, the matrix D may be set as discussed in Section IV-C of Fessler, J. A. Sutton B. P.: Non-uniform fast Fourier transforms using min-max interpolation. IEEE Transactions of Signal Processing 51 (2), 560-574 (2003).

The inventors have also appreciated that the network of FIGS. 13A-13D forces a bottleneck at the end of each iteration. However, an alternative view is that the network simply benefits from the image features given by data consistency (DC-i) blocks. This observation motivates a generalized approach where, instead of using a data consistency block, each CNN-i block in the model of FIGS. 13A-13D is provided a concatenation of the following inputs: the intermediate reconstruction $x_i$, the self-adjoint $A^H A x_i$, and the adjoint of the input $A^H y$. Furthermore, one can also consider applying 1D-convolution in raw sensory domain using $f_{sensor-cnn}(\cdot|\phi)$ to exploit the information along the sampling trajectory and remove unnecessary information (e.g. isolatable artifacts or noise). The resulting network shown in FIGS. 13A, 13D, and 13E, is given by:

$$x_0 = f_{init-cnn}(A, f_{sensor-cnn}(y|\phi_0)|\theta_0)x_{i+1}$$
$$f_{cnn}(x_i, A^H f_{sensor-cnn}(Ax_i|\phi_i), x_0|\theta_i),$$

where the learnable parameters are $\{\phi_0, \ldots, \phi_{N_{it}}, \theta_0, \ldots, \theta_{N_{it}}\}$. As described herein, this type of neural network model is termed Generalized Non-uniform Variational Network (GNVN).

The inventors have recognized that some embodiments of neural network architectures described herein may be considered as embodiments of a neural network model that may be expressed according to the following:

$$x_{rec} = f_{rec}(A, y|\theta), \quad (Eq. 8)$$

This general type of neural network model may accepts as input any input that is a combination of the forward operator A and raw spatial frequency domain data y, as well as additional learnable parameters θ, which can be an arbitrary dimension. The parameters θ may be adjusted during training process.

The input to the neural network of Eq. 8 may be data obtained by one or multiple RF coils of an MRI system, as aspects of the technology described herein are not limited to reconstructing images from data collected by a single RF coil. In addition, the input data y may have been obtained using multiple contrasts and/or different sets of acquisition parameters (e.g., by varying repetition time (TR), echo time (TE), flip angle θ, etc.). In some embodiments, input into the network may be, but is not limited to, the raw data y. Additionally or alternatively, the input to the network may be the adjoint reconstruction $A^H y$ where $(\cdot)^H$ is the conjugate transpose of the matrix.

In some embodiments, where the data y includes data collected by multiple RF coils, these data y may be split into $N_{coil}$ n separate data sets, denoted $y^{(i)}$ for i=1, ..., $N_{coil}$·$N_{coil}$ can be any number (e.g., any number in the range of 2-20 such, for example, 8 or 9 or 10). In some such embodiments, the neural network input may be the adjoint reconstruction of each coil images $x_0^{(i)} = A^H y^{(i)}$, and $x_0^{(i)}$ for i=1, ..., $N_{coil}$ can be stacked together and form the input to the network (e.g., to the convolutional layers part of the network).

In some embodiments, the raw data y may include multiple measurements obtained by each of one or more RF coils. For example, if the data is measured multiple times, say $N_{avg}$ times, then these data, or the adjoint reconstruction of these data, or any other function of these data measurements and the forward operator A, may form an input to the neural network. For example, multiple measurements may be obtained for signal averaging and/or as part of acquiring images with different contrast.

In some embodiments, as described above, the input to the neural network of Eq. 8 may be also be any function based on A and/or y. For example, in some embodiments, the gridding reconstruction may be an input to the network. Gridding reconstruction may have the form of $x_0 = A^H W y$, where W is called sample density compensation weights, which is a matrix that scales each element in the vector y.

Any of numerous techniques may be used to compute the sample density compensation weights W. For example, in some embodiments, the weights W may be computed according to: $W = A^H A 1$, where 1 is a vector of ones. As another example, the weights W may be any suitable user-defined function. As yet another example, the weights W may be learned and adjusted during neural network training, in which case the weights may be referred to as learned sample density compensation weights. In some embodiments, the input to the network may be a combination of y and the weights W, whether learned or fixed learnable, without the use of the forward operator A.

It should also be appreciated that the neural network need not operate on the raw data y, and in some embodiments these data may be pre-processed. For example, in some embodiments these data may be pre-processed to perform operations such as interference removal, denoising, filtering, smoothing, image prewhitening, etc. More generally, the network has the form $f(y, A, \theta)$.

With regard to the neural network weights θ, these weights may be initialized in any suitable way as part of the training procedure. For example, the weights may be initialized randomly (e.g., using He initialization following Equation 12 in He, K., et al.: Deep residual learning for image recognition. Proceedings of the IEEE conference on computer vision and pattern recognition (CVPR). pp. 1026-

1034 (2015)). As another example, the network weights may be initialized according to a setting provided by a user. As another example, the network weights may include the learned sampling density weights (e.g., the learned sampling density weights may be a subset of the network weights, the network weights may be initialized using the learned sampling density weights, and all the weights may subsequently be adjusted during training).

With regard to the output $x_{rec}$ of the neural network in Eq. 8, the output may include one or more images per respective RF coil. For example, if the input data contains data from each of $N_{coil}$ RF coils, the output may include one MR image for each such RF coil or multiple MR images for each such coil (e.g., when each coil performs multiple acquisitions, for example, using different contrasts).

In some embodiments, multiple neural networks of the type specified in Eq. 8 may be employed and the output of these networks may be combined such that the multiple neural networks are utilized as an ensemble. The combination may be performed using any suitable type of aggregation rule including, but not limited to, average, weighted averaging, averaging with outlier rejection, and selection of the "best" reconstruction according to a user-defined criterion (e.g., manual inspection, automated selection based on a quantitative metric such as the signal to noise ratio, a perceptual metric, and/or any other suitable metric). Alternatively, in some embodiments, multiple instances of $x_{rec}$ from individual neural networks may be stacked together, and be considered as the output of the network.

As described above, there are numerous possible embodiments of the neural network formulation of Eq. 8 including, but not limited to, the embodiments described herein such as: (1) the non-uniform variational network (NVN) as described herein including with reference to FIGS. 13A-D; (2) the generalized non-uniform variational network (GNVN) as described herein with reference to FIGS. 13A, 13D, and 13E; (3) the Deep K-space Interpolation Reconstruction (DKIR) network as described herein including with reference to FIGS. 1A-C; and (4) the Deep non-local reconstruction (DNR) network as described herein including with reference to FIGS. 5A-5C.

It should be noted that while some of the above described networks architectures include convolutional neural network blocks, other types of blocks may be used in addition to or instead of the convolutional neural network blocks including, for example, residual network, densely connected networks, or squeeze and excitation networks.

In some embodiments, any one of the networks described above may be trained using mean-squared error. For example, in some embodiments, each of the reconstruction blocks in the NVN (e.g., blocks 1316-$i$) or GNVN (e.g., blocks 1360-$i$) architectures may be trained using the mean squared-error criterion according to:

$$\mathcal{L}(\theta) = \sum_{(y,x)\in\mathcal{D}} \|x - x_{rec}\|_2$$

In some embodiments, a reconstruction block can reconstruct each coil-weighted images $x_c$ separately or jointly. It can also attempt to reconstruct each signal $n_{avg}=1, \ldots, N_{avg}$ jointly or separately.

Figure 14:
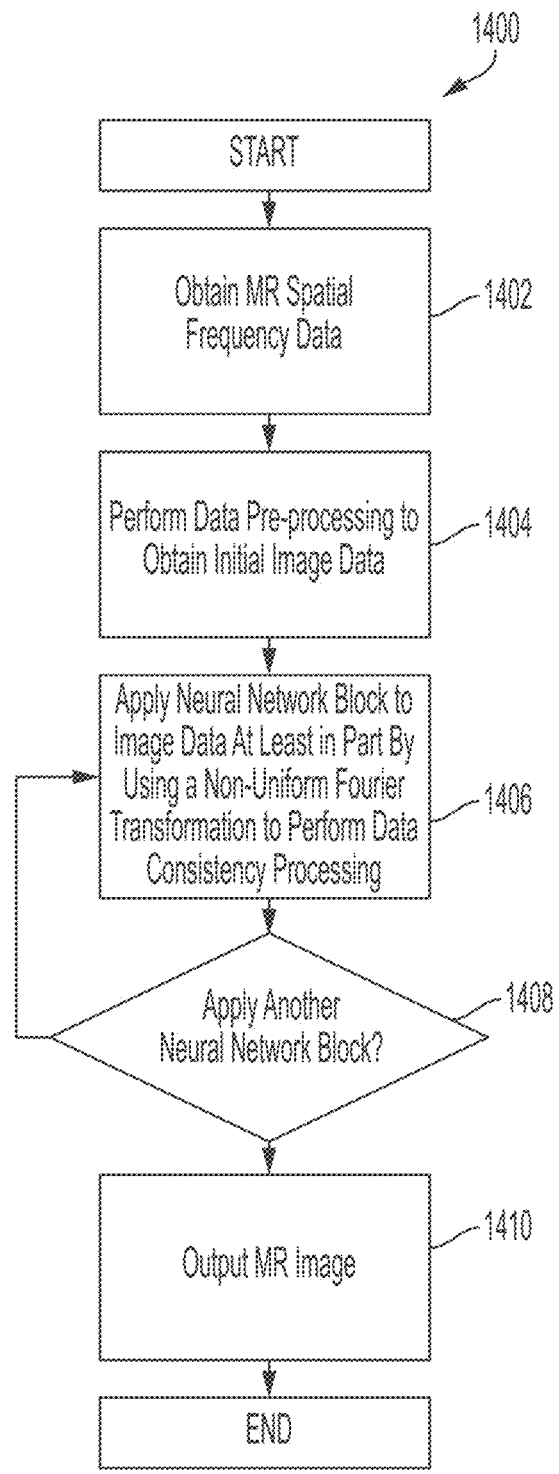
FIG. 14 is a flowchart of an illustrative process 1400 for using a neural network model to generate an MR image from input MR spatial frequency data obtained using non-Cartesian sampling, in accordance with some embodiments of the technology described herein.

FIG. 14 is a flowchart of an illustrative process 1400 for using a neural network model to generate an MR image from input MR spatial frequency data obtained using non-Cartesian sampling, in accordance with some embodiments of the technology described herein. In some embodiments, process 1400 may be performed using a non-uniform variational network (e.g., the neural network described with reference to FIGS. 13A-D), a generalized non-uniform variation network (e.g., the neural network described with reference to FIGS. 13A, 13D, and 13E), or any other suitable type of neural network model.

In some embodiments, the illustrative process 1400 may be performed using any suitable computing device. For example, in some embodiments, the process 1400 may be performed by a computing device co-located (e.g., in the same room as) with an MRI system that obtained the input MR spatial frequency data by imaging a subject. As another example, in some embodiments, the process 1400 may be performed by one or more processors located remotely from the MRI system (e.g., as part of a cloud computing environment) that obtained the input spatial frequency data by imaging a subject.

Process 1400 begins at act 1402, where input MR spatial frequency data is obtained. In some embodiments, the input MR spatial frequency data had been previously obtained by an MRI system and stored for subsequent analysis, so that it is accessed at act 1402. In other embodiments, the input MR spatial frequency data may be obtained by an MRI system (including any of the MRI systems described herein) as part of process 1400. Regardless of when an MRI system performed the imaging to obtain the input MR spatial frequency data, the data may have been obtained using a non-Cartesian sampling trajectory, examples of which are provided herein.

Next, process 1400 proceeds to act 1404, where the input MR spatial frequency data may be pre-processed to obtain an initial image reconstruction. For example, in some embodiments, the input MR spatial frequency data may be transformed to the image domain by using a non-uniform Fourier transformation. For example, the input MR spatial frequency data y may be transformed to the image domain using the adjoint operator $A^H$ described herein (e.g., by computing $A^H y$). As another example, the input MR spatial frequency data may be transformed to the image domain using a gridding reconstruction such as $A^H W y$, where the matrix W is a sampling density compensation matrix that could be: the matrix $A^H A 1$, where 1 is a vector of one's, a user-specified matrix, a matrix learned during training, and/or any suitable combination thereof. In the illustrative example of FIG. 13A, the pre-processing may be performed by the initial processing block 1312.

In some embodiments, the initializer block transforms the input MR spatial frequency data to the image domain to generate an initial image for subsequent processing by the neural network model 1310. The initializer block may be implemented in any suitable way. For example, in some embodiments, the initializer block may apply the adjoint non-uniform Fourier transformation to the input MR spatial frequency data to obtain the initial image. As another example, in some embodiments, the initializer block may apply the gridding reconstruction to the input MR spatial frequency data to obtain the initial image.

Next, process 1400 proceeds to act 1406, where a block of a neural network model is applied to the initial image obtained at act 1404 (or to the current image data when act 1406 is being executed on a return path from decision block 1408 after one or more neural network blocks have already been applied to the initial image). In some embodiments, the block of the neural network model may be configured to perform data consistency processing by using a non-uniform Fourier transformation to take into account the initial MR spatial frequency data obtained at act 1402. This may be done in any suitable way. For example, in some embodiments, the data consistency processing may be performed by a data consistency block such as block 1316-*i* described with reference to FIG. 13B. In such a block, data consistency processing involves transforming intermediate reconstructions transformed to the spatial frequency domain using a non-uniform Fourier transformation and comparing the result to the input MR spatial frequency data. As another example, in some embodiments, the data consistency processing may be performed by transforming the input MR spatial frequency data to the image domain using the non-uniform Fourier transformation and providing the result as input to one or more convolutional blocks as is done, for example, in neural network block 1360-*i* described with reference to FIG. 13E.

Next, process 1400 proceeds to decision block 1408 where it is determined whether another neural network block is to be applied. If it is determined that another block is to be applied, process 1400 returns to act 1406, where another neural network block is applied to the image data generated at the completion of the last iteration of block 1406. Otherwise, this image data is output as the final reconstructed MR image at act 1410.

The inventors have evaluated the performance of the neural network architectures described herein including with reference to FIGS. 13A-E and 14 on real-world MR images. The details of these experiments are described next.

As part of the experiments, 640 randomly selected T1-weighted and T2-weighted brain images were obtained from Human Connectome Project (https:///www.humanconnectome.org/study/hcp-young-adult/document/1200-subjects-data-release). Six hundred of the images were used for training the neural network, while 40 of the images were used for evaluating the performance of the trained neural network. To perform a realistic simulation, a number of pre-processing steps were performed. First, since only magnitude images were provided from the Human Connectome Project, complex-valued images were created by adding phase information to the magnitude data using two-dimensional Fourier bases with randomly sampled low order coefficients. Second, the images were multiplied by spatially localized complex coil sensitivity profiles, which was derived from an analytical model of an MRI RF coil. Finally, a realistic amount of noise observable for parallel image acquisition was added to the images. For the experiments, the images were resampled to a field of view (FOV) of 180×180×180 mm$^3$, with the isotrophic resolution of 3.4× 3.4×3.4 mm$^3$, 1.7×1.7×1.7 mm$^3$ and 1.15×1.15×1.15 mm$^3$, resulting in the matrix sizes 64$^3$, 128$^3$ and 192$^3$, respectively.

In these experiments, single coil reconstruction is evaluated in order to study the behavior of non-uniform MR data reconstruction. The MR data was under-sampled using 2D non-uniform variable density, where the sampling density decays from the k-space center at quadratic speed. For each matrix size, the sampling trajectory with the target acceleration factor R∈{2, 4} was generated. For evaluation, we measured mean squared error (MSE), structural similarity index measurement (SSIM), and peak signal-to-noise ratio (PSNR).

The techniques developed herein were developed with a number of conventional techniques that have been applied to non-uniform MR data including: (1) AUTOMAP (Zhu B., et al.: Image reconstruction by domain-transform manifold learning. Nature 555 (7697), 487 (2018)); (2) image domain U-net (Han, Y., et al.: Deep learning with domain adaptation for acceleration projection-reconstruction MR. Magnetic resonance in medicine 80 (3), 118-1205 (2018)); and (3) k-space domain U-net. Id. All deep learning methods were trained using MSE. Due to its high GPU memory requirements, AUTOMAP was trained only for the matrix size of 64×64. For the NVN approach having the architecture shown in FIGS. 13A-D, a U-net with 3 levels of downsampling (see e.g., FIG. 13D) for each convolutional sub-block. $N_{it}$=5 blocks was used for the number of blocks, and the adjoint $A^H y$ was used for $f_{init}$. For the GNVN approach, a 5-layer convolutional neural network was used $f_{sensor-cnn}$. Each network was trained for 8,000 epochs using Adam optimizer with α=10$^{-4}$, β$_1$=0.9, β$_2$=0.999. All methods were implemented in TensorFlow.

Results of the evaluations are summarized in Table 1 below. The NVN and GNVN approaches developed by the inventors consistently outperformed the baseline approaches for both acceleration factors. AUTOMAP and k-space U-net both underperformed compared to other methods.

TABLE 1

Quantitative result for acceleration factor (R) 2 and 4. For each metric, mean and standard deviation is computed. For mean squared error (MSE), the values are scaled by 10$^3$.

|  | Methods | R = 2 MSE | SSIM | PSNR | R = 4 MSE | SSIM | PSNR |
| --- | --- | --- | --- | --- | --- | --- | --- |
| 64 × 64 | AUTOMAP | 2.40 (42.14) | 0.87 (0.14) | 29.87 (3.73) | 2.59 (8.09) | 0.84 (0.14) | 28.36 (3.51) |
| 64 × 64 | U-net | 1.53 (18.13) | 0.92 (0.11) | 31.44 (3.86) | 2.25 (21.87) | 0.90 (0.10) | 29.81 (3.74) |
| 64 × 64 | U-net (k) | 1.91 (7.40) | 0.86 (0.13) | 30.07 (3.57) | 2.51 (6.58) | 0.81 (0.13) | 28.48 (3.34) |
| 64 × 64 | NVN | 1.22 (12.51) | 0.93 (0.11) | 32.33 (3.92) | 1.38 (4.04) | 0.92 (0.09) | 30.95 (3.62) |
| 64 × 64 | GNVN | 1.22 (16.88) | 0.93 (0.09) | 32.54 (4.00) | 1.37 (4.58) | 0.92 (0.08) | 31.08 (3.66) |
| 128 × 128 | U-net | 0.75 (3.73) | 0.94 (0.09) | 34.06 (3.68) | 0.91 (4.10) | 0.94 (0.07) | 32.76 (3.50) |
| 128 × 128 | U-net (k) | 1.02 (1.26) | 0.89 (0.10) | 32.51 (3.58) | 1.54 (13.77) | 0.87 (0.11) | 31.32 (3.48) |
| 128 × 128 | NVN | 0.57 (0.86) | 0.95 (0.06) | 34.68 (3.57) | 0.82 (1.07) | 0.93 (0.07) | 32.95 (3.54) |
| 128 × 128 | GNVN | 0.58 (1.99) | 0.95 (0.07) | 34.83 (3.64) | 0.67 (0.79) | 0.95 (0.03) | 33.65 (3.47) |
| 192 × 192 | U-net | 0.47 (1.55) | 0.96 (0.05) | 35.68 (3.67) | 0.67 (1.13) | 0.94 (0.07) | 33.71 (3.23) |
| 192 × 192 | U-net (k) | 0.77 (0.81) | 0.89 (0.10) | 33.83 (3.62) | 1.31 (7.53) | 0.87 (0.11) | 31.84 (3.35) |
| 192 × 192 | NVN | 0.40 (0.60) | 0.96 (0.06) | 36.11 (3.60) | 0.66 (1.40) | 0.91 (0.12) | 34.01 (3.43) |
| 192 × 192 | GNVN | 0.40 (0.77) | 0.96 (0.05) | 36.15 (3.57) | 0.52 (0.44) | 0.96 (0.03) | 34.36 (3.07) |

Figure 15A:
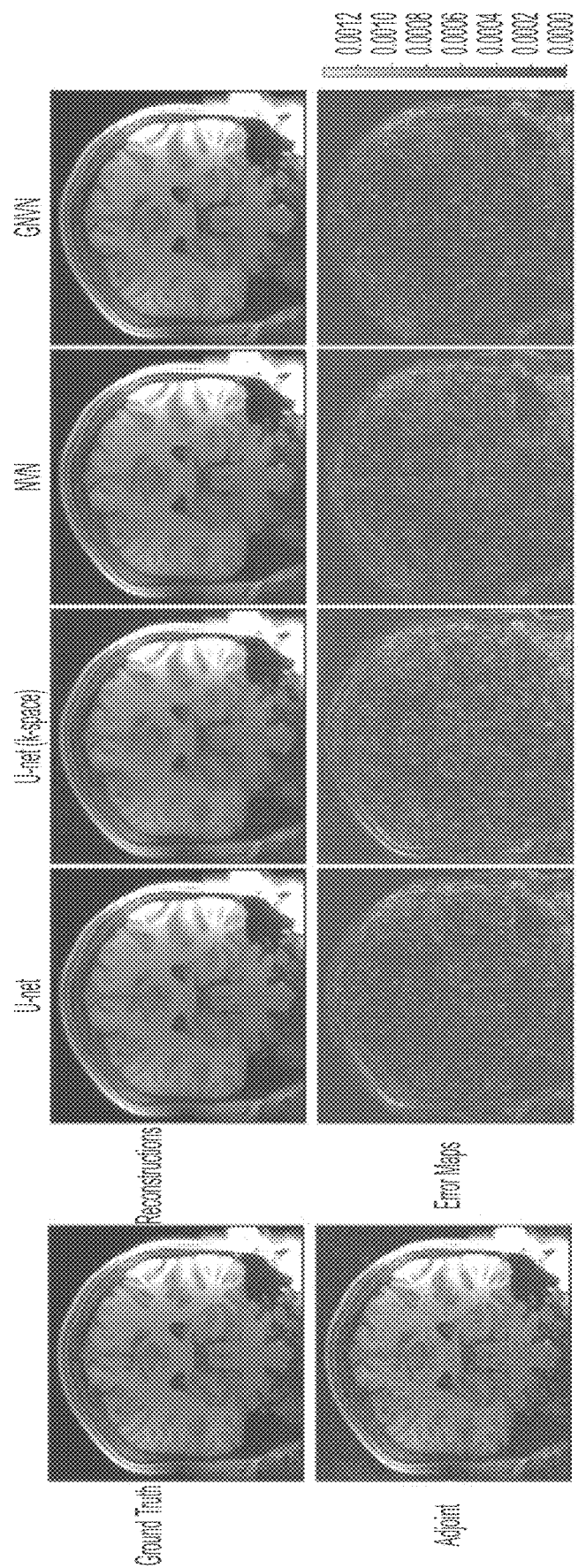
FIG. 15A illustrates T1-weighted MR images reconstructed by using conventional neural network models and neural network models, in accordance with some embodiments of the technology described herein.
Figure 15B:
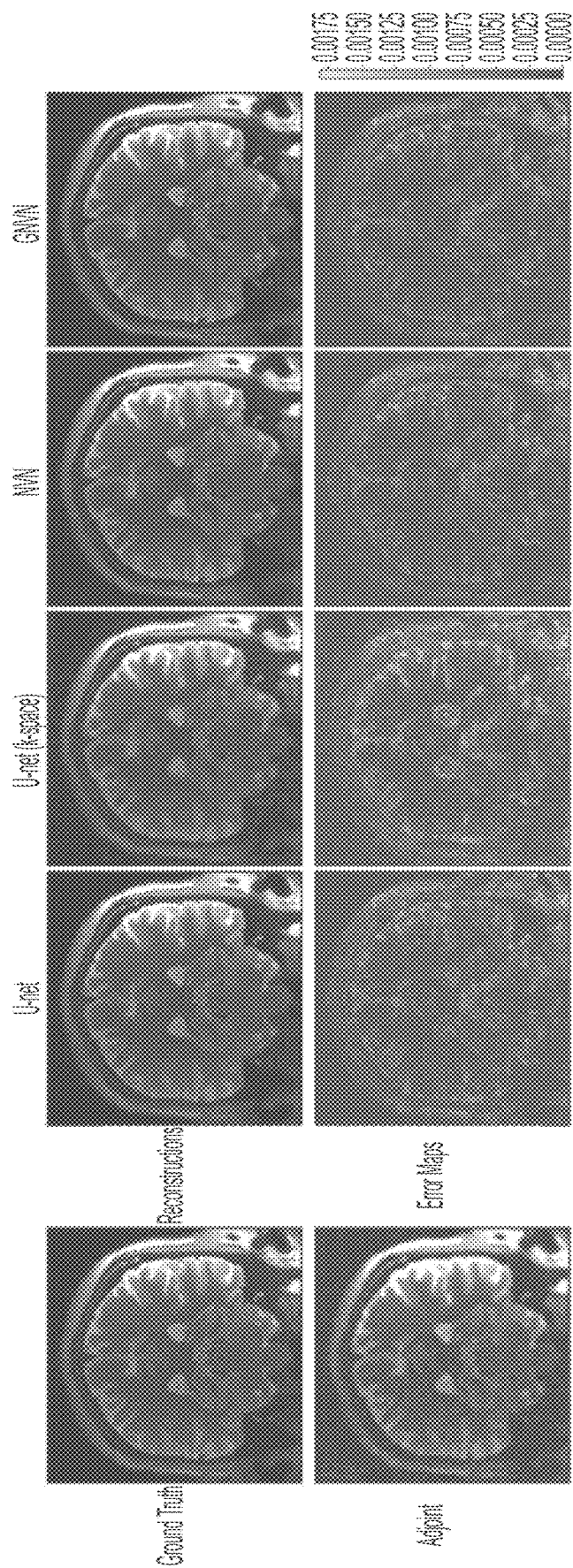
FIG. 15B illustrates T2-weighted MR images reconstructed by using conventional neural network models and neural network models, in accordance with some embodiments of the technology described herein.
Figure 15C:
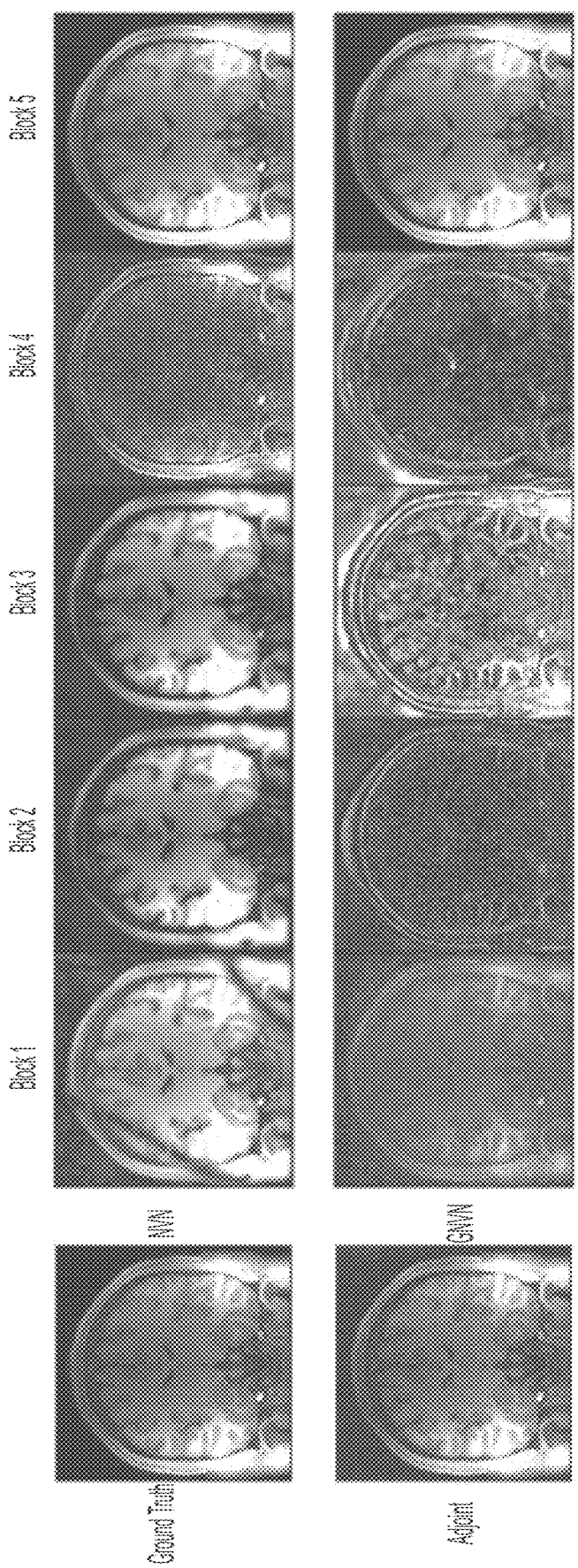
FIG. 15C illustrates reconstructed MR images at different stages of processing by neural network models, in accordance with some embodiments of the technology described herein.

As between the NVN and GNVN approaches, while the NVN approach showed higher data fidelity (lower mean-squared error), the GNVN approach offered better values for PSNR and SSIM. The sample reconstructions of T1-weighted image for R=2 and T2-weighted image for R=4 is shown in FIG. 15A and FIG. 15B respectively. While the overall differences between U-net, NVN and GNVN were small, the reconstructions from NVN and GNVN resulted in lower error, owing to the data consistency processing. GNVN resulted in the lowest overall errors and preserved more of the fine details. Nevertheless, a certain level of blurriness can be observed in all images, due to the added noise. Again, U-net (k-space) for single coil resulted in a suboptimal reconstruction qualitatively. In FIG. 15C, we visualize the output of NVN and GNVN at each block. Interestingly, unlike compressed sensing methods, the intermediate image can diverge from the final image. This is unsurprising as there was no constraint to enforce such behavior. For NVN, most output of each block seems closer to the ground truth, presumably because the output of the DC-i and CNN-i blocks are explicitly combined. In comparison, GNVN showed more interesting features for all the intermediate stages, mainly highlighting the high frequency information.

In these experiments, the number of parameters were 128.1M, 22.0M, 6.6M and 7.3M for AUTOMAP (64×64), U-net, NVN and GNVN respectively. The reconstruction speed were 5.928±0.020 ms, 19.145±0.072 ms, 19.459±0.077 ms, 44.934±0.088 ms, and 65.520±0.100 ms for AUTOMAP (for the image size $64^3$), U-net, U-net (k-space), NVN and GNVN respectively for the image size $192^3$.

Figure 16:
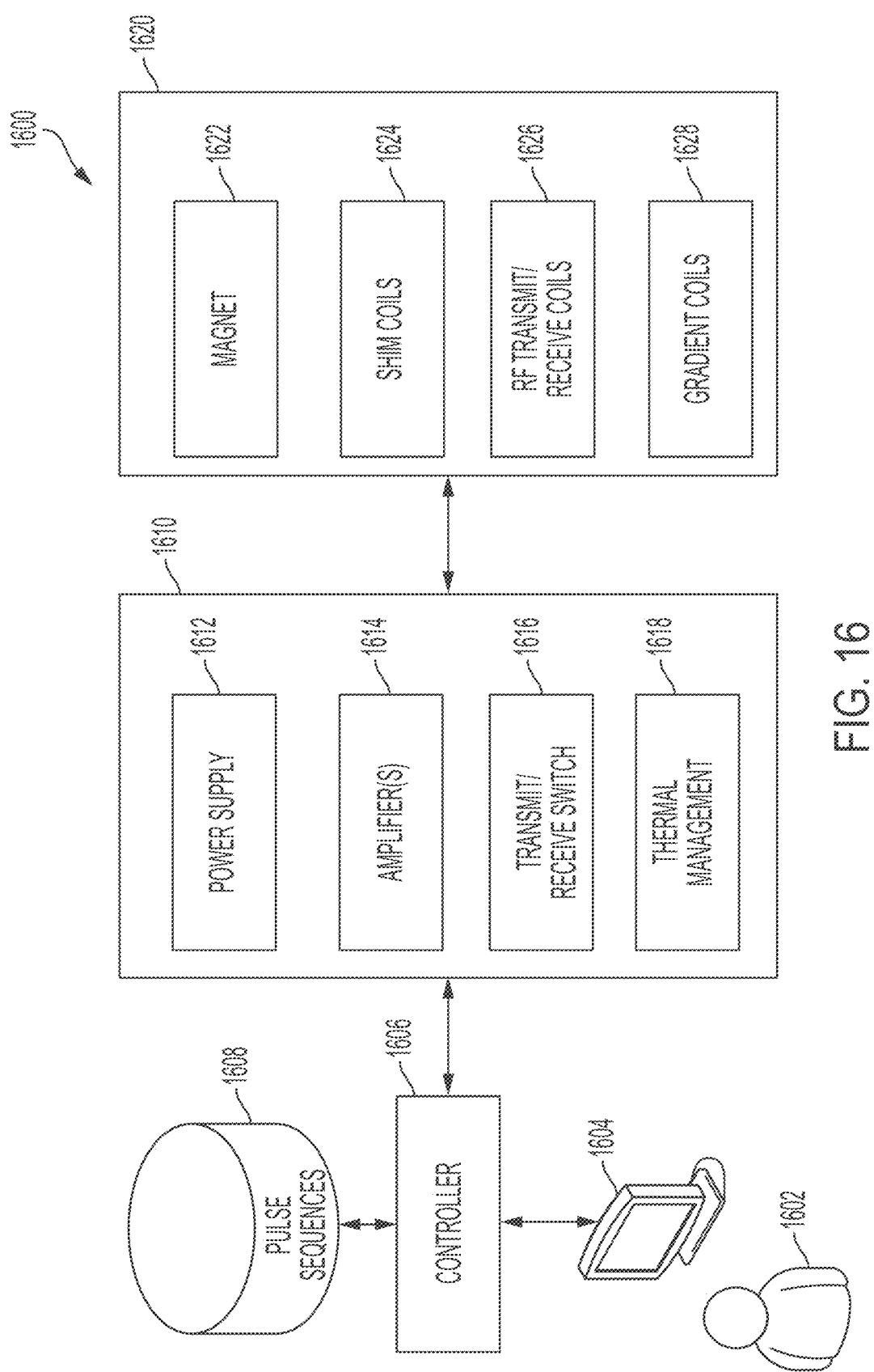
FIG. 16 is a schematic illustration of a low-field MRI system, in accordance with some embodiments of the technology described herein.

FIG. 16 is a block diagram of exemplary components of a MRI system 1600. In the illustrative example of FIG. 16, MRI system 1600 comprises workstation 1604, controller 1606, pulse sequences store 1608, power management system 1610, and magnetic components 1620. It should be appreciated that system 1600 is illustrative and that an MRI system may have one or more other components of any suitable type in addition to or instead of the components illustrated in FIG. 16.

As illustrated in FIG. 16, magnetic components 1620 comprises $B_0$ magnet 1622, shim coils 1624, RF transmit and receive coils 1626, and gradient coils 1628. $B_0$ magnet 1622 may be used to generate, at least in part, the main magnetic field $B_0$. $B_0$ magnet 1622 may be any suitable type of magnet that can generate a main magnetic field (e.g., a low-field strength of approximately 0.2 T or less), and may include one or more $B_0$ coils, correction coils, etc. Shim coils 1624 may be used to contribute magnetic field(s) to improve the homogeneity of the $B_0$ field generated by magnet 1622. Gradient coils 1628 may be arranged to provide gradient fields and, for example, may be arranged to generate gradients in the magnetic field in three substantially orthogonal directions (X, Y, Z) to localize where MR signals are induced.

RF transmit and receive coils 1626 may comprise one or more transmit coils that may be used to generate RF pulses to induce a magnetic field $B_1$. The transmit/receive coil(s) may be configured to generate any suitable type of RF pulses configured to excite an MR response in a subject and detect the resulting MR signals emitted. RF transmit and receive coils 1626 may include one or multiple transmit coils and one or multiple receive coils. The configuration of the transmit/receive coils varies with implementation and may include a single coil for both transmitting and receiving, separate coils for transmitting and receiving, multiple coils for transmitting and/or receiving, or any combination to achieve single channel or parallel MRI systems. Thus, the transmit/receive magnetic component is often referred to as Tx/Rx or Tx/Rx coils to generically refer to the various configurations for the transmit and receive component of an MRI system.

Each of magnetics components 1620 may be of any suitable type and may be constructed in any suitable way. For example, in some embodiments, the $B_0$ magnet 1622 may be an electromagnet or a permanent magnet (e.g., as described below with reference to FIGS. 17A-B and 18A-B). As another example, in some embodiments, one or more magnetics components 1620 (e.g., shim coils 1624 and/or gradient coils 1628) may be fabricated using the laminate techniques.

Power management system 1610 includes electronics to provide operating power to one or more components of the low-field MRI system 1600. For example, power management system 1610 may include one or more power supplies, gradient power amplifiers, transmit coil amplifiers, and/or any other suitable power electronics needed to provide suitable operating power to energize and operate components of the low-field MRI system 1600.

As illustrated in FIG. 16, power management system 1610 comprises power supply 1612, amplifier(s) 1614, transmit/receive switch 1616, and thermal management components 1618. Power supply 1612 includes electronics to provide operating power to magnetic components 1620 of the low-field MRI system 1600. For example, in some embodiments, power supply 1612 may include electronics to provide operating power to one or more $B_0$ coils (e.g., $B_0$ magnet 1622) to produce the main magnetic field for the low-field MRI system, one or more shim coils 1624, and/or one or more gradient coils 1628. In some embodiments, power supply 1612 may be a unipolar, continuous wave (CW) power supply, however, any suitable power supply may be used. Transmit/receive switch 1616 may be used to select whether RF transmit coils or RF receive coils are being operated.

In some embodiments, amplifier(s) 1614 may include one or more RF receive (Rx) pre-amplifiers that amplify MR signals detected by one or more RF receive coils (e.g., coils 1624), one or more RF transmit (Tx) amplifiers configured to provide power to one or more RF transmit coils (e.g., coils 1626), one or more gradient power amplifiers configured to provide power to one or more gradient coils (e.g., gradient coils 1628), and/or one or more shim amplifiers configured to provide power to one or more shim coils (e.g., shim coils 1624).

In some embodiments, thermal management components 1618 provide cooling for components of low-field MRI system 1600 and may be configured to do so by facilitating the transfer of thermal energy generated by one or more components of the low-field MRI system 1600 away from those components. Thermal management components 1618 may include, without limitation, components to perform water-based or air-based cooling, which may be integrated with or arranged in close proximity to MRI components that generate heat including, but not limited to, $B_0$ coils, gradient coils, shim coils, and/or transmit/receive coils. Thermal management components 1618 may include any suitable heat transfer medium including, but not limited to, air and water, to transfer heat away from components of the low-field MRI system 1600.

As illustrated in FIG. 16, low-field MRI system 1600 includes controller 1606 (also referred to as a console) having control electronics to send instructions to and receive information from power management system 1610. Controller 1606 may be configured to implement one or more pulse sequences, which are used to determine the instructions sent to power management system 1610 to operate the magnetic components 1620 in a desired sequence. For example, controller 1606 may be configured to control the power management system 1610 to operate the magnetic components 1620 in accordance with a balanced steady-state free precession (bSSFP) pulse sequence, a low-field gradient echo pulse sequence, a low-field spin echo pulse sequence, a low-field inversion recovery pulse sequence, arterial spin labeling, diffusion weighted imaging (DWI), and/or any other suitable pulse sequence. Controller 1606 may be implemented as hardware, software, or any suitable combination of hardware and software, as aspects of the disclosure provided herein are not limited in this respect.

In some embodiments, controller 1606 may he configured to implement a pulse sequence by obtaining information about the pulse sequence from pulse sequences repository 1608, which stores information for each of one or more pulse sequences. Information stored by pulse sequences repository 1608 for a particular pulse sequence may be any suitable information that allows controller 1606 to implement the particular pulse sequence. For example, information stored in pulse sequences repository 1608 for a pulse sequence may include one or more parameters for operating magnetics components 1620 in accordance with the pulse sequence (e.g., parameters for operating the RF transmit and receive coils 1626, parameters for operating gradient coils 1628, etc.), one or more parameters for operating power management system 1610 in accordance with the pulse sequence, one or more programs comprising instructions that, when executed by controller 1606, cause controller 1606 to control system 1600 to operate in accordance with the pulse sequence, and/or any other suitable information. Information stored in pulse sequences repository 1608 may be stored on one or more non-transitory storage media.

As illustrated in FIG. 16, in some embodiments, controller 1606 may interact with computing device 1604 programmed to process received MR data (which, in some embodiments, may be spatial frequency domain MR data). For example, computing device 1604 may process received MR data to generate one or more MR images using any suitable image reconstruction process(es) including using any of the techniques described herein that make use of neural network models to generate MR images from spatial frequency MR data. For example, computing device 1604 may perform any of the processes described herein with reference to FIGS. 2A, 2B, 2C, 2D, and 14. Controller 1606 may provide information about one or more pulse sequences to computing device 1604 for the processing of data by the computing device. For example, controller 1606 may provide information about one or more pulse sequences to computing device 1604 and the computing device may perform an image reconstruction process based, at least in part, on the provided information.

In some embodiments, computing device 1604 may be any electronic device or devices configured to process acquired MR data and generate one or more images of the subject, being imaged. In some embodiments, computing device 1604 may include a fixed electronic device such as a desktop computer, a server, a rack-mounted computer, or any other suitable fixed electronic device that may be configured to process MR data and generate one or more images of the subject being imaged. Alternatively, computing device 1604 may be a portable device such as a smart phone, a personal digital assistant, a laptop computer, a tablet computer, or any other portable device that may be configured to process MR data and generate one or images of the subject being imaged. In some embodiments, computing device 1304 may comprise multiple computing devices of any suitable type, as the aspects of the technology described herein are not limited in this respect.

In some embodiments, a user 1602 may interact with computing device 1604 to control aspects of the low-field MR system 1600 (e.g., program the system 1600 to operate in accordance with a particular pulse sequence, adjust one or more parameters of the system 1600, etc.) and/or view images obtained by the low-field MR system 1600. According to some embodiments, computing device 1604 and controller 1606 form a single controller, while in other embodiments, computing device 1604 and controller 1606 each comprise one or more controllers. It should be appreciated that the functionality performed by computing device 1604 and controller 1606 may be distributed in any way over any combination of one or more controllers, as the aspects of the technology described herein are not limited for use with any particular implementation or architecture.

Figure 17A:
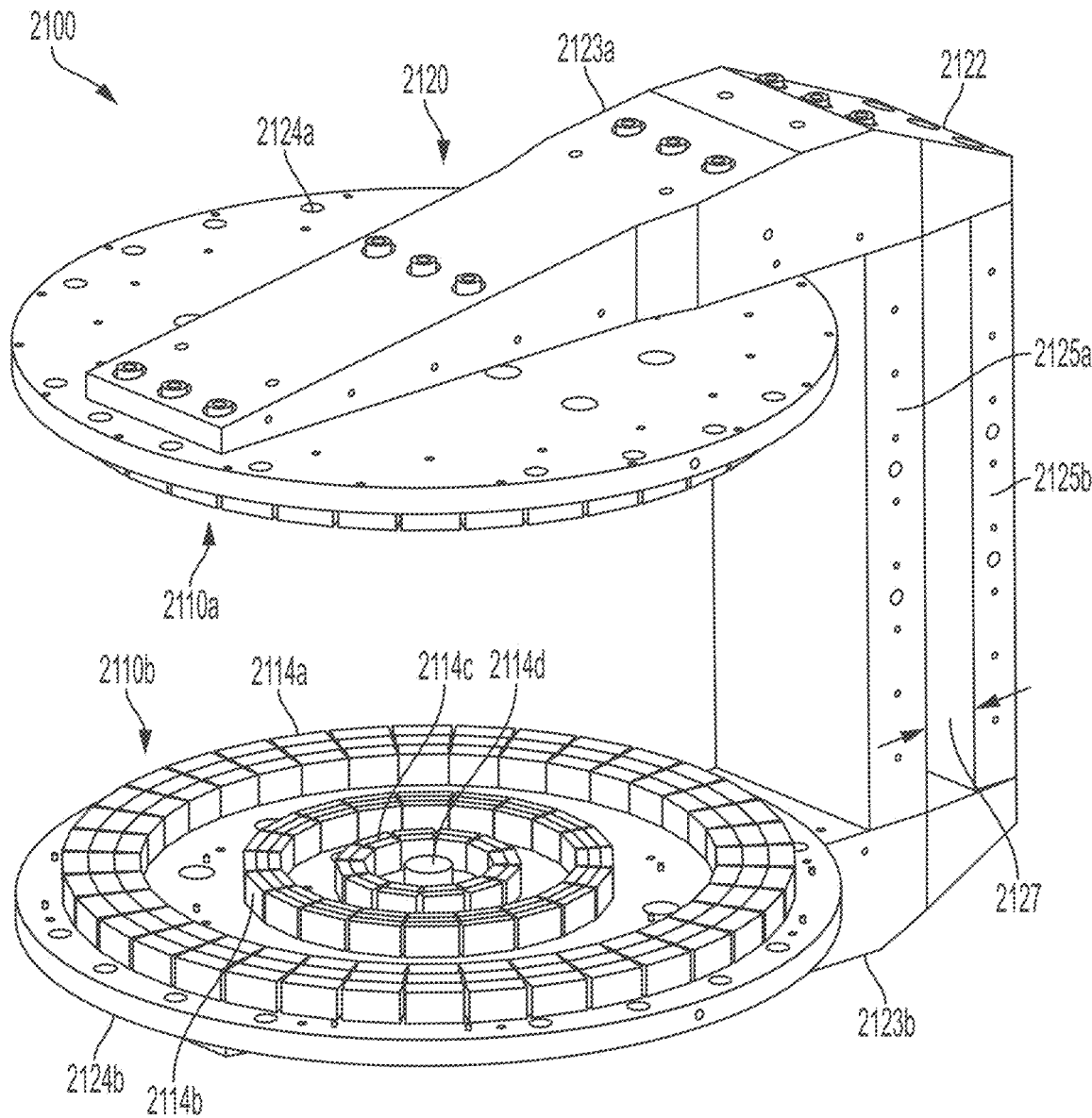
FIGS. 17A and 17B illustrate bi-planar permanent magnet configurations for a $B_0$ magnet, in accordance with some embodiments of the technology described herein.
Figure 17B:
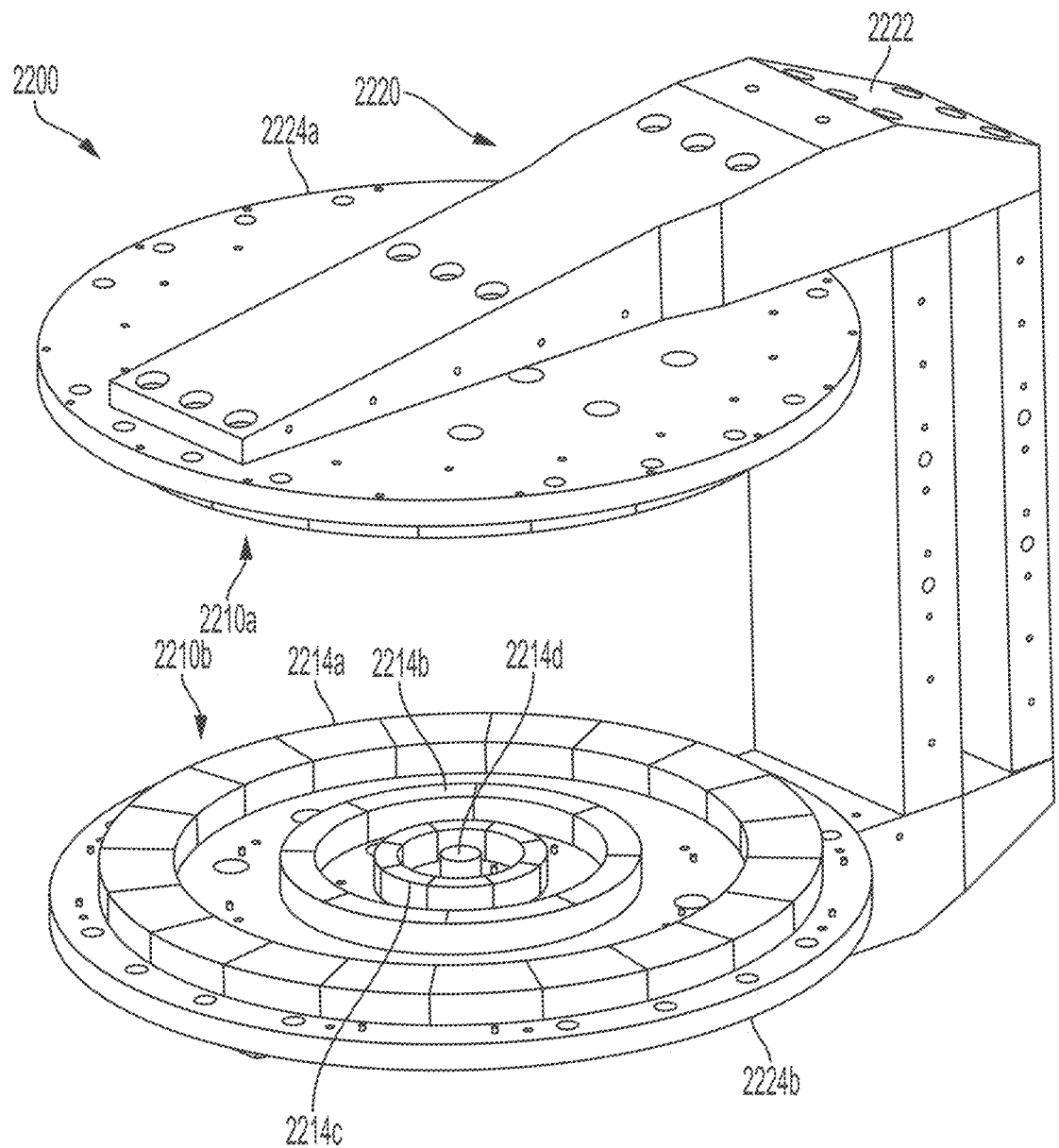

FIGS. 17A and 17B illustrate bi-planar permanent magnet configurations for a $B_0$ magnet, in accordance with some embodiments of the technology described herein. FIG. 17A illustrates a permanent $B_0$ magnet 100, in accordance with some embodiments. In the illustrated embodiment, $B_0$ magnet 2100 is formed by permanent magnets 2110a and 2110b arranged in a bi-planar geometry and a yoke 2120 that captures electromagnetic flux produced by the permanent magnets and transfers the flux to the opposing permanent magnet to increase the flux density between permanent magnets 2110a and 2110b. Each of permanent magnets 2110a and 2110b is formed from a plurality of concentric permanent magnet rings. In particular, as visible in FIG. 17A, permanent magnet 2110b comprises an outer ring of permanent magnets 2114a, a middle ring of permanent magnets 2114b, an inner ring of permanent magnets 2114c, and a permanent magnet disk 2114d at the center. Though shown with four concentric permanent magnet rings, permanent magnet 2110b (and permanent magnet 2110a) may have any suitable number of permanent magnet rings, as aspects of the technology described herein are not limited in this respect. Permanent magnet 2110a may be formed substantially identically to permanent magnet 2110b and, for example, comprise the same set of permanent magnet rings as permanent magnet 2110b.

The permanent magnet material used may be selected depending on the design requirements of the system. For example, according to some embodiments, the permanent magnets (or some portion thereof) may be made of NdFeB, which produces a magnetic field with a relatively high magnetic field per unit volume of material once magnetized. In some embodiments, SmCo material is used to form the permanent magnets, or some portion thereof. While NdFeB produces higher field strengths (and in general is less expensive than SmCo), SmCo exhibits less thermal drift and thus provides a more stable magnetic field in the face of temperature fluctuations. Other types of permanent magnet material(s) may be used as well, as the aspects of the technology described herein are not limited in this respect. In general, the type or types of permanent magnet material utilized will depend, at least in part, on the field strength, temperature stability, weight, cost and/or ease of use requirements of a given $B_0$ magnet implementation.

In some embodiments, the permanent magnet rings are sized and arranged to produce a homogenous field of a desired strength in the imaging region (field of view) between permanent magnets 2110a and 2110b. In the exemplary embodiment illustrated FIG. 17A, each permanent magnet ring comprises a plurality segments, each segment formed using a plurality of permanent magnet blocks stacked in the radial direction and positioned adjacent to one another about the periphery to form the respective ring. The inventors have appreciated that by varying the width (in the direction tangent to the ring) of each permanent magnet, less waste of useful space may be achieved while using less material. For example, the space between stacks that does not produce useful magnetic fields can be reduced by varying the width of the blocks, for example, as function of the radial position of the block, allowing for a closer fit to reduce wasted space and maximize the amount of magnetic field that can be generated in a given space. The dimensions of the blocks may also be varied in any desired way to facilitate the production of a magnetic field of desired strength and homogeneity. For example, in some embodiments, the heights of the blocks different rings may be different from one another and/or the heights of one or more blocks within a particular ring may be different from one another in order to achieve a magnetic field of desired strength and homogeneity.

As shown in FIG. 17A, $B_0$ magnet 2100 further comprises yoke 2120 configured and arranged to capture magnetic flux generated by permanent magnets 2110a and 2110b and direct it to the opposing side of the $B_0$ magnet to increase the flux density in between permanent magnets 2110a and 2110b, increasing the field strength within the field of view of the $B_0$ magnet. By capturing magnetic flux and directing it to the region between permanent magnets 2110a and 2110b, less permanent magnet material can be used to achieve a desired field strength, thus reducing the size, weight and cost of the $B_0$ magnet 2100. Alternatively, for given permanent magnets, the field strength can be increased, thus improving the SNR of the system without having to use increased amounts of permanent magnet material. For exemplary $B_0$ magnet 2100, yoke 2120 comprises a frame 2122 and plates 2124a and 2124b. Plates 2124a and 2124b may capture magnetic flux generated by permanent magnets 2110a and 2110b and direct it to frame 2122 to be circulated via the magnetic return path of the yoke to increase the flux density in the field of view of the $B_0$ magnet. Yoke 2120 may be constructed of any desired ferromagnetic material, for example, low carbon steel, CoFe and/or silicon steel, etc. to provide the desired magnetic properties for the yoke. In some embodiments, plates 2124a and 2124b (and/or frame 2122 or portions thereof) may be constructed of silicon steel or the like in areas where the gradient coils could most prevalently induce eddy currents.

Exemplary frame 2122 comprises arms 2123a and 2123b that attach to plates 2124a and 2124b, respectively, and supports 2125a and 2125b providing the magnetic return path for the flux generated by the permanent magnets. The arms are generally designed to reduce the amount of material needed to support the permanent magnets while providing sufficient cross-section for the return path for the magnetic flux generated by the permanent magnets. Frame 2122 has two supports within a magnetic return path for the $B_0$ field produced by the $B_0$ magnet. Supports 2125a and 2125b are produced with a gap 2127 formed between, providing a measure of stability to the frame and/or lightness to the structure while providing sufficient cross-section for the magnetic flux generated by the permanent magnets. For example, the cross-section needed for the return path of the magnetic flux can be divided between the two support structures, thus providing a sufficient return path while increasing the structural integrity of the frame.

FIG. 17B illustrates a $B_0$ magnet 2200, in accordance with some embodiments. $B_0$ magnet 2200 may share design components with $B_0$ magnet 2100 illustrated in FIG. 17A. In particular, $B_0$ magnet 2200 is formed by permanent magnets 2210a and 2210b arranged in a bi-planar geometry with a yoke 2220 coupled thereto to capture electromagnetic flux produced by the permanent magnets and transfer the flux to the opposing permanent magnet to increase the flux density between permanent magnets 2210a and 2210b. Each of permanent magnets 2210a and 2210b is formed from a plurality of concentric permanent magnets, as shown by permanent magnet 2210b comprising an outer ring of permanent magnets 2214a, a middle ring of permanent magnets 2214b, an inner ring of permanent magnets 2214c, and a permanent magnet disk 2214d at the center. Permanent magnet 2210a may comprise the same set of permanent magnet elements as permanent magnet 2210b. The permanent magnet material used may be selected depending on the design requirements of the system (e.g., NdFeB, SmCo, etc. depending on the properties desired).

The permanent magnet rings are sized and arranged to produce a homogenous field of a desired strength in the central region (field of view) between permanent magnets 2210a and 2210b. In the exemplary embodiment of FIG. 17B, each permanent magnet ring comprises a plurality of circular arc segments sized and positioned to produce a desired $B_0$ magnetic field. In a similar manner to yoke 2120 illustrated in FIG. 17A, yoke 2220 is configured and arranged to capture magnetic flux generated by permanent magnets 2210a and 2210b and direct it to the opposing side of the $B_0$ magnet to increase the flux density between permanent magnets 2210a and 2210b. Yoke 2220 thereby increases the field strength within the field of view of the $B_0$ magnet with less permanent magnet material, reducing the size, weight and cost of the $B_0$ magnet. Yoke 2220 also comprises a frame 2222 and plates 2224a and 2224b that, in a manner similar to that described above in connection with yoke 2220, captures and circulates magnetic flux generated by the permanent magnets 2210a and via the magnetic return path of the yoke to increase the flux density in the field of view of the $B_0$ magnet. The structure of yoke 2220 may be similar to that described above to provide sufficient material to accommodate the magnetic flux generated by the permanent magnets and providing sufficient stability, while minimizing the amount of material used to, for example, reduce the cost and weight of the $B_0$ magnet.

Because a permanent $B_0$ magnet, once magnetized, will produce its own persistent magnetic field, power is not required to operate the permanent $B_0$ magnet to generate its magnetic field. As a result, a significant (often dominant) contributor to the overall power consumption of an MRI system is eliminated through the use of a permanent magnet (as opposed to, e.g., an electro-magnet which requires power), facilitating the development of an MRI system that can be powered using mains electricity (e.g., via a standard wall outlet or common large household appliance outlets). As described above, the inventors have developed low power, portable low-field MRI systems that can be deployed in virtually any environment and that can be brought to the patient who will undergo an imaging procedure. In this way, patients in emergency rooms, intensive care units, operating rooms and a host of other locations can benefit from MRI in circumstances where MRI is conventionally unavailable.

Figure 18B:
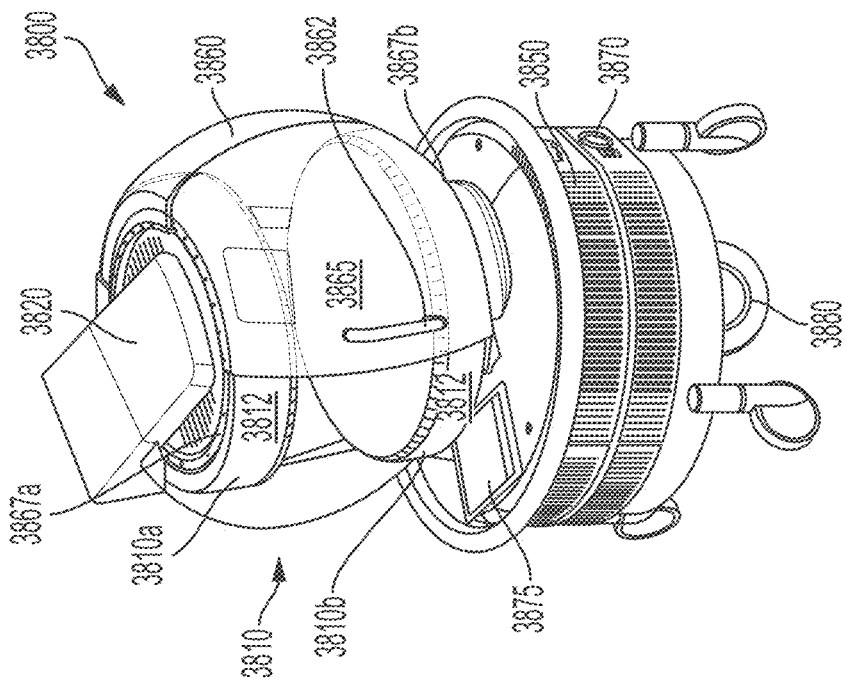
FIGS. 18A and 18B illustrate views of a portable MRI system, in accordance with some embodiments of the technology described herein.
Figure 18A:
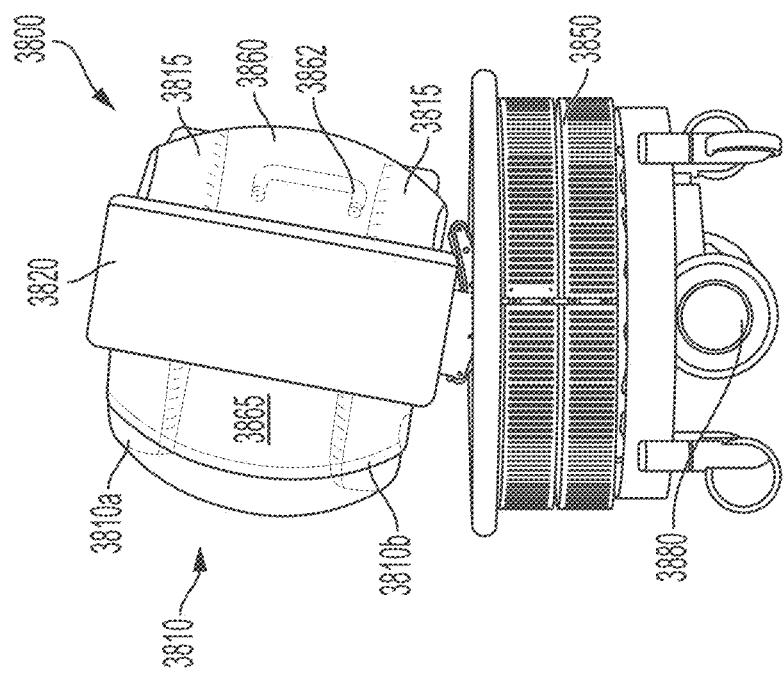

FIGS. 18A and 18B illustrate views of a portable MRI system 3800, in accordance with some embodiments of the technology described herein. Portable MRI system 3800 comprises a $B_0$ magnet 3810 formed in part by an upper magnet 3810a and a lower magnet 3810b having a yoke 3820 coupled thereto to increase the flux density within the imaging region. The $B_0$ magnet 3810 may be housed in magnet housing 3812 along with gradient coils 3815 (e.g., any of the gradient coils described in U.S. application Ser. No. 14/845,652, titled "Low Field Magnetic Resonance Imaging Methods and Apparatus" and filed on Sep. 4, 2015, which is herein incorporated by reference in its entirety). In some embodiments, $B_0$ magnet 3810 comprises an electromagnet. In some embodiments, $B_0$ magnet 3810 comprises a permanent magnet (e.g., any permanent magnet described in U.S. application Ser. No. 15/640,369, titled "LOW-FIELD MAGNETIC RESONANCE IMAGING METHODS AND APPARATUS," filed on Jun. 30, 2017, which is incorporated by reference herein in its entirety). For example, in some embodiments, $B_0$ magnet 3810 may be the permanent magnet 2100 described with reference to FIG. 17A or the permanent magnet 2200 described with reference to FIG. 17B.

Illustrative portable MRI system 3800 further comprises a base 3850 housing the electronics that operates the MRI system. For example, base 3850 may house electronics including, but not limited to, one or more gradient power amplifiers, an on-system computer, a power distribution unit, one or more power supplies, and/or any other power components configured to operate the MRI system using mains electricity (e.g., via a connection to a standard wall outlet and/or a large appliance outlet). For example, base 3870 may house low power components, such as those described herein, enabling at least in part the portable MRI system to be powered front readily available wall outlets. Accordingly, portable MRI system 3800 can be brought to the patient and plugged into a wall outlet in his or her vicinity.

Portable MRI system 3800 further comprises moveable slides 3860 that can be opened and closed and positioned in a variety of configurations. Slides 3860 include electromagnetic shielding 3865, which can be made from any suitable conductive or magnetic material, to form a moveable shield to attenuate electromagnetic noise in the operating environment of the portable MRI system to shield the imaging region from at least some electromagnetic noise. As used herein, the term electromagnetic shielding refers to conductive or magnetic material configured to attenuate the electromagnetic field in a spectrum of interest and positioned or arranged to shield a space, object and/or component of interest. In the context of an MRI system, electromagnetic shielding may be used to shield electronic components (e.g., power components, cables, etc.) of the MRI system, to shield the imaging region (e.g., the field of view) of the MRI system, or both.

The degree of attenuation achieved from electromagnetic shielding depends on a number of factors including the type material used, the material thickness, the frequency spectrum for which electromagnetic shielding is desired or required, the size and shape of apertures in the electromagnetic shielding (e.g., the size of the spaces in a conductive mesh, the size of unshielded portions or gaps in the shielding, etc.) and/or the orientation of apertures relative to an incident electromagnetic field. Thus, electromagnetic shielding refers generally to any conductive or magnetic barrier that acts to attenuate at least some electromagnetic radiation and that is positioned to at least partially shield a given space, object or component by attenuating the at least some electromagnetic radiation.

It should be appreciated that the frequency spectrum for which shielding (attenuation of an electromagnetic field) is desired may differ depending on what is being shielded. For example, electromagnetic shielding for certain electronic components may be configured to attenuate different frequencies than electromagnetic shielding for the imaging region of the MRI system. Regarding the imaging region, the spectrum of interest includes frequencies which influence, impact and/or degrade the ability of the MRI system to excite and detect an MR response. In general, the spectrum of interest for the imaging region of an MRI system correspond to the frequencies about the nominal operating frequency (i.e., the Larmor frequency) at a given $B_0$ magnetic field strength for which the receive system is configured to or capable of detecting. This spectrum is referred to herein as the operating spectrum for the MRI system. Thus, electromagnetic shielding that provides shielding for the operating spectrum refers to conductive or magnetic material arranged or positioned to attenuate frequencies at least within the operating spectrum for at least a portion of an imaging region of the MRI system.

In portable MRI system 3800 illustrated in FIGS. 18A and 18B, the moveable shields are thus configurable to provide shielding in different arrangements, which can be adjusted as needed to accommodate a patient, provide access to a patient, and/or in accordance with a given imaging protocol. For example, for an imaging procedure such as a brain scan, once the patient has been positioned, slides 3960 can be closed, for example, using handle 3862 to provide electromagnetic shielding 3965 around the imaging region except for the opening that accommodates the patient's upper torso. As another example, for an imaging procedure such as a knee scan, slides 3960 may be arranged to have openings on both sides to accommodate the patient's leg or legs. Accordingly, moveable shields allow the shielding to be configured in arrangements suitable for the imaging procedure and to facilitate positioning the patient appropriately within the imaging region.

In some embodiments, a noise reduction system comprising one or more noise reduction and/or compensation techniques may be performed to suppress at least some of the electromagnetic noise that is not blocked or sufficiently attenuated by shielding 3865. In particular, the inventors have developed noise reduction systems configured to suppress, avoid and/or reject electromagnetic noise in the operating environment in which the MRI system is located. According to some embodiments, these noise suppression techniques work in conjunction with the moveable shields to facilitate operation in the various shielding configurations in which the slides may be arranged. For example, when slides 3960 are opened, increased levels of electromagnetic noise will likely enter the imaging region via the openings. As a result, the noise suppression component will detect increased electromagnetic noise levels and adapt the noise suppression and/or avoidance response accordingly. Due to the dynamic nature of the noise suppression and/or avoidance techniques described herein, the noise reduction system is configured to be responsive to changing noise conditions, including those resulting from different arrangements of the moveable shields. Thus, a noise reduction system in accordance with some embodiments may be configured to operate in concert with the moveable shields to suppress electromagnetic noise in the operating environment of the MRI system in any of the shielding configurations that may be utilized, including configurations that are substantially without shielding (e.g., configurations without moveable shields).

To ensure that the moveable shields provide shielding regardless of the arrangements in which the slides are placed, electrical gaskets may be arranged to provide continuous shielding along the periphery of the moveable shield. For example, as shown in FIG. 18B, electrical gaskets 3867a and 3867b may be provided at the interface between slides 3860 and magnet housing to maintain to provide continuous shielding along this interface. According to some embodiments, the electrical gaskets are beryllium fingers or beryllium-copper fingers, or the like (e.g., aluminum gaskets), that maintain electrical connection between shields 3865 and ground during and after slides 3860 are moved to desired positions about the imaging region.

To facilitate transportation, a motorized component 3880 is provide to allow portable MRI system to be driven from location to location, for example, using a control such as a joystick or other control mechanism provided on or remote from the MRI system. In this manner, portable MRI system 3800 can be transported to the patient and maneuvered to the bedside to perform imaging.

The portable MRI systems described herein may be operated from a portable electronic device, such as a notepad, tablet, smartphone, etc. For example, tablet computer 3875 may be used to operate portable MRI system to run desired imaging protocols and to view the resulting images. Tablet computer 3875 may be connected to a secure cloud to transfer images for data sharing, telemedicine, and/or deep learning on the data sets. Any of the techniques of utilizing network connectivity described in U.S. application Ser. No. 14/846,158, titled "Automatic Configuration of a Low Field Magnetic Resonance Imaging System," filed Sep. 4, 2015, which is herein incorporated by reference in its entirety, may be utilized in connection with the portable MRI systems described herein.

Figure 18C:
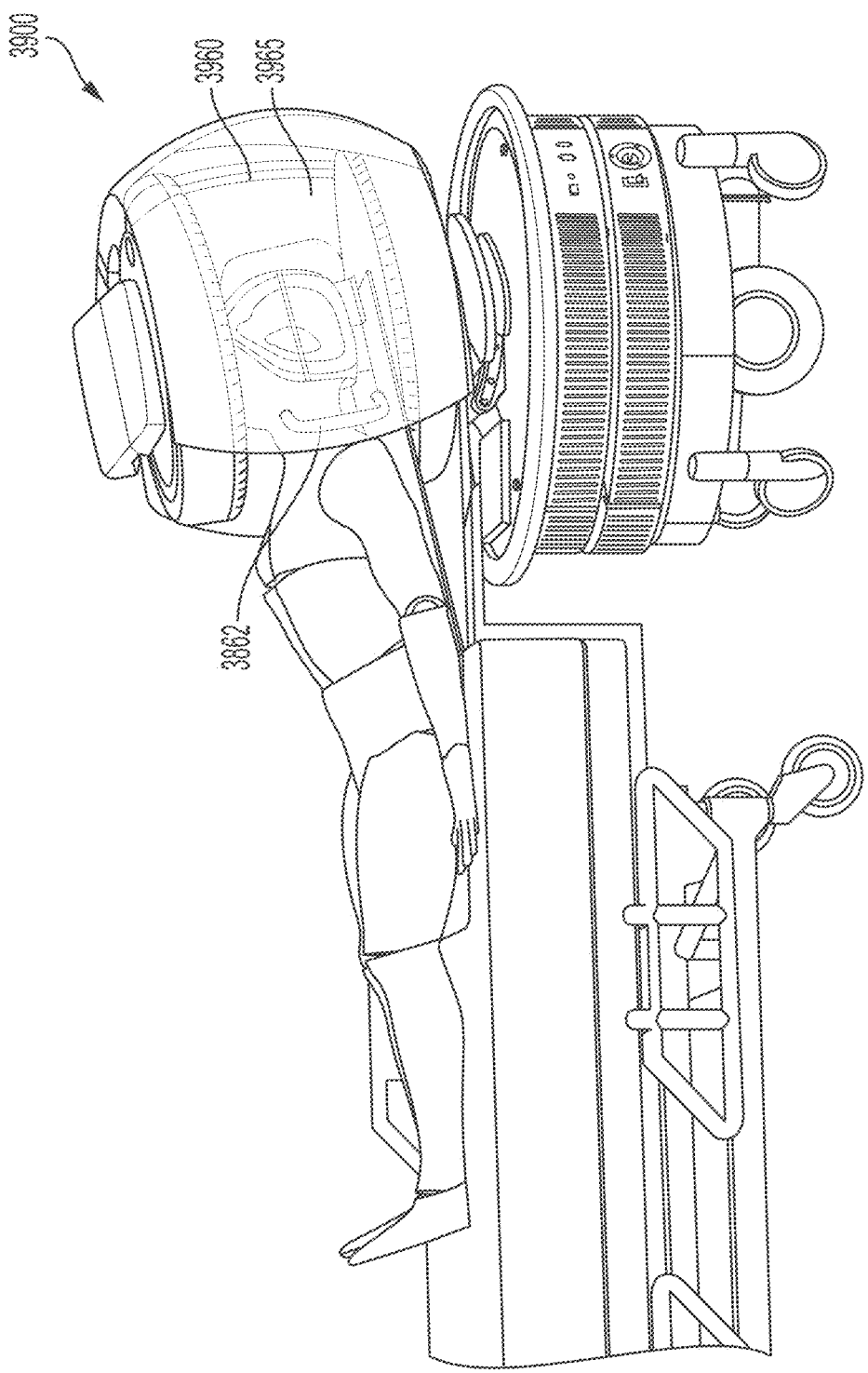
FIG. 18C illustrates a portable MRI system performing a scan of the head, in accordance with some embodiments of the technology described herein.
Figure 18D:
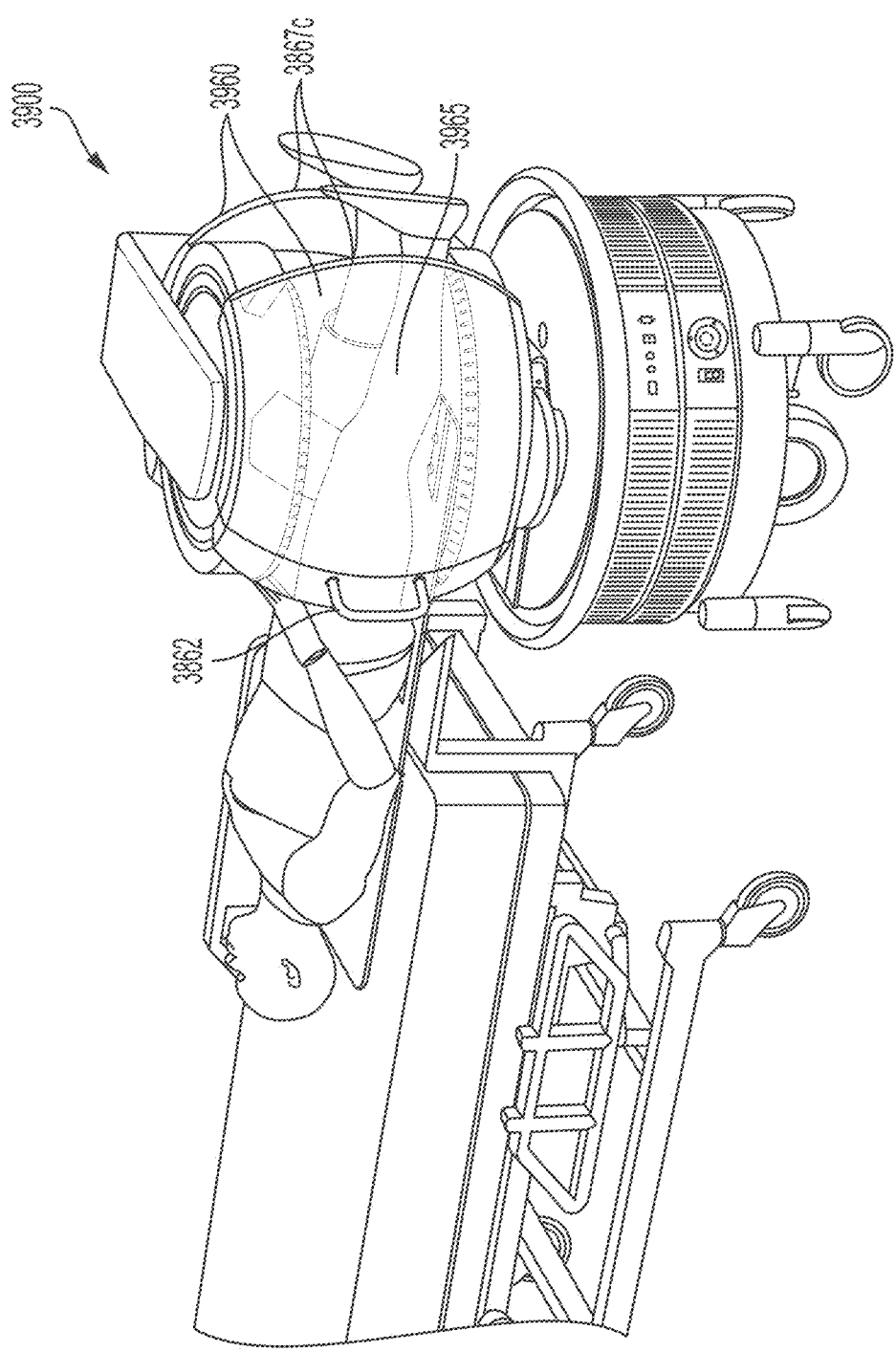
FIG. 18D illustrates a portable MRI system performing a scan of the knee, in accordance with some embodiments of the technology described herein.

As discussed above, FIG. 18C illustrates a portable MRI system 3900 that has been transported to a patient's bedside to perform a brain scan. FIG. 18D illustrates portable MRI system 3900 that has been transported to a patient's bedside to perform a scan of the patient's knee. As shown in FIG. 18D, shield 3960 have electrical gaskets 3867c.

It should be appreciated that the electromagnetic shields illustrated in FIGS. 18A-18D are exemplary and providing shielding for an MRI system is not limited to the example electromagnetic shielding described herein. Electromagnetic shielding can be implemented in any suitable way using any suitable materials. For example, electromagnetic shielding may be formed using conductive meshes, fabrics, etc. that can provide a moveable "curtain" to shield the imaging region. Electromagnetic shielding may be formed using one or more conductive straps (e.g., one or more strips of conducting material) coupled to the MRI system as either a fixed, moveable or configurable component to shield the imaging region from electromagnetic interference, some examples of which are described in further detail below. Electromagnetic shielding may be provided by embedding materials in doors, slides, or any moveable or fixed portion of the housing. Electromagnetic shields may be deployed as fixed or moveable components, as the aspects are not limited in this respect.

Figure 19:
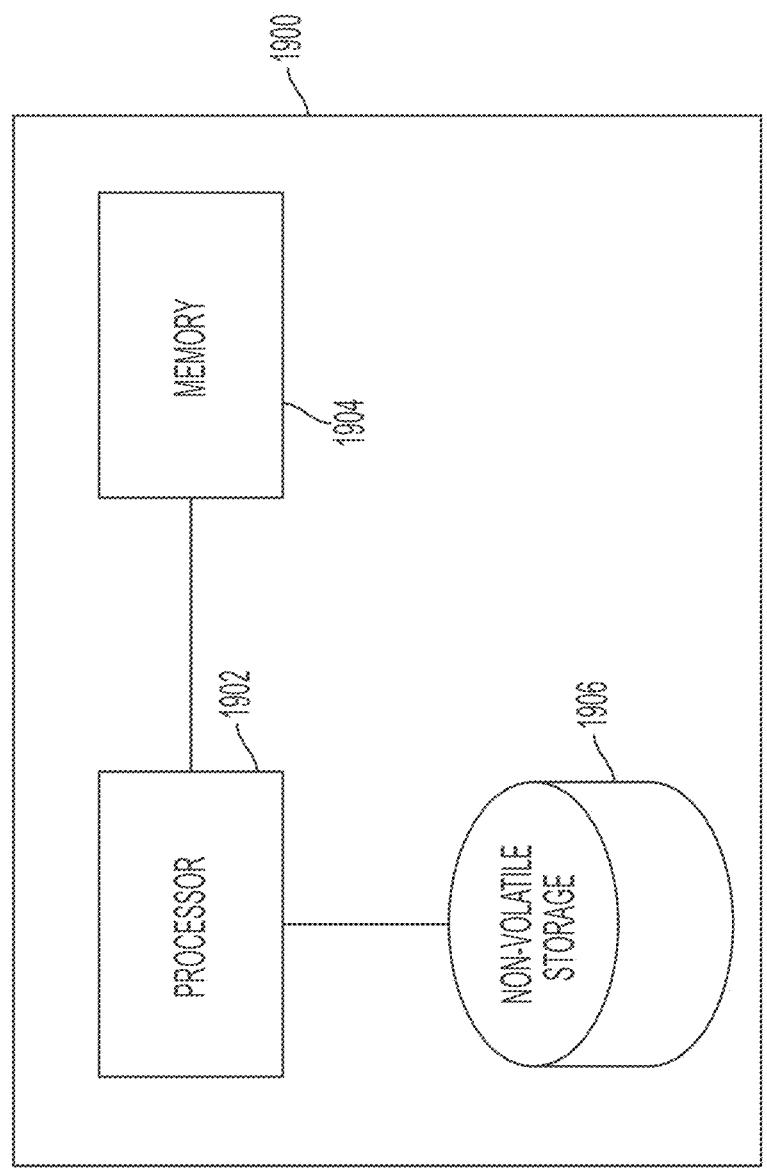
FIG. 19 is a diagram of an illustrative computer system on which embodiments described herein may be implemented.

FIG. 19 is a diagram of an illustrative computer system on which embodiments described herein may be implemented. An illustrative implementation of a computer system 1900 that may be used in connection with any of the embodiments of the disclosure provided herein is shown in FIG. 19. For example, the processes described with reference to FIGS. 2A-2D and 14 may be implemented on and/or using computer system 1900. As another example, the computer system 1900 may be used to train and/or use any of the neural network statistical models described herein. The computer system 1900 may include one or more processors 1910 and one or more articles of manufacture that comprise non-transitory computer-readable storage media (e.g., memory 1920 and one or more non-volatile storage media 1930). The processor 1910 may control writing data to and reading data from the memory 1920 and the non-volatile storage device 1930 in any suitable manner, as the aspects of the disclosure provided herein are not limited in this respect. To perform any of the functionality described herein, the processor 1910 may execute one or more processor-executable instructions stored in one or more non-transitory computer-readable storage media (e.g., the memory 1920), which may serve as non-transitory computer-readable storage media storing processor-executable instructions for execution by the processor 1910.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately" and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

What is claimed is:

1. A method, comprising:
generating a magnetic resonance (MR) image from input MR spatial frequency data using a neural network model configured to process spatial frequency domain data and image domain data, wherein generating the MR image comprises:
applying, to image domain data, at least a first non-uniform Fourier transformation to obtain a first output;
applying at least a second non-uniform Fourier transformation to the input MR spatial frequency data to obtain a second output; and
providing at least the first output and the second output as inputs to a plurality of convolutional layers.

2. The method of claim 1, wherein the neural network model comprises one or more neural network blocks including a first neural network block configured to perform data consistency processing using at least one of the first or second non-uniform Fourier transformations.

3. The method of claim 1, further comprising:
obtaining the input MR spatial frequency data;
generating an initial image from the input MR spatial frequency data using at least one of the first or second non-uniform Fourier transformations; and
applying the neural network model to the initial image at least in part by using a first neural network block of the neural network model to perform data consistency processing using at least one of the first or second non-uniform Fourier transformations.

4. The method of claim 1, wherein a first neural network block of the neural network model is configured to perform data consistency processing at least in part by performing one or more non-uniform Fourier transformations on data by applying a gridding interpolation transformation, a fast Fourier transformation, and a de-apodization transformation to the data.

5. The method of claim 4, wherein applying the gridding interpolation transformation to the data is performed using sparse graphical processing unit (GPU) matrix multiplication.

6. The method of claim 1, wherein a first neural network block of the neural network model comprises:
a data consistency block configured to perform data consistency processing; and
the plurality of convolutional layers or a second plurality of convolutional layers.

7. The method of claim 6, wherein the data consistency block is configured to:
apply the first non-uniform Fourier transformation to a first image, provided as input to the data consistency block, to obtain first MR spatial frequency data; and
apply the second non-uniform Fourier transformation to a difference between the first MR spatial frequency data and the input MR spatial frequency data.

8. The method of claim 7, wherein applying the first non-uniform Fourier transformation to the first image domain data comprises:
applying, to the first image domain data, a de-apodization transformation followed by a Fourier transformation, and followed by a gridding interpolation transformation.

9. The method of claim 6, wherein at least one of the plurality of convolutional layers or the second plurality of convolutional layers include one or more convolutional layers and one or more transposed convolutional layers.

10. The method of claim 6, wherein at least one of the plurality of convolutional layers or the second plurality of convolutional layers have a U-net structure.

11. The method of claim 1, wherein the neural network model comprises a first neural network block that comprises:
the plurality of convolutional layers configured to receive as input:
the image domain data; and
the second output obtained by applying the second non-uniform Fourier transformation to the input MR spatial frequency data, wherein the second non-uniform Fourier transformation is an adjoint non-uniform Fourier transformation.

12. The method of claim 11, wherein the plurality of convolutional layers is further configured to receive as input:
output obtained by applying the first non-uniform Fourier transformation and the second non-uniform Fourier transformation to the image domain data.

13. The method of claim 1, wherein:
the first output is obtained by applying, to the image domain data, the first non-uniform Fourier transformation followed by the second non-uniform Fourier transformation.

14. The method of claim 13, wherein the image domain data, the first output, and the second output are provided as inputs to the plurality of convolutional layers.

15. The method of claim 1, further comprising:
applying a convolutional neural network to a result of applying the first non-uniform Fourier transformation to the image domain data to obtain an intermediate output; and
applying the second non-uniform Fourier transformation to the intermediate output to obtain the first output.

16. The method of claim 1, wherein points in the input MR spatial frequency data were obtained using a non-Cartesian sampling trajectory.

17. The method of claim 16, wherein the first non-uniform Fourier transformation is determined at least in part by using the non-Cartesian sampling trajectory.

18. The method of claim 1, wherein the neural network model comprises a first neural network sub-model configured to process the spatial frequency domain data, and a second neural network sub-model configured to process the image domain data.

19. The method of claim 1, wherein the second non-uniform Fourier transformation is an adjoint non-uniform Fourier transformation.

20. At least one non-transitory computer-readable storage medium storing processor-executable instructions that, when executed by at least one computer hardware processor, cause the at least one computer hardware processor to perform a method comprising:
generating a magnetic resonance (MR) image from input MR spatial frequency data using a neural network model configured to process spatial frequency domain data and image domain data, wherein generating the MR image comprises:
applying, to the image domain data, at least a first non-uniform Fourier transformation to obtain a first output;
applying at least a second non-uniform Fourier transformation to the input MR spatial frequency data to obtain a second output; and
providing at least the first output and the second output as inputs to a plurality of convolutional layers.

21. A magnetic resonance imaging (MRI) system, comprising:
a magnetics system comprising:
a $B_0$ magnet configured to provide a $B_0$ field for the MRI system;
gradient coils configured to provide gradient fields for the MRI system; and
at least one RF coil configured to detect magnetic resonance (MR) signals;
a controller configured to:
control the magnetics system to acquire MR spatial frequency data using a non-Cartesian sampling trajectory; and
generate an MR image from the acquired MR spatial frequency data using a neural network model configured to process spatial frequency domain data and image domain data, wherein generating the MR image comprises:
applying, to the image domain data, at least a first non-uniform Fourier transformation to obtain a first output;

applying at least a second non-uniform Fourier transformation to the input MR spatial frequency data to obtain a second output; and providing at least the first output and the second output as inputs to a plurality of convolutional layers.

22. The MRI system of claim 21, wherein the $B_0$ magnet is a permanent magnet.

* * * * *